(12) United States Patent
Giranda et al.

(10) Patent No.: US 7,790,721 B2
(45) Date of Patent: Sep. 7, 2010

(54) PYRROLOQUINOXALINONE INHIBITORS OF POLY(ADP-RIBOSE)POLYMERASE

(75) Inventors: Vincent L. Giranda, Gurnee, IL (US); Julie M Miyashiro, Morton Grove, IL (US); Thomas D Penning, Elmhurst, IL (US); Keith W. Woods, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/964,788

(22) Filed: Dec. 27, 2007

(65) Prior Publication Data

US 2008/0161292 A1 Jul. 3, 2008

Related U.S. Application Data

(60) Provisional application No. 60/882,270, filed on Dec. 28, 2006.

(51) Int. Cl.
*A61K 31/495* (2006.01)
(52) U.S. Cl. ........................ 514/249; 544/111; 544/344; 546/199; 548/518
(58) Field of Classification Search ................. 514/249; 544/111, 344; 546/199; 548/518
See application file for complete search history.

(56) References Cited

U.S. PATENT DOCUMENTS

| 4,446,323 | A | | 5/1984 | Freed et al. |
| 5,405,847 | A | * | 4/1995 | Dieter et al. ................. 514/250 |
| 6,235,740 | B1 | | 5/2001 | Barrish et al. |
| 2005/0159427 | A1 | | 7/2005 | Bruncko et al. |

FOREIGN PATENT DOCUMENTS

| EP | 1798233 | 6/2007 |
| JP | 2005 8604 | 1/2005 |
| JP | 2005008604 | 1/2005 |
| WO | 1999010341 | 3/1999 |
| WO | 2004078714 | 9/2004 |
| WO | 2006072608 | 7/2006 |
| WO | 2006094210 | 9/2006 |
| WO | 2008017883 | 2/2008 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Amundson, et al., "An Informatics Approach Identifying Markers of Chemosensitivity in Human Cancer Cell Lines1", Cancer Research, 60, 6101-6110 (2000).
Burkart, et al., "Mice lacking the poly(ADP-ribose) polymerase gene are resistant to pancreatic beta-cell destruction and diabetes development induced by streptozocin", Nature Medicine, 5(3), 314-319 (1999).

Chen, et al., "Potentiation of the antitumor activity of cisplatin in mice by 3-aminobenzamide and nicotinamide", Cancer Chemotherapy and Pharmacolog, 22, 303-307 (1988).
Cuzzocrea, er al., "Protective effects of 3-aminobenzamide, and inhibitor of poly(ADP-ribose) synthase in a carrageenan-induced model of local inflammation", European Journal of Pharmacology,342, 67-76 (1998).
Ehrlich, et al., "Inhibition of the induction of collagenase by interleukin-1β in cultured rabbit synovial fibroblasts after treatment with the poly(ADP-ribose)-polymerase inhibitor 3-aminobenzamide", Rheumatol Int, 15, 171-172 (1995).
Holzelova, et al., "Autoimmune Lymphoproliferative Syndrome with Somatic Fas Mutations", New England Journal of Medicine, 351, 1409-1418 (2004).
Kroger, et al., "Synergistic Effects of Thalidomide and Poly(ADP-Ribose) Polymerase Inhibition on Type II Collagen-Induced Arthritis in Mice", Inflammation, 20(2), 203-215 (1996).
Puck, et al., "Immunne Disorders Caused by Defects in the Caspase Cascade", Current Allergy and Asthma Reprts, 3, 378-384 (2003).
Rengan, et al., "Actin cytoskeletal function is spared, but apoptosis is increased, in WAS patient hematopoietic cells", Blood, 95(4), 1283-1292 (2000).
Shimazaki, et al., "Evaluation of apoptosis as a prognostic factor in myelodysplastic syndromes", British Journal of Haematology, 110, 584-590 (2000).
Szabo, et al., "Protection against peroxynitrite-induced fibroblast injury and arthritis development by inhibition of poly (ADP-ribose) synthase", Proc. Natl. Acad. Sci. USA, 95, 3867-3872 (1998).
Thiemermann, et al., "Inhibition of the activity of poly(ADP ribose) synthetase reduces ischemia-reperfusion injury in the heart and skeletal muscle", Proc. Natl. Acad. Sci. USA, 94, 679-683 (1997).
Weltin, et al., "Innunosuppressive Activities of 6(5H)-Phenanthridinone, A New Poly(ADP-Ribose) Polymerase Inhibitor", International Journal of Immunopharmacology, 17(4), 265-271 (1995).

(Continued)

*Primary Examiner*—James O Wilson
*Assistant Examiner*—Douglas M Willis
(74) *Attorney, Agent, or Firm*—Susan L. Steele; Rachel A. Polster; Gregory W. Steele

(57) ABSTRACT

Compounds of formula I

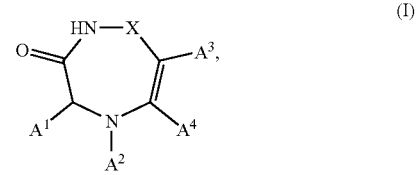

(I)

where X is a bond; $A^1$ and $A^2$, together with the atoms to which they are attached, is pyrrole; and $A^3$ and $A^4$, together with the atoms to which they are attached, are benzene; are poly(ADP-ribose)polymerase inhibitors. The compounds of formula I are useful for the treatment of diseases such as cancer.

8 Claims, No Drawings

OTHER PUBLICATIONS

Campiani, et al., "Novel and Highly Potent 5-HT3 Receptor Agonists Based on a Pyrroloquinoxaline Structure", J Med Chem, 40, 3670-3678 (1997).

Campiani, et al., "Pyrroloquinoxaline Derivatives as High-Affinity and Selective 5-HT3 Receptor Agonists: Synthesis, Further Structure-Activity Relationships, and Biological", J Med Chem, 42, 4362-4379 (1999).

IUPAC 1974 Recommendations for Sec E, Fundamental Stereochemistry, Pure Appl Chem, 45, 13-30 (1976).

Nagarajan, K, et al., "Condensed Heterotricycles: Pyrrolo[1,2-α]quinoxaline Derivatives", Indian Journal of Chemistry, 10, 344-350 (1972).

Nagarajan, et al., "Condensed Heterotricycles: Pyrrolo[1,2-A]quinoxaline Derivatives", Indian Journal of Chemistry, 10, 344-350 (1972).

Adegoke, et al., "Polycyclic Nitrogen Compounds. Part II. Tricyclic Quinoxalinones and Their 4- or 6 Aza Analogues", J of Heterocyclic Chemistry, 15-09-15-12 (1983).

Adegoke, et al., "Polycyclic Nitrogen Compounds. Part. I Synthesis of New Heterotricyclic Quinoxalinones with Bridgehead Nitrogen Atoms", J of Heterocyclic Chemistry, 19(5), 1169-1172 (1982).

Anzini, et al., "5,6-Dihydro-5-(4-[4-(2-methoxyphenyl)-1-piperazinyl]butyl)-4H-pyrrolo[1,2-a][1,4]benzodiazepine-4,6-dione and related compounds as new 5-HT1A", CAS (1993).

Babajide, et al., "Use of the Nuclear Overhauser Effect in the Determination of the Orientation of Aromatic Substitution in Tricyclic Quinoxalinones", J Chem Soc Perkin Trans I, 1997-1999 (1988).

de la LLosa, et al, "Degradation Systematique des peptides par reduction de leurs derives N, nitro-2 methanesulfonyl-4 phenyles", Bulletin De La Societe Chimique De France, 1621-1625 (1960).

Ceccarelli, et al., "Imidazo[1,2-a]quinoxalin-4-amines: A novel class of nonxanthine A1-adenosine receptor antagonists1", Eur J Med Che, 33, 943-955 (1998).

Chen, et al., "Synthesis and SAR of Novel Imidazoquinoxaline-Based Lck Inhibitors: Improvement of Cell Potency", Bioorganic & Medicinal Chemistry Letters, 12, 3153-3156 (2002).

Chen, et al., Reaction of quinoxalin-2-ones with TosMIC reagent: synthesis of Imidazo[1,5-a]quinoxalin-4-ones, Tetrahedron Letters, 42, 4293-4295 (2001).

Chicharro, et al., "Synthesis of Tri- and Tetracyclic Condensed Quinoxalin-2-ones Fused Across the C-3-N-4 Bond", Eur J Org Chem, 12, 2314-2326 (2003).

Davey, et al., "Novel Coompunds Possessing Potent cAMP and cGMP Phosphodiesterase Inhibitory Activity. Synthesis and Cardiovascular Effects of a Series of Imidazo[1,2-a]quinoxalinones and Imidazo[1,5-a]quinoxalinones and Their Aza Analogues", J Med Chem 34, 2671-2677 (1991).

Guillon, et al, "Synthesis, Antimalarial Activity, and Molecular Modeling of New Pyrrolo[1,2-a]quinoxalines, Bispyrrolo [1,2-a]quinoxalines, Bispyrido[3,2-e]pyrrolo[1,2-a]pyrazines, and Bispyrrolo[1,2-a]thieno[3,2-e]pyrazines", J Med Chem, 47, 1997-2009 (2004).

Holley, et al., "A New Stepwise Degradation of Peptides", J Am Chem Soc, 74(21), 5445-5448 (1952).

Kher, et al., Regiospecific Oxidative Nitration of 3,4-Dihydro-6,7-disubstituted Quinoxaline-2(1H)-ones Gives 1,4-Dihydro-5-nitro-6,7-disubstituted Quinoxaline-2,3-diones, Potent Antagonists at the NMDA/Glycine Site, J Org Chem, 60(18), 58-38-5842 (1995).

McQuaid, et al., "Synthesis and Excitatory Amino Acid Pharmacology of a Series of Heterocyclic-Fused Quinoxalinones and Quinazolinones", J Of Med Chem, 35(18), 3319-3324 (1992).

Morjaria, et al., Impairment of TNF-a Production and Action by Imidazo[1,2- A] Quinoxalines, A Derivative Family Which Displays Potential Anti-Imflammatory Properties, Int J of Immun and Pharmacology, 19(3), 525-538 (2006).

Ohmori, et al., "8-(1H-Imidazol-1-yl)-7-nitro-4(5H)-imidazo[1,2-a]quinoxalinone and Related Compounds: Synthesis and Structure-Activity Relationships for the AMPA-type Non-NMDA Receptor", J Med Chem 40(13), 2053-2063 (1997).

Prunier, et al., "Novel and Selective Partial Agonists of 5-HT3 Receptors. 2. Synthesis and Biological Evaluation of Piperazinopyridopyrrolopyrazines, Piperazinopyrroloquinoxalines, and Piperazinopyridopyrroloquinoxalines", J Med Chem, 40(12), 1808-1819 (1997).

Stien, "Synthesis of amides from carbonic acid derivatives", CAS 2005.

* cited by examiner

PYRROLOQUINOXALINONE INHIBITORS OF POLY(ADP-RIBOSE)POLYMERASE

This application claims priority from U.S. Provisional Patent Application Ser. No. 60/882,270 filed Dec. 28, 2006 which is incorporated by reference in its entirety.

FIELD OF THE INVENTION

This invention relates to inhibitors of poly(ADP-ribose) polymerase, ways to make them and methods of treating patients using them.

BACKGROUND OF THE INVENTION

Poly(ADP-ribose)polymerase (PARP) is essential for facilitating DNA repair, controlling RNA transcription, mediating cell death and regulating immune response. This activity makes PARP inhibitors targets for a number of disorders. PARP inhibitors have shown utility for treating diseases such as ischemia reperfusion injury, inflammatory disease, retroviral infections, ischemia reperfusion injury, myocardial infarction, stroke and other neural trauma, organ transplantation, reperfusion of the eye, kidney, gut and skeletal muscle, arthritis, gout, inflammatory bowel disease, CNS inflammation such as MS and allergic encephalitis, sepsis, septic shock, hemmorhagic shock, pulmonary fibrosis, and uveitis, diabetes and Parkinsons disease, liver toxicity following acetominophen overdose, cardiac and kidney toxicities from doxorubicin and platinum-based antineoplastic agents and skin damage secondary to sulfur mustards. PARP inhibitors have also been shown to potentiate radiation and chemotherapy by increasing cell death of cancer cells, limiting tumor growth, decreasing metastasis, and prolonging the survival of tumor-bearing animals. There is therefore a need in the therapeutic arts for PARP inhibitors.

SUMMARY OF THE INVENTION

One embodiment of this invention, therefore, pertains to compounds that inhibit the activity of poly(ADP-ribose)polymerase and have formula I

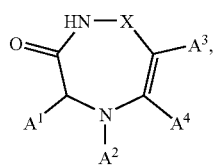

(I)

or a salt thereof, wherein

X is a bond or $CH_2$;

$A^1$ and $A^2$, together with the atoms to which they are attached, are pyrrole, imidazole, piperidine, or pyrrolidine;

$A^3$ and $A^4$, together with the atoms to which they are attached, are benzene which is substituted with $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I;

$R^1$ is $R^2$, $R^3$, $R^4$ or $R^5$;

$R^2$ is phenyl which is unfused or fused with benzene, heteroarene, cycloalkane, cycloalkene, heterocycloalkane or heterocycloalkene;

$R^3$ is heteroarene which is unfused or fused with benzene, heteroarene, cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^5$ is alkyl, alkenyl or alkynyl, each of which is unsubstituted or substituted with one or two of independently selected $R^6$, C(O)OH, $NH_2$, $NHR^6$, $N(R^6)_2$, $C(O)R^6$, $C(O)NH_2$, $C(O)NHR^6$, $C(O)N(R^6)_2$, $NHC(O)R^6$, $NR^6C(O)R^6$, $NR^6S(O)_2R^6$, F, Cl, Br or I;

$R^6$ is $R^7$, $R^8$, $R^9$ or $R^{10}$;

$R^7$ is phenyl which is unfused or fused with benzene, heteroarene, cycloalkane, cycloalkene, heterocycloalkane or heterocycloalkene;

$R^8$ is heteroarene which is unfused or fused with benzene, heteroarene, cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{10}$ is alkyl, alkenyl or alkynyl, each of which is unsubstituted or substituted with one or two of independently selected $R^{11}$, C(O)OH, $NH_2$, $NHR^{11}$, $N(R^{11})_2$, $C(O)R^{11}$, $C(O)OR^{11}$, $C(O)NH_2$, $C(O)NHR^{11}$, $C(O)N(R^{11})_2$, $NHC(O)R^{11}$, $NR^{11}C(O)R^{11}$, F, Cl, Br or I;

$R^{11}$ is $R^{12}$, $R^{13}$, $R^{14}$ or $R^{14A}$;

$R^{12}$ is phenyl which is unfused or fused with benzene, heteroarene, cycloalkane, cycloalkene, heterocycloalkane or heterocycloalkene;

$R^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{14A}$ is alkyl, alkenyl, or alkynyl;

wherein the moieties represented by $A^1$ and $A^2$ and $A^2$ and $A^3$ and the moieties represented by $R^2$, $R^3$, $R^4$, $R^7$, $R^8$, $R^9$, $R^{12}$, $R^{13}$ and $R^{14}$ are independently unsubstituted or further unsubstituted or independently substituted or further substituted with $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)NHR^{15}$, $NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;

wherein $R^{15}$ is $R^{16}$, $R^{17}$, $R^{18}$ or $R^{19}$;

$R^{16}$ is phenyl which is unfused or fused with benzene;

$R^{17}$ is heteroaryl which is unfused or fused with benzene;

$R^{18}$ is cycloalkyl, cycloalkenyl, heterocycloalkyl or heterocycloalkenyl, each of which is unfused or fused with benzene;

$R^{19}$ is alkyl, alkenyl or alkynyl, each of which is unsubstituted or substituted with one or two of independently selected $R^{20}$, C(O)OH, $NH_2$, $NHR^{20}$ or $N(R^{20})_2$, $C(O)R^{20}$, $C(O)NH_2$, $C(O)NHR^{20}$, $C(O)N(R^{20})_2$, $NHC(O)R^{20}$, $NR^{20}C(O)R^{20}$, F, Cl, Br or I;

$R^{20}$ is $R^{21}$ or $R^{21A}$;

$R^{21}$ is phenyl, heteroaryl, cycloalkyl, cycloalkenyl, heterocycloalkyl, or heterocycloalkenyl;

$R^{214}$ is alkyl, alkenyl or alkynyl, each of which is unsubstituted or substituted with one or two of independently selected $R^{22}$, C(O)OH, $NH_2$, $NHR^{22}$ or $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, F, Cl, Br or I;

$R^{22}$ is phenyl, heteroaryl, cycloalkyl, cycloalkenyl, heterocycloalkyl or heterocycloalkenyl;

wherein the moieties represented by $R^{16}$, $R^{17}$, $R^{18}$, $R^{21}$, and $R^{22}$ are independently unsubstituted or further unsubstituted or independently substituted or further substituted with $R^{23}$, $OR^{23}$, $SR^{23}$, $S(O)R^{23}$, $SO_2R^{23}$, $NH_2$, $NHR^{23}$, $N(R^{23})_2$, $C(O)R^{23}$, $C(O)NH_2$, $C(O)NHR^{23}$, $C(O)N(R^{23})_2$, $NHC(O)R^{23}$, $NR^{23}C(O)R^{23}$, $NHSO_2R^{23}$, $NR^{23}SO_2R^{23}$, $NHC(O)OR^{23}$, $NR^{23}C(O)OR^{23}$, $SO_2NH_2$, $SO_2NHR^{23}$, $SO_2N(R^{23})_2$, $NHC(O)NH_2$, $NHC(O)NHR^{23}$, $NHC(O)N(R^{23})_2$, $NR^{23}C(O)N(R^{23})_2$, OH, (O), C(O)OH, CN, $CF_3$, $OCF_3$, $CF_2CF_3$, F, Cl, Br or I;

wherein $R^{23}$ is $R^{24}$, $R^{25}$, $R^{26}$ or $R^{27}$;

$R^{24}$ is phenyl which is unfused or fused with benzene;

$R^{25}$ is heteroaryl which is unfused or fused with benzene;

$R^{26}$ is cycloalkyl, cycloalkenyl, heterocycloalkyl or heterocycloalkenyl, each of which is unfused or fused with benzene;

$R^{27}$ is alkyl, alkenyl or alkynyl, each of which is unsubstituted or substituted with one or two of independently selected $R^{28}$, C(O)OH, $NH_2$, $NHR^{28}$ or $N(R^{28})_2$, $C(O)R^{28}$, $C(O)NH_2$, $C(O)NHR^{28}$, $C(O)N(R^{28})_2$, $NHC(O)R^{28}$, $NR^{28}C(O)R^{28}$, F, Cl, Br or I;

$R^{28}$ is phenyl, heteroaryl, cycloalkyl, cycloalkenyl, heterocycloalkyl, heterocycloalkenyl or $R^{29}$;

$R^{29}$ is alkyl, alkenyl or alkynyl, each of which is unsubstituted or substituted with one or two of independently selected $R^{30}$, C(O)OH, $NH_2$, $NHR^{30}$ or $N(R^{30})_2$, $C(O)R^{30}$, $C(O)NH_2$, $C(O)NHR^{30}$, $C(O)N(R^{30})_2$, $NHC(O)R^{30}$, $NR^{30}OC(O)R^{30}$, F, Cl, Br or I; and $R^{30}$ is phenyl, heteroaryl, cycloalkyl, cycloalkenyl, heterocycloalkyl or heterocycloalkenyl.

Still another embodiment comprises pharmaceutical compositions comprising a compound having formula I and an excipient.

Still another embodiment comprises methods of inhibiting PARP in a mammal comprising administering thereto a therapeutically acceptable amount of a compound having formula I.

Still another embodiment comprises methods of treating cancer in a mammal comprising administering thereto a therapeutically acceptable amount of a compound having formula I

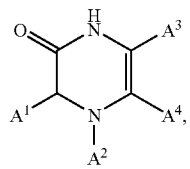

(I)

or a salt thereof, wherein $A^1$ and $A^2$, together with the atoms to which they are attached, are pyrrole;

$A^3$ and $A^4$, together with the atoms to which they are attached, are benzene which is substituted with $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^{11}C(O)R^{11}$, $NHSO_2R^{11}$, $NR^{11}SO_2R^{11}$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I;

$R^1$ is $R^2$, $R^3$, $R^4$ or $R^5$;

$R^2$ is phenyl which is unfused or fused with benzene, heteroarene, cycloalkane, cycloalkene, heterocycloalkane or heterocycloalkene;

$R^3$ is heteroarene which is unfused or fused with benzene, heteroarene, cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^5$ is alkyl, alkenyl or alkynyl, each of which is unsubstituted or substituted with one or two of independently selected $R^6$, C(O)OH, $NH_2$, $NHR^6$ or $N(R^6)_2$, $C(O)R^6$, $C(O)NH_2$, $C(O)NHR^6$, $C(O)N(R^6)_2$, $NHC(O)R^6$, $NR^6C(O)R^6$, F, Cl, Br or I;

$R^6$ is $R^7$, $R^8$, $R^9$ or $R^{10}$;

$R^7$ is phenyl which is unfused or fused with benzene, heteroarene, cycloalkane, cycloalkene, heterocycloalkane or heterocycloalkene;

$R^8$ is heteroarene which is unfused or fused with benzene, heteroarene, cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{10}$ is alkyl, alkenyl or alkynyl, each of which is unsubstituted or substituted with one or two of independently selected $R^{11}$, C(O)OH, $NH_2$, $NHR^{11}$ or $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, F, Cl, Br or I;

$R^{11}$ is $R^{12}$, $R^{13}$ or $R^{14}$;

$R^{12}$ is phenyl which is unfused or fused with benzene, heteroarene, cycloalkane, cycloalkene, heterocycloalkane or heterocycloalkene;

$R^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein the moieties represented by $A^1$ and $A^2$ and $A^2$ and $A^3$ and the moieties represented by $R^2$, $R^3$, $R^4$, $R^7$, $R^8$, $R^9$, $R^{12}$, $R^{13}$ or $R^{14}$ are independently unsubstituted or further unsubstituted or independently substituted or further substituted with $R^{20}$, $OR^{20}$, $SR^{20}$, $S(O)R^{20}$, $SO_2R^{20}$, $NH_2$, $NHR^{20}$, $N(R^{20})_2$, $C(O)R^{20}$, $C(O)NH_2$, $C(O)NHR^{20}$, $C(O)N(R^{20})_2$, $NHC(O)R^{20}$, $NR^{10}C(O)R^{20}$, $NHSO_2R^{20}$, $NR^{20}SO_2R^{20}$, $NHC(O)OR^{20}$, $NR^{20}C(O)OR^{20}$, $SO_2NH_2$, $SO_2NHR^{20}$, $SO_2N(R^{20})_2$, $NHC(O)NH_2$, $NHC(O)NHR^{20}$, $NHC(O)N(R^{20})_2$, $NR^{20}C(O)N(R^{20})_2$, OH, (O), C(O)OH, CN, $CF_3$, $OCF_3$, $CF_2CF_3$, F, Cl, Br or I;

wherein $R^{20}$ is $R^{21}$, $R^{22}$, $R^{23}$ or $R^{24}$;

$R^{21}$ is phenyl which is unfused or fused with benzene;

$R^{22}$ is heteroaryl which is unfused or fused with benzene;

$R^{23}$ is cycloalkyl, cycloalkenyl, heterocycloalkyl or heterocycloalkenyl, each of which is unfused or fused with benzene;

$R^{24}$ is alkyl, alkenyl or alkynyl, each of which is unsubstituted or substituted with one or twoo of independently selected $R^{25}$, C(O)OH, $NH_2$, $NHR^{25}$ or $N(R^{25})_2$, $C(O)R^{25}$, $C(O)NH_2$, $C(O)NHR^{25}$, $C(O)N(R^{25})_2$, $NHC(O)R^{25}$, $NR^{25}C(O)R^{25}$, F, Cl, Br or I;

$R^{25}$ is phenyl, heteroaryl, cycloalkyl, cycloalkenyl, heterocycloalkyl, heterocycloalkenyl or $R^{26}$;

$R^{26}$ is alkyl, alkenyl or alkynyl, each of which is unsubstituted or substituted with one or two of independently selected $R^{27}$, C(O)OH, $NH_2$, $NHR^{27}$ or $N(R^{27})_2$, $C(O)R^{27}$, $C(O)NH_2$, $C(O)NHR^{27}$, $C(O)N(R^{27})_2$, $NHC(O)R^{27}$, $NR^{17}C(O)R^{27}$, F, Cl, Br or I;

$R^{27}$ is phenyl, heteroaryl, cycloalkyl, cycloalkenyl, heterocycloalkyl or heterocycloalkenyl.

Still another embodiment comprises methods for decreasing tumor volume in a mammal comprising administering thereto a therapeutically acceptable amount of a compound having formula IA

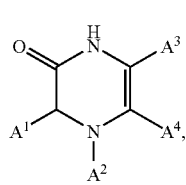

(IA)

and salts thereof, wherein $A^1$ and $A^2$, together with the atoms to which they are attached, are pyrrole;

$A^3$ and $A^4$, together with the atoms to which they are attached, are benzene which is substituted with $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^{11}C(O)R^{11}$, $NHSO_2R^{11}$, $NR^{11}SO_2R^{11}$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I;

$R^1$ is $R^2$, $R^3$, $R^4$ or $R^5$;

$R^2$ is phenyl which is unfused or fused with benzene, heteroarene, cycloalkane, cycloalkene, heterocycloalkane or heterocycloalkene;

$R^3$ is heteroarene which is unfused or fused with benzene, heteroarene, cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^5$ is alkyl, alkenyl or alkynyl, each of which is unsubstituted or substituted with one or two of independently selected $R^6$, C(O)OH, $NH_2$, $NHR^6$ or $N(R^6)_2$, $C(O)R^6$, $C(O)NH_2$, $C(O)NHR^6$, $C(O)N(R^6)_2$, $NHC(O)R^6$, $NR^6C(O)R^6$, F, Cl, Br or I;

$R^6$ is $R^7$, $R^8$, $R^9$ or $R^{10}$;

$R^7$ is phenyl which is unfused or fused with benzene, heteroarene, cycloalkane, cycloalkene, heterocycloalkane or heterocycloalkene;

$R^8$ is heteroarene which is unfused or fused with benzene, heteroarene, cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

$R^{10}$ is alkyl, alkenyl or alkynyl, each of which is unsubstituted or substituted with one or two of independently selected $R^{11}$, C(O)OH, $NH_2$, $NHR^{11}$ or $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, F, Cl, Br or I;

$R^{11}$ is $R^{12}$, $R^{13}$ or $R^{14}$;

$R^{12}$ is phenyl which is unfused or fused with benzene, heteroarene, cycloalkane, cycloalkene, heterocycloalkane or heterocycloalkene;

$R^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein the moieties represented by $A^1$ and $A^2$ and $A^2$ and $A^3$ and the moieties represented by $R^2$, $R^3$, $R^4$, $R^7$, $R^8$, $R^9$, $R^{12}$, $R^{13}$ or $R^{14}$ are independently unsubstituted or further unsubstituted or independently substituted or fuirther substituted with $R^{20}$, $OR^{20}$, $SR^{20}$, $S(O)R^{20}$, $SO_2R^{20}$, $NH_2$, $NHR^{20}$, $N(R^{20})_2$, $C(O)R^{20}$, $C(O)NH_2$, $C(O)NHR^{20}$, $C(O)N(R^{20})_2$, $NHC(O)R^{20}$, $NR^{10}C(O)R^{20}$, $NHSO_2R^{20}$, $NR^{20}SO_2R^{20}$, $NHC(O)OR^{20}$, $NR^{20}C(O)OR^{20}$, $SO_2NH_2$, $SO_2NHR^{20}$, $SO_2N(R^{20})_2$, $NHC(O)NH_2$, $NHC(O)NHR^{20}$, $NHC(O)N(R^{20})_2$, $NR^{20}C(O)N(R^{20})_2$, OH, (O), C(O)OH, CN, $CF_3$, $OCF_3$, $CF_2CF_3$, F, Cl, Br or I;

wherein $R^{20}$ is $R^{21}$, $R^{22}$, $R^{23}$ or $R^{24}$;

$R^{21}$ is phenyl which is unfused or fused with benzene;

$R^{22}$ is heteroaryl which is unfused or fused with benzene;

$R^{23}$ is cycloalkyl, cycloalkenyl, heterocycloalkyl or heterocycloalkenyl, each of which is unfused or fused with benzene;

$R^{24}$ is alkyl, alkenyl or alkynyl, each of which is unsubstituted or substituted with one or two of independently selected $R^{25}$, C(O)OH, $NH_2$, $NHR^{25}$ or $N(R^{25})_2$, $C(O)R^{25}$, $C(O)NH_2$, $C(O)NHR^{25}$, $C(O)N(R^{25})_2$, $NHC(O)R^{25}$, $NR^{25}C(O)R^{25}$, F, Cl, Br or I;

$R^{25}$ is phenyl, heteroaryl, cycloalkyl, cycloalkenyl, heterocycloalkyl, heterocycloalkenyl or $R^{26}$;

$R^{26}$ is alkyl, alkenyl or alkynyl, each of which is unsubstituted or substituted with one or two of independently selected $R^{27}$, C(O)OH, $NH_2$, $NHR^{27}$ or $N(R^{27})_2$, $C(O)R^{27}$, $C(O)NH_2$, $C(O)NHR^{27}$, $C(O)N(R^{27})_2$, $NHC(O)R^{27}$, $NR^{17}C(O)R^{27}$, F, Cl, Br or I; and $R^{27}$ is phenyl, heteroaryl, cycloalkyl, cycloalkenyl, heterocycloalkyl or heterocycloalkenyl.

Still another embodiment comprises a method of treating leukemia, colon cancer, glioblastomas, lymphomas, melanomas, carcinomas of the breast or cervical carcinomas in a mammal comprising administering thereto a therapeutically acceptable amount of a compound having formula I.

Still another embodiment comprises methods for potentiation of cytotoxic cancer therapy in a mammal comprising administering thereto a therapeutically acceptable amount of a compound having formula I.

Still another embodiment comprises methods for potentiation of radiation therapy in a mammal comprising administering thereto a therapeutically acceptable amount of a compound having formula I.

Still another embodiment comprises methods of treating ischemia reperfusion injury associated with myocardial infarction, stroke, neural trauma or organ transplantation in a mammal comprising administering thereto a therapeutically acceptable amount of a compound having formula I.

Still another embodiment comprises methods of treating reperfusion of the eye, kidney, gut or skeletal muscle in a mammal comprising administering thereto a therapeutically acceptable amount of a compound having formula I.

Still another embodiment comprises methods of treating arthritis, gout, inflammatory bowel disease, CNS inflammation, multiple sclerosis, allergic encephalitis, sepsis, septic shock, hemmorhagic shock, pulmonary fibrosis or uveitis in a mammal comprising administering thereto a therapeutically acceptable amount of a compound having formula I.

Still another embodiment comprises a method of treating rheumatoid arthritis or septic shock in a mammal comprising administering thereto a therapeutically acceptable amount of a compound having formula I.

Still another embodiment comprises methods of treating diabetes or Parkinsons disease in a mammal comprising administering thereto a therapeutically acceptable amount of a compound having formula I.

Still another embodiment comprises methods of treating hypoglycemia in a mammal comprising administering thereto a therapeutically acceptable amount of a compound having formula I.

Still another embodiment comprises methods of treating retroviral infection in a mammal comprising administering thereto a therapeutically acceptable amount of a compound having formula I.

Still another embodiment comprises methods of treating liver toxicity following acetominophen overdose in a mammal comprising administering thereto a therapeutically acceptable amount of a compound having formula I.

Still another embodiment comprises a method of treating cardiac or kidney toxicities from doxorubicin or platinum based antineoplastic agents in a mammal comprising administering thereto a therapeutically acceptable amount of a compound having formula I.

Still another embodiment comprises methods of treating skin damage secondary to sulfur mustards in a mammal comprising administering thereto a therapeutically acceptable amount of a compound having formula I.

Still another embodiment comprises the compounds:
7-(cyclohexylamino)methyl)pyrrolo[1,2-a]quinoxalin-4(5H)-one,
7-(((cyclohexylmethyl)amino)methyl)pyrrolo[1,2-a]quinoxalin-4(5H)-one,
7-((cyclobutylamino)methyl)pyrrolo[1,2-a]quinoxalin-4(5H)-one,
7-((cyclopentylamino)methyl)pyrrolo[1,2-a]quinoxalin-4(5H)-one,
7-((cyclopropylamino)methyl)pyrrolo[1,2-a]quinoxalin-4(5H)-one,
7-(piperidin-1-ylmethyl)pyrrolo[1,2-a]quinoxalin-4(5H)-one,
7-(pyrrolidin-1-ylmethyl)pyrrolo[1,2-a]quinoxalin-4(5H)-one,
8-((cyclohexylamino)methyl)pyrrolo[1,2-a]quinoxalin-4(5H)-one,
8-(((cyclohexylmethyl)amino)methyl)pyrrolo[1,2-a]quinoxalin-4(5H)-one,
7-((isopropylamino)methyl)pyrrolo[1,2-a]quinoxalin-4(5H)-one,
7-((benzylamino)methyl)pyrrolo[1,2-a]quinoxalin-4(5H)-one,
8-((cyclopropylamino)methyl)pyrrolo[1,2-a]quinoxalin-4(5H)-one,
8-((isopropylamino)methyl)pyrrolo[1,2-a]quinoxalin-4(5H)-one,
8-(((2-phenylethyl)amino)methyl)pyrrolo[1,2-a]quinoxalin-4(5H)-one,
8-(pyrrolidin-1-ylmethyl)pyrrolo[1,2-a]quinoxalin-4(5H)-one,
8-((cyclobutylamino)methyl)pyrrolo[1,2-a]quinoxalin-4(5H)-one,
8-(morpholin-4-ylmethyl)pyrrolo[1,2-a]quinoxalin-4(5H)-one,
8-((cyclopentylamino)methyl)pyrrolo[1,2-a]quinoxalin-4(5H)-one,
8-(piperidin-1-ylmethyl)pyrrolo[1,2-a]quinoxalin-4(5H)-one,
8-((benzylamino)methyl)pyrrolo[1,2-a]quinoxalin-4(5H)-one,
7-(pyrrolidin-1-ylmethyl)imidazo[1,2-a]quinoxalin-4(5H)-one,
7-(piperidin-1-ylmethyl)imidazo[1,2-a]quinoxalin-4(5H)-one,
7-((dimethylamino)methyl)imidazo[1,2-a]quinoxalin-4(5H)-one,
7-(((cyclohexylmethyl)amino)methyl)imidazo[1,2-a]quinoxalin-4(5H)-one,
7-(morpholin-4-ylmethyl)imidazo[1,2-a]quinoxalin-4(5H)-one,
8-((dimethylamino)methyl)-5,6-dihydro-4H-pyrrolo[1,2-a][1,4]benzodiazepin-4-one,
8-(pyrrolidin-1-ylmethyl)-5,6-dihydro-4H-pyrrolo[1,2-a][1,4]benzodiazepin-4-one,
8-((isopropylamino)methyl)-5,6-dihydro-4H-pyrrolo[1,2-a][1,4]benzodiazepin-4-one,
8-((4-methylpiperazin-1-yl)methyl)-5,6-dihydro-4H-pyrrolo[1,2-a][1,4]benzodiazepin-4-one,
8-(((2-ethoxyethyl)(methyl)amino)methyl)-5,6-dihydro-4H-pyrrolo[1,2-a][1,4]benzodiazepin-4-one,
8-(((cyclohexylmethyl)amino)methyl)-5,6-dihydro-4H-pyrrolo[1,2-a][1,4]benzodiazepin4-one,
8-((benzylamino)methyl)-5,6-dihydro-4H-pyrrolo[1,2-a][1,4]benzodiazepin-4-one,
8-((cyclopentylamino)methyl)-5,6-dihydro-4H-pyrrolo[1,2-a][1,4]benzodiazepin-4-one,
3-(pyrrolidin-1-ylmethyl)-7,8,9,10-tetrahydro-5H-pyrido[1,2-a]quinoxalin-6(6aH)-one,
3-[(dimethylamino)methyl]-7,8,9,10-tetrahydro-5H-pyrido[1,2-a]quinoxalin-6(6aH)-one,
3-[(cyclohexylamino)methyl]-7,8,9,10-tetrahydro-5H-pyrido[1,2-a]quinoxalin-6(6aH)-one,
3-(piperidin-1-ylmethyl)-7,8,9,10-tetrahydro-5H-pyrido[1,2-a]quinoxalin-6(6aH)-one,
3-[(isopropylamino)methyl]-7,8,9,10-tetrahydro-5H-pyrido[1,2-a]quinoxalin-6(6aH)-one,
3-{[ethyl(methyl)amino]methyl}-7,8,9,10-tetrahydro-5H-pyrido[1,2-a]quinoxalin-6(6aH)-one,
3-{[cyclohexyl(methyl)amino]methyl}-7,8,9,10-tetrahydro-5H-pyrido[1,2-a]quinoxalin-6(6aH)-one,
3-{[isopropyl(methyl)amino]methyl}-7,8,9,10-tetrahydro-5H-pyrido[1,2-a]quinoxalin-6(6aH)-one,
3-[(4-methylpiperazin-1-yl)methyl]-7,8,9,10-tetrahydro-5H-pyrido[1,2-a]quinoxalin-6(6aH)-one,
7-(pyrrolidin-1-ylmethyl)-1,2,3,3a-tetrahydropyrrolo[1,2-a]quinoxalin-4(5H)-one,
7-[(dimethylamino)methyl]-1,2,3,3a-tetrahydropyrrolo[1,2-a]quinoxalin-4(5H)-one,
7-(piperidin-1-ylmethyl)-1,2,3,3a-tetrahydropyrrolo[1,2-a]quinoxalin-4(5H)-one,
7-{[ethyl(methyl)amino]methyl}-1,2,3,3a-tetrahydropyrrolo[1,2-a]quinoxalin-4(5H)-one,
7-{[cyclohexyl(methyl)amino]methyl}-1,2,3,3a-tetrahydropyrrolo[1,2-a]quinoxalin-4(5H)-one,
7-[(4-methylpiperazin-1-yl)methyl]-1,2,3,3a-tetrahydropyrrolo[1,2-a]quinoxalin-4(5H)-one, 7-{[benzyl(methyl)amino]methyl}-1,2,3,3a-tetrahydropyrrolo[1,2-a]quinoxalin-4(5H)-one,
7-{[isopropyl(methyl)amino]methyl}-1,2,3,3a-tetrahydropyrrolo[1,2-a]quinoxalin-4(5H)-one,
N-cyclopropyl-N-[(4-oxo4,5-dihydropyrrolo[1,2-a]quinoxalin-8-yl)methyl]methanesulfonamide
7-[(2-oxopyrrolidin-1-yl)methyl]pyrrolo[1,2-a]quinoxalin-4(5H)-one,
N-cyclobutyl-N-[(4-oxo-4,5-dihydropyrrolo[1,2-a]quinoxalin-8-yl)methyl]ethanesulfonamide,
N-isopropyl-N-[(4-oxo-4,5-dihydropyrrolo[1,2-a]quinoxalin-8-yl)methyl]benzenesulfonamide,
N-cyclobutyl-N-[(4-oxo-4,5-dihydropyrrolo[1,2-a]quinoxalin-7-yl)methyl]acetamide,
N-cyclopropyl-N-[(4-oxo4,5-dihydropyrrolo[1,2-a]quinoxalin-7-yl)methyl]methanesulfonamide,
8-(piperidin-1-ylmethyl)-5,6-dihydro-4H-pyrrolo[1,2-a][1,4]benzodiazepin-4-one,
8-[(cyclohexylamino)methyl]-5,6-dihydro-4H-pyrrolo[1,2-a][1,4]benzodiazepin-4-one,
methyl N-[(4-oxo4,5-dihydropyrrolo[1,2-a]quinoxalin-7-yl)methyl]glycinate,
N-[(4-oxo-4,5-dihydropyrrolo[1,2-a]quinoxalin-7-yl)methyl]glycine,
4-oxo-N-(2-pyrrolidin-1-ylethyl)-4,5-dihydropyrrolo[1,2-a]quinoxaline-7-carboxamide,
7-{[(2-pyrrolidin-1-ylethyl)amino]methyl}pyrrolo[1,2-a]quinoxalin-4(5H)-one,
N-(3-morpholin4-ylpropyl)-4-oxo-4,5-dihydropyrrolo[1,2-a]quinoxaline-7-carboxamide,
N-(2-morpholino-2-oxoethyl)-4-oxo4,5-dihydropyrrolo[1,2-a]quinoxaline-7-carboxamide,
7-({[2-(dimethylamino)ethyl]amino}methyl)pyrrolo[1,2-a]quinoxalin-4(5H)-one,
N-[3-(4-methylpiperazin-1-yl)propyl]-4-oxo-4,5-dihydropyrrolo[1,2-a]quinoxaline-7-carboxamide,
7-{[(3-morpholin-4-ylpropyl)amino]methyl}pyrrolo[1,2-a]quinoxalin-4(5H)-one,
2-(dimethylamino)ethyl]-4-oxo-4,5-dihydropyrrolo[1,2-a]quinoxaline-7-carboxamide,
7-{[(3-piperidin-1-ylpropyl)amino]methyl}pyrrolo[1,2-a]quinoxalin-4(5H)-one,
4-oxo-N-(3-piperidin-1-ylpropyl)-4,5-dihydropyrrolo[1,2-a]quinoxaline-7-carboxamide,
7-{[(2-piperidin-1-ylethyl)amino]methyl}pyrrolo(1,2-a]quinoxalin-4(5H)-one,
7-({[4-(dimethylamino)cyclohexyl]amino}methyl)pyrrolo[1,2-a]quinoxalin-4(5H)-one,
4-oxo-N-(2-oxo-2-(pyrrolidin-1-yl)ethyl)-4,5-dihydropyrrolo[1,2-a]quinoxaline-7-carboxamide,
N-[4-(dimethylamino)cyclohexyl]-4-oxo-4,5-dihydropyrrolo[1,2-a]quinoxaline-7-carboxamide,
4-oxo-N-[3-(piperidin-1-ylsulfonyl)phenyl]-4,5-dihydropyrrolo[1,2-a]quinoxaline-7-carboxamide,
7-((2-oxo-2-(pyrrolidin-1-yl)ethylamino)methyl)pyrrolo[1,2-a]quinoxalin-4(5H)-one,
4-oxo-N-(pyridin-4-ylmethyl)-4,5-dihydropyrrolo[1,2-a]quinoxaline-7-carboxamide,
4-oxo-N-(2-thiomorpholin-4-ylethyl)-4,5-dihydropyrrolo[1,2-a]quinoxaline-7-carboxamide,
N,N-dimethyl-4-oxo-4,5-dihydropyrrolo[1,2-a]quinoxaline-7-carboxamide,
N-(1-ethylpiperidin-3-yl)-4-oxo-4,5-dihydropyrrolo[1,2-a]quinoxaline-7-carboxamide,
4-oxo-N-(4-phenylbutyl)-4,5-dihydropyrrolo[1,2-a]quinoxaline-7-carboxamide,
7-(pyrrolidin-1-ylcarbonyl)pyrrolo[1,2-a]quinoxalin-4(5H)-one,
N-[4-4-benzylpiperazin-1-yl)phenyl]-4-oxo-4,5-dihydropyrrolo[1,2-a]quinoxaline-7-carboxamide,
4-oxo-N-1,3-thiazol-2-yl-4,5-dihydropyrrolo[1,2-a]quinoxaline-7-carboxamide,
7-(piperidin-1-ylcarbonyl)pyrrolo[1,2-a]quinoxalin-4(5H)-one,
7-[(4-aminopiperidin-1-yl)methyl]pyrrolo[1,2-a]quinoxalin-4(51H)-one,
7-[(4-aminopiperidin-1-yl)carbonyl]pyrrolo[1,2-a]quinoxalin-4(5H)-one,
7-(1,4-diazepan-1-ylcarbonyl)pyrrolo[1,2-a]quinoxalin-4(5H)-one,
6-(pyrrolidin-1-ylcarbonyl)pyrrolo[1,2-a]quinoxalin-4(5H)-one,
and therapeutically salts, prodrugs, esters, amides, salts of prodrugs, salts of esters and salts of amides thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends.

It is also meant to be understood that a specific embodiment of a variable moiety may be the same or different as another specific embodiment having the same identifier.

Abbreviations which have been used in the descriptions of the schemes and the examples that follow are: "DMF" for N,N-dimethylformamide, "DMSO" for dimethylsulfoxide, "HATU" for O-(7-azabenzotriazol-1-yl)-N,N,N',N'-tetramethyluronium hexafluorophosphate, "TFA" for trifluoroacetic acid, "THF" for tetrahydrofuran, and "Pd/C" for Palladium/carbon.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkynyl," as used herein, means monovalent, straight or branched chain hydrocarbon moieties having one or more than one carbon-carbon triple bonds, such as $C_2$-alkynyl. $C_3$-alkynyl, $C_4$-alkynyl, $C_5$-alkynyl, $C_6$-alkynyl and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon- nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, $C(O)NH_2$, OH or SH moieties may have attached thereto prodrug-forming moieties. The prodrug-forming moieties are removed by metabolic processes and release the compounds having the freed NH, C(O)H, C(O)OH, $C(O)NH_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases caused or exacerbated by unregulated or overexpressed poly(ADP-ribose)polymerase.

Certain precursor compounds of compounds having Formula I may be metabolized in vitro or in vivo to form compounds having Formula I and may thereby also have utility for treating diseases caused or exacerbated by unregulared or overexpressed poly(ADP-ribose)polymerase.

Compounds having Formula I may exist as acid addition salts, basic addition salts or zvitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide, or phosphate of cations such as lithium, sodium, potassium, calcium and magnesium.

Compounds having Formula I may be administered, for example, bucally, ophthalmically, orally, osmotically, parenterally (intramuscularly, intraperintoneally intrastemally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of submultiples thereof.

Compounds having Formula I may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}C$), hydrogen (i.e. $^{3}H$), nitrogen (i.e. $^{15}N$), phosphorus (i.e. $^{32}P$), sulfur (i.e. $^{35}S$), iodide (i.e. $^{125}I$) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and ureteural stents, each of which may be used in areas such as, but not limited to, the vasculature for introduction of a compound having Formula I into selected tissues or organs in the body. One measure of the effectivness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3- butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof Excipients for preparation of compositions comprising a compound having Formula I to be administered rectally or vaginally include, for example, cocoa butter, polyethylene glycol, wax and mixtures thereof.

Compounds having formula I are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her21gG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCI, PU-3, radicicol, SNX-2112, STA-9090 VER49009 and the like.

MEK inhibitors include ARRY-142886, ARRY438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, ribavirin, traipine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGELφ (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE® (Interferon alfa), BAM-002, BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (BCG Live (Intravesical)), ubenimex, VIRULIZIN® (biological response modifier obtained from bovine bile), Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I may be combined with other chemptherapeutic agents such as ABRAXANE™ (ABI-007), ABT-100 (famesyl transferase inhibitor), ADVEXIN® (Ad5CMV-p53), ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane(1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheR$^{1.4}$ toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafamib, 5,10-methylenetetrahydrofolate, miltefosine(hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is expected that compounds having formula I would also inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. September 2000; 110(3): 584-90; Blood February 2000 15;95(4): 1283-92; and New England Journal of Medicine September 2004; 351(14): 1409-1418).

Inhibition of PARP

Nicotinamide[2,5',8-3H]adenine dinucleotide and strepavidin SPA beads were purchased from Amersham Biosiences (Buckinghamshire, U.K.). Recombinant Human Poly(ADP-ribose) Polymerase (PARP), purified from *E. coli* and 6-Biotin-17-NAD$^+$, were purchased from Trevigen (Gaithersburg, Md.). NAD$^+$, histone, aminobenzamide, 3-amino benzamide and Calf Thymus DNA (dcDNA) were purchased from Sigma (St. Louis, Mo.). Stem loop oligonucleotide containing MCAT sequence was obtained from Qiagen (Valencia, Calif.). The oligos were dissolved to 1 mM in annealing buffer containing 10 mM Tris HCl pH 7.5, 1 mM EDTA, and 50 mM NaCl, incubated for 5 minutes at 95° C., and annealed at 45° C. for 45 minutes. Histone H1 (95% electrophoretically pure) was purchased from Roche (Indianapolis, Ind.). Biotinylated histone H1 was prepared by treating the protein with Sulfo-NHS-LC-Biotin from Pierce (Rockford, Ill.). The biotinylation reaction was conducted by slowly and intermittently adding 3 equivalents of 10 mM Sulfo-NHS-LC-Biotin to 100 µM Histone H1 in phosphate-buffered saline, pH 7.5, at 4° C. with gentle vortexing over 1 minute followed by subsequent 4° C. incubation for 1 hour. Streptavidin coated (FLASHPLATE PLUS®) microplates were purchased from Perkin Elmer (Waltham, Mass.).

PARP1 assay was conducted in PARP assay buffer containing 50 mM Tris pH 8.0, 1 mM DTT, 4 mM MgCl$_2$. PARP reactions contained 1.5 µM [$^3$H]-NAD$^+$ (1.6 uCi/mmol), 200 nM biotinylated histone H1, 200 nM slDNA, and 1 nM PARP enzyme. Auto reactions utilizing SPA bead-based detection were carried out in 100 µL volumes in white 96 well plates. Reactions were initiated by adding 50 µl of 2× NAD$^+$ substrate mixture to 50 µL of 2× enzyme mixture containing PARP and DNA. These reactions were terminated by the addition of 150 µL of 1.5 mM benzamide (~1000-fold over its IC50). 170 µL of the stopped reaction mixtures were transferred to streptavidin FLASHPLATE PLUS®, incubated for 1 hour, and counted using a TOPCOUNT® microplate scintillation counter from Perkin Elmer (Waltham, Mass.). The EC$_{50s}$ for exemplified compounds of this invention are provided in Table 1.

Cellular PARP Assay:

C41 cells were treated with a compound of this invention for 30 minutes in 96 well plate. PARP was then activated by damaging DNA with 1 mM $H_2O_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-TWEEN20® (Sigma, St. Louis, Mo.) (0.05%) (blocking solution) for 30 minutes at room temperature. The cells were incubated with anti-PAR antibody 10H (1:50) in Blocking solution at 37° C. for 60 minutes followed by washing with PBS-TWEEN20® 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-TWEEN20® 5 times, the analysis was performed using an FMAX FLUORESCENCE MICROPLATE READER® (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of this invention penetrate cell membranes and inhibit PARP in intact cells. The $K_i$ data (nM) were determined from inhibition curves at various substrate concentrations and are shown in TABLE 1.

TABLE 1

Inhibition of PARP by Representative Compounds Having Formula I

| Example | PARP-1 ($K_i$, nM) | Cell, $EC_{50}$, nM |
|---|---|---|
| 1 | 474 | |
| 2 | 91 | |
| 3 | 83 | |
| 4 | 179 | |
| 5 | 49 | 39 |
| 6 | 11 | 9.6 |
| 7 | 6 | 5.4 |
| 8 | 99 | |
| 9 | 206 | |
| 10 | 26 | 12 |
| 11 | 127 | |
| 12 | 32 | 13 |
| 13 | 44 | 37 |
| 14 | 98 | |
| 15 | 48 | 29 |
| 16 | 51 | |
| 17 | 130 | |
| 18 | 79 | |
| 19 | 47 | 31 |
| 20 | 131 | |
| 21 | 280 | |
| 22 | 330 | |
| 23 | 519 | |
| 24 | 5180 | |
| 25 | 2850 | |
| 26 | 492 | |
| 27 | 1120 | |
| 28 | 1470 | |
| 29 | 1500 | |
| 30 | 2650 | |
| 31 | 1490 | |
| 32 | 809 | |
| 33 | 554 | |
| 34 | 114 | |
| 35 | 63 | 48 |
| 36 | 3490 | |
| 37 | 98 | |
| 38 | 340 | |
| 39 | 71 | |
| 40 | 1500 | |
| 41 | 284 | |
| 42 | 7790 | |
| 43 | 97 | |
| 44 | 60 | 143 |
| 45 | 146 | |
| 46 | 130 | |
| 47 | 2160 | |
| 48 | >9500 | |
| 49 | 1350 | |
| 50 | 1960 | |
| 51 | 779 | |
| 52 | 698 | |
| 53 | 917 | |
| 54 | 635 | |
| 55 | 1500 | |
| 56 | 909 | |
| 57 | 1140 | |
| 58 | 1440 | |
| 59 | 534 | |
| 60 | 318 | |
| 61 | 134 | |
| 62 | 38 | 106 |
| 63 | 211 | |
| 64 | 369 | |
| 65 | 427 | |
| 66 | 23 | 32 |
| 67 | 356 | |
| 68 | 1630 | |
| 69 | 129 | |
| 70 | 139 | |
| 71 | 182 | |
| 72 | 163 | |
| 73 | 874 | |
| 74 | 776 | |
| 75 | 1640 | |
| 76 | 149 | |
| 77 | 42 | 797 |
| 78 | 86 | |
| 79 | 615 | |
| 80 | 113 | |
| 81 | 94 | |
| 82 | 1540 | |
| 83 | 58 | |
| 84 | 98 | |
| 85 | 16 | 23 |
| 86 | 35 | 204 |
| 87 | 77 | |
| 88 | 8690 | |

As PARP inhibitors, the compounds of this invention have numerous therapeutic applications related to ischemia reperfusion injury, inflammatory diseases, degenerative diseases, protection from adverse effects of cytotoxic compounds, and potentiation of cytotoxic cancer therapy. In particular, compounds of this invention potentiate radiation and chemotherapy by increasing cell death of cancer cells, limiting tumor growth, decreasing metastasis, and prolonging the survival of tumor-bearing mammals. Compounds having fomula I can treat leukemia, colon cancer, glioblastomas, lymphomas, melanomas, carcinomas of the breast, and cervical carcinomas.

Other therapeutic applications include retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin Compounds of Formula I 1. In one embodiment of Formula (I)

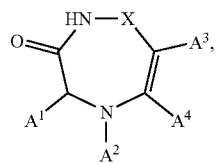

X is a bond or CH$_2$;

A$^1$ and A$^2$, together with the atoms to which they are attached, are pyrrole, imidazole, piperidine, or pyrrolidine;

A$^3$ and A$^4$, together with the atoms to which they are attached, are benzene which is substituted with R$^1$, OR$^1$, SR$^1$, S(O)R$^1$, SO$_2$R$^1$, NH$_2$, NHR$^1$, N(R$^1$)$_2$, C(O)R$^1$, C(O)NH$_2$, C(O)NHR$^1$, C(O)N(R$^1$)$_2$, NHC(O)R$^1$, NR$^1$C(O)R$^1$, NHSO$_2$R$^1$, NR$^1$SO$_2$R$^1$, NHC(O)OR$^1$, NR$^1$C(O)OR$^1$, SO$_2$NH$_2$, SO$_2$NHR$^1$, SO$_2$N(R$^1$)$_2$, NHC(O)NH$_2$, NHC(O)NHR$^1$, NHC(O)N(R$^1$)$_2$, OH, C(O)OH, CN, CF$_3$, OCF$_3$, CF$_2$CF$_3$, F, Cl, Br or I;

R$^1$ is R$^2$, R$^3$, R$^4$ or R$^5$;

R$^2$ is phenyl which is unfused or fused with benzene, heteroarene, cycloalkane, cycloalkene, heterocycloalkane or heterocycloalkene;

R$^3$ is heteroarene which is unfused or fused with benzene, heteroarene, cycloalkane, cycloalkene, heterocycloalkane or heterocycloalkene;

R$^4$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R$^5$ is alkyl, alkenyl or alkynyl, each of which is unsubstituted or substituted with one or two of independently selected R$^6$, C(O)OH, NH$_2$, NHR$^6$, N(R$^6$)$_2$, C(O)R$^6$, C(O)NH$_2$, C(O)NHR$^6$, C(O)N(R$^6$)$_2$, NHC(O)R$^6$, NR$^6$C(O)R$^6$, NR$^6$S(O)$_2$R$^6$, F, Cl, Br or I;

R$^6$ is R$^7$, R$^8$, R$^9$ or R$^{10}$;

R$^7$ is phenyl which is unfused or fused with benzene, heteroarene, cycloalkane, cycloalkene, heterocycloalkane or heterocycloalkene;

R$^8$ is heteroarene which is unfused or fused with benzene, heteroarene, cycloalkane, cycloalkene, heterocycloalkane or heterocycloalkene;

R$^9$ is cycloalkyl, cycloalkenyl, heterocycloalkyl or heterocycloalkenyl, each of which is unfised or fused with benzene, heteroarene, cycloalkane, cycloalkene, heterocycloalkane or heterocycloalkene;

R$^{10}$ is alkyl, alkenyl or alkynyl, each of which is unsubstituted or substituted with one or two of independently selected R$^{11}$, C(O)OH, NH$_2$, NHR$^{11}$, N(R$^{11}$)$_2$, C(O)R$^{11}$, C(O)OR$^{11}$, C(O)NH$_2$, C(O)NHR$^{11}$, C(O)N(R$^{11}$)$_2$, NHC(O)R$^{11}$, NR$^{11}$C(O)R$^{11}$, F, Cl, Br or I;

R$^{11}$ is R$^{12}$, R$^{13}$, R$^{14}$ or R$^{14A}$;

R$^{12}$ is phenyl which is unfused or fused with benzene, heteroarene, cycloalkane, cycloalkene, heterocycloalkane or heterocycloalkene;

R$^{13}$ is heteroarene which is unfused or fused with benzene, heteroarene, cycloalkane, cycloalkene, heterocycloalkane or heterocycloalkene;

R$^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

R$^{14A}$ is alkyl, alkenyl, or alkynyl;

wherein the moieties represented by A$^1$ and A$^2$ and A$^2$ and A$^3$ and the moieties represented by R$^2$, R$^3$, R$^4$, R$^7$, R$^8$, R$^9$, R$^{12}$, R$^{13}$ and R$^{14}$ are independently unsubstituted or further unsubstituted or independently substituted or further substituted with R$^{15}$, OR$^{15}$, SR$^{15}$, S(O)R$^{15}$, SO$_2$R$^{15}$, NH$_2$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NR$^{15}$SO$_2$R$^{15}$, NHC(O)OR$^{15}$, NR$^{15}$C(O)OR$^{15}$, SO$_2$NH$_2$, SO$_2$NHR$^{15}$, SO$_2$N(R$^{15}$)$_2$, NHC(O)NH$_2$, NHC(O)NHR$^{15}$, NHC(O)N(R$^{15}$)$_2$, NR$^{15}$C(O)N(R$^{15}$)$_2$, OH, (O), C(O)OH, CN, CF$_3$, OCF$_3$, CF$_2$CF$_3$, F, Cl, Br or I;

wherein R$^{15}$ is R$^{16}$, R$^{17}$, R$^{18}$ or R$^{19}$;

R$^{16}$ is phenyl which is unfused or fused with benzene;

R$^{17}$ is heteroaryl which is unfused or fused with benzene;

R$^{18}$ is cycloalkyl, cycloalkenyl, heterocycloalkyl or heterocycloalkenyl, each of which is unfused or fused with benzene;

R$^{19}$ is alkyl, alkenyl or alkynyl, each of which is unsubstituted or substituted with one or two of independently selected R$^{20}$, C(O)OH, NH$_2$, NHR$^{20}$ or N(R$^{20}$)$_2$, C(O)R$^{20}$, C(O)NH$_2$, C(O)NHR$^{20}$, C(O)N(R$^{20}$)$_2$, NHC(O)R$^{20}$, NR$^{20}$C(O)R$^{20}$, F, Cl, Br or I;

R$^{20}$ is R$^{21}$ or R$^{21A}$;

R$^{21}$ is phenyl, heteroaryl, cycloalkyl, cycloalkenyl, heterocycloalkyl, or heterocycloalkenyl;

R$^{21A}$ is alkyl, alkenyl or alkynyl, each of which is unsubstituted or substituted with one or two of independently selected R$^{22}$, C(O)OH, NH$_2$, NHR$^{22}$ or N(R$^{22}$)$_2$, C(O)R$^{22}$, C(O)NH$_2$, C(O)NHR$^{22}$, C(O)N(R$^{22}$)$_2$, NHC(O)R$^{22}$, NR$^{22}$C(O)R$^{22}$, F, Cl, Br or I;

R$^{22}$ is phenyl, heteroaryl, cycloalkyl, cycloalkenyl, heterocycloalkyl or heterocycloalkenyl;

wherein the moieties represented by R$^{16}$, R$^{17}$, R$^{18}$, R$^{21}$, and R$^{22}$ are independently unsubstituted or further unsubstituted or independently substituted or further substituted with R$^{23}$, OR$^{23}$, SR$^{23}$, S(O)R$^{23}$, SO$_2$R$^{23}$, NH$_2$, NHR$^{23}$, N(R$^{23}$)$_2$, C(O)R$^{23}$, C(O)NH$_2$, C(O)NHR$^{23}$, C(O)N(R$^{23}$)$_2$, NHC(O)R$^{23}$, NR$^{23}$C(O)R$^{23}$, NHSO$_2$R$^{23}$, NR$^{23}$SO$_2$R$^{23}$, NHC(O)OR$^{23}$, NR$^{23}$C(O)OR$^{23}$, SO$_2$NH$_2$, SO$_2$NHR$^{23}$, SO$_2$N(R$^{23}$)$_2$, NHC(O)NH$_2$, NHC(O)NHR$^{23}$, NHC(O)N(R$^{23}$)$_2$, NR$^{23}$C(O)N(R$^{23}$)$_2$, OH, (O), C(O)OH, CN, CF$_3$, OCF$_3$, CF$_2$CF$_3$, F, Cl, Br or I;

wherein R$^{23}$ is R$^{24}$, R$^{25}$, R$^{26}$ or R$^{27}$;

R$^{24}$ is phenyl which is unfused or fused with benzene;

R$^{25}$ is heteroaryl which is unfused or fused with benzene;

R$^{26}$ is cycloalkyl, cycloalkenyl, heterocycloalkyl or heterocycloalkenyl, each of which is unfused or fused with benzene;

R$^{27}$ is alkyl, alkenyl or alkynyl, each of which is unsubstituted or substituted with one or two of independently selected R$^{28}$, C(O)OH, NH$_2$, NHR$^{28}$ or N(R$^{28}$)$_2$, C(O)R$^{28}$, C(O)NH$_2$, C(O)NHR$^{28}$, C(O)N(R$^{28}$)$_2$, NHC(O)R$^{28}$, NR$^{28}$C(O)R$^{28}$, F, Cl, Br or I;

R$^{28}$ is phenyl, heteroaryl, cycloalkyl, cycloalkenyl, heterocycloalkyl, heterocycloalkenyl or R$^{29}$;

R$^{29}$ is alkyl, alkenyl or alkynyl, each of which is unsubstituted or substituted with one or two of independently selected $R^{30}$, C(O)OH, $NH_2$, $NHR^{30}$ or $N(R^{30})_2$, $C(O)R^{30}$, $C(O)NH_2$, $C(O)NHR^{30}$, $C(O)N(R^{30})_2$, $NHC(O)R^{30}$, $NR^{30}C(O)R^{30}$, F, Cl, Br or I; and $R^{30}$ is phenyl, heteroaryl, cycloalkyl, cycloalkenyl, heterocycloalkyl or heterocycloalkenyl.

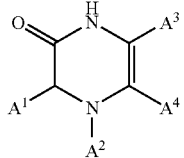

IA

2. In another embodiment of Formula (I), X is a bond as in Formula (IA), and wherein $A^1$, $A^2$, $A^3$, $A^4$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

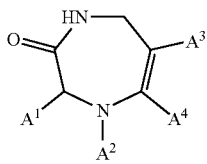

IB

3. In another embodiment of Formula (I), X is $CH_2$ as in Formula (IB), and wherein $A^1$, $A^2$, $A^3$, $A^4$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

4. In another embodiment of Formula (I), $A^3$ and $A^4$, together with the atoms to which they are attached, are benzene which is substituted with $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$; and wherein X, $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

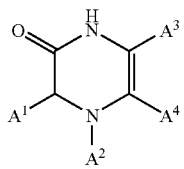

IA

5. In another embodiment of Formula (I), X is a bond as in Formula (IA), $A^3$ and $A^4$, together with the atoms to which they are attached, are benzene which is substituted with $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$; and wherein $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

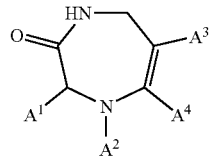

IB

6. In another embodiment of Formula (I), X is $CH_2$ as in Formula (IB), $A^3$ and $A^4$, together with the atoms to which they are attached, are benzene which is substituted with $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$; and wherein $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

7. In another embodiment of Formula (I), $A^3$ and $A^4$, together with the atoms to which they are attached, are benzene which is substituted with $R^1$, $C(O)R^1$, $C(O)NHR^1$, or $C(O)N(R^1)_2$; and wherein X, $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

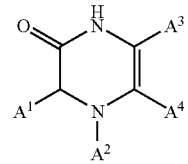

IA

8. In another embodiment of Formula (I), X is a bond as in Formula (IA), $A^3$ and $A^4$, together with the atoms to which they are attached, are benzene which is substituted with $R^1$, $C(O)R^1$, $C(O)NHR^1$, or $C(O)N(R^1)_2$; and wherein $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

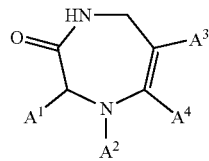

IB

9. In another embodiment of Formula (I), X is $CH_2$ as in Formula (IB), $A^3$ and $A^4$, together with the atoms to which they are attached, are benzene which is substituted with $R^1$, $C(O)R^1$, $C(O)NHR^1$, or $C(O)N(R^1)_2$; and wherein $A^1$, $A^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

10. In another embodiment of Formula (I), $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein X, $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

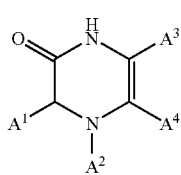

IA

11. In another embodiment of Formula (I), X is a bond as in Formula (IA); $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

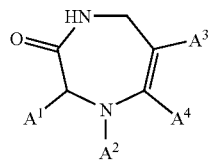

IB

12. In another embodiment of Formula (I), X is a $CH_2$; as in Formula (IB); $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

13. In another embodiment of Formula (I), $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein X, $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

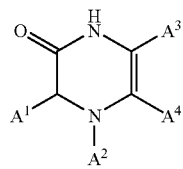

IA

14. In another embodiment of Formula (I), X is a bond as in Formula (IA); $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

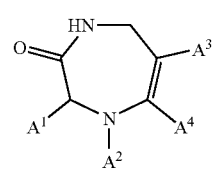

IB

15. In another embodiment of Formula (I), X is $CH_2$ as in Formula (IB); $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $A^1$, $A^2$, $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

16. In another embodiment of Formula (I), X is a bond or $CH_2$; $A^1$ and $A^2$, together with the atoms to which they are attached, are pyrrole, imidazole, piperidine, or pyrrolidine; $A^3$ and $A^4$, together with the atoms to which they are attached, are benzene which is substituted with $R^1$, $C(O)R^1$, $C(O)NHR^1$, or $C(O)N(R^1)_2$; $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, C(O)OH, N($R^{11}$)$_2$, C(O)$R^{11}$, or C(O)O$R^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, SO$_2$$R^{15}$, NH$_2$, N($R^{15}$)$_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

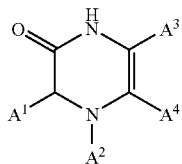

IA

17. In another embodiment of Formula (I), X is a bond as in Formula (IA); $A^1$ and $A^2$, together with the atoms to which they are attached, are pyrrole, imidazole, piperidine, or pyrrolidine; $A^3$ and $A^4$, together with the atoms to which they are attached, are benzene which is substituted with $R^1$, C(O)$R^1$, C(O)NH$R^1$, or C(O)N($R^1$)$_2$; $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, NH$R^6$, N($R^6$)$_2$, C(O)$R^6$, NR$^6$C(O)$R^6$ or NR$^6$S(O)$_2$$R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, C(O)OH, N($R^{11}$)$_2$, C(O)$R^{11}$, or C(O)O$R^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, SO$_2$$R^{15}$, NH$_2$, N($R^{15}$)$_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

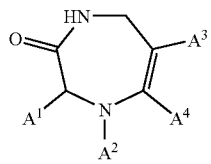

IB

18. In another embodiment of Formula (I), X is CH$_2$ as in Formula (IB); $A^1$ and $A^2$, together with the atoms to which they are attached, are pyrrole, imidazole, piperidine, or pyrrolidine; $A^3$ and $A^4$, together with the atoms to which they are attached, are benzene which is substituted with $R^1$, C(O)$R^1$, C(O)NH$R^1$, or C(O)N($R^1$)$_2$; $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, NH$R^6$, N($R^6$)$_2$, C(O)$R^6$, NR$^6$C(O)$R^6$, or NR$^6$S(O)$_2$$R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, C(O)OH, N($R^{11}$)$_2$, C(O)$R^{11}$, or C(O)O$R^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, SO$_2$$R^{15}$, NH$_2$, N($R^{15}$)$_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

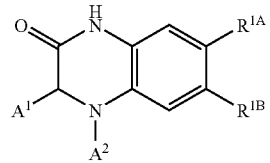

II

19. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$, and one of $R^{1A}$ and $R^{1B}$ is H, and the other is $R^1$, O$R^1$, S$R^1$, S(O)$R^1$, SO$_2$$R^1$, NH$_2$, NH$R^1$, N($R^1$)$_2$, C(O)$R^1$, C(O)NH$_2$, C(O)NH$R^1$, C(O)N($R^1$)$_2$, NHC(O)$R^1$, N$R^1$C(O)$R^1$, NHSO$_2$$R^1$, N$R^1$SO$_2$$R^1$, NHC(O)O$R^1$, N$R^1$C(O)O$R^1$, SO$_2$NH$_2$, SO$_2$NH$R^1$, SO$_2$N($R^1$)$_2$, NHC(O)NH$_2$, NHC(O)NH$R^1$, NHC(O)N($R^1$)$_2$, OH, C(O)OH, CN, CF$_3$, OCF$_3$, CF$_2$CF$_3$, F, Cl, Br or I as in Formula (II); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

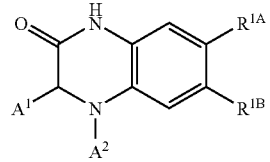

II

20. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$, and one of $R^{1A}$ and $R^{1B}$ is H, and the other is $R^1$, O$R^1$, S$R^1$, C(O)$R^1$, C(O)NH$_2$, C(O)NH$R^1$, C(O)N($R^1$)$_2$, NHC(O)$R^1$, or N$R^1$C(O)$R^1$ as in Formula (II); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

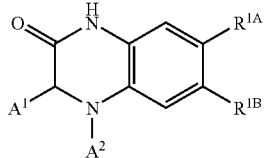

21. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (II); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

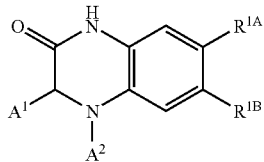

22. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (II); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

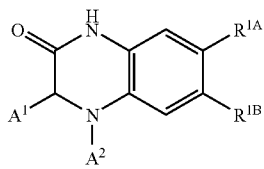

23. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (II); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

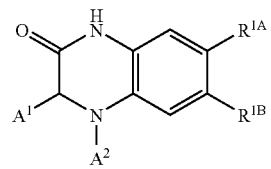

24. In another embodiment of Formula (I), X is a bond, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (II); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

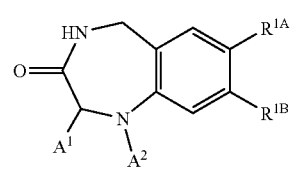

25. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, $C(O)OH$, CN, $CF_3$, $OCF_3$, $CF_2CF_3$, F, Cl, Br or I as in Formula (III); wherein $R^1$, $R^2$, $R^3$, R4, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

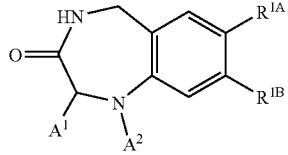
III

26. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (III); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

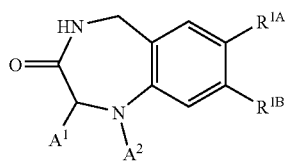
III

27. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (III); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

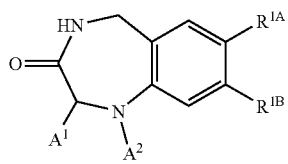
III

28. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (III); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

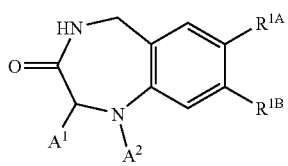
III

29. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (III); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

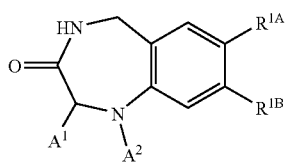
III

30. In another embodiment of Formula (I), X is a $CH_2$, and $A^1$ and $A^2$, together with the atoms to which they are attached are pyrrole, imidazole, piperidine, or pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (III); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

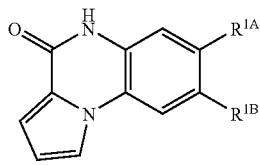

31. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I as in Formula (IV); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

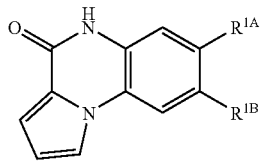

32. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (IV); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

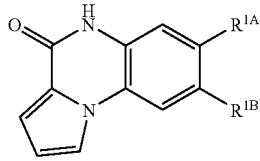

33. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (IV); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

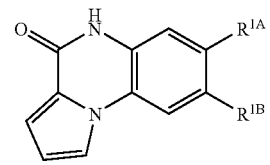

34. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (IV); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

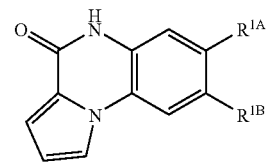

35. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$. $C(O)R^1$, $C(O)NHR^1$, or $C(O)N(R^1)_2$ as in Formula (IV); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

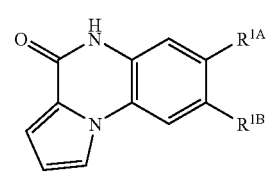

36. In another embodiment of Formula (I), X is a bond, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (IV); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

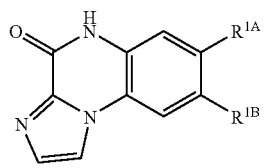

V

37. In another embodiment of Formula (I), X is a bond, and $A^1$ and $A^2$, together with the atoms to which they are attached are imidazole; $A^3$ and $A^4$ together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I as in Formula (V); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

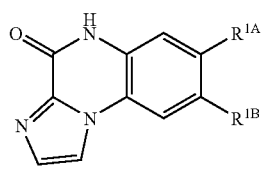

V

38. In another embodiment of Formula (I), X is a bond, and $A^1$ and $A^2$, together with the atoms to which they are attached are imidazole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (V); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

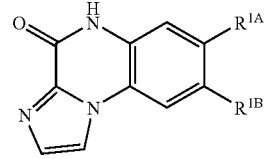

V

39. In another embodiment of Formula (I), X is a bond, and $A^1$ and $A^2$, together with the atoms to which they are attached are imidazole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (V); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

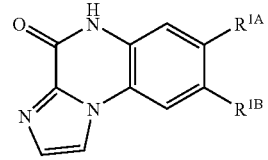

V

40. In another embodiment of Formula (I), X is a bond, and $A^1$ and $A^2$, together with the atoms to which they are attached are imidazole; $A^3$ and $A^4$ together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (V); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

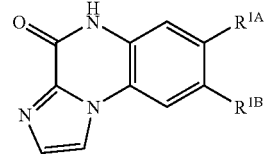

V

41. In another embodiment of Formula (I), X is a bond, and $A^1$ and $A^2$, together with the atoms to which they are attached are imidazole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (V); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; R8 is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

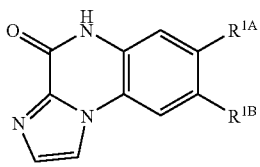

V

42. In another embodiment of Formula (I), X is a bond, and $A^1$ and $A^2$, together with the atoms to which they are attached are imidazole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (V); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

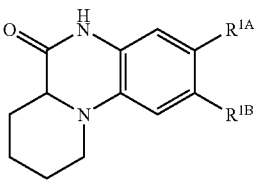

VI

43. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, C(O)OH, CN, $CF_3$, $OCF_3$, $CF_2CF_3$, F, Cl, Br or I as in Formula (VI); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

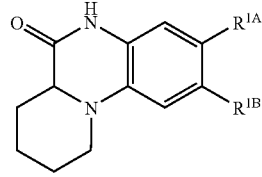

VI

44. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (VI); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

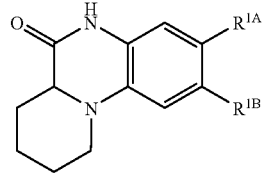

VI

45. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VI); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

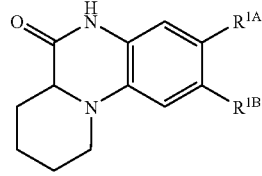

VI

46. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VI); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

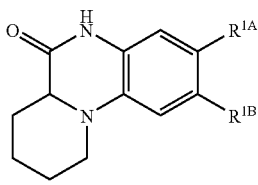

VI

47. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VI); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

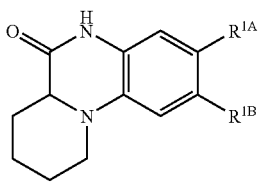

VI

48. In another embodiment of Formula (I), X is a bond, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VI); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

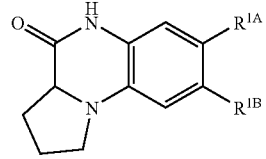

VII

49. In another embodiment of Formula (I), X is a bond, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, $C(O)OH$, CN, $CF_3$, $OCF_3$, $CF_2CF_3$, F, Cl, Br or I as in Formula (VII); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

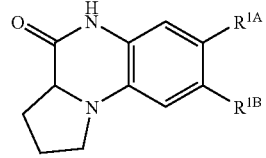

VII

50. In another embodiment of Formula (I), X is a bond, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (VII); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

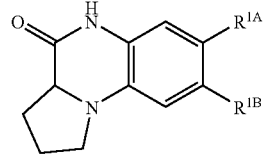

VII

51. In another embodiment of Formula (I), X is a bond, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VII); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Forrnula (I).

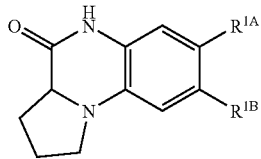

VII

52. In another embodiment of Formula (I), X is a bond, and $A^1$ and $A^2$, together with the atoms to which they are attached are pyrrolidine; $A^3$ and $A^4$ together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VII); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

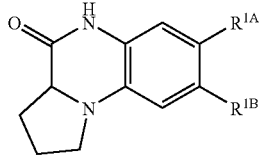

VII

53. In another embodiment of Formula (I), X is a bond, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VII); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

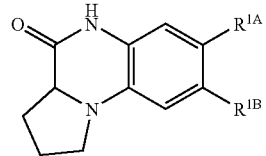

VII

54. In another embodiment of Formula (I), X is a bond, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (VII); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or $(O)$; wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

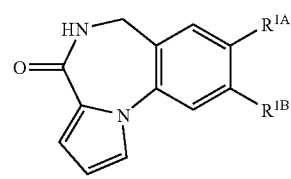

VIII

55. In another embodiment of Formula (I), X is a $CH_2$, and $A^1$ and $A^2$, together with the atoms to which they are attached are pyrrole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, $C(O)OH$, CN, $CF_3$, $OCF_3$, $CF_2CF_3$, F, Cl, Br or I as in Formula (VIII); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

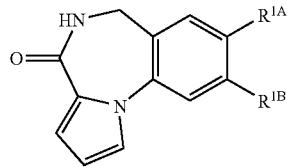

56. In another embodiment of Formula (I), X is a CH$_2$, and A$^1$ and A$^2$, together with the atoms to which they are attached are pyrrole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, OR$^1$, SR$^1$, C(O)R$^1$, C(O)NH$_2$, C(O)NHR$^1$, C(O)N(R$^1$)$_2$, NHC(O)R$^1$, or NR$^1$C(O)R$^1$ as in Formula (VIII); and wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

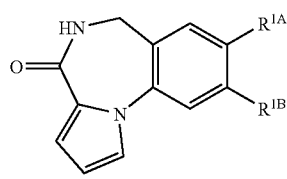

57. In another embodiment of Formula (I), X is a CH$_2$, and A$^1$ and A$^2$, together with the atoms to which they are attached are pyrrole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (VIII); and wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

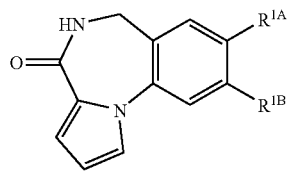

58. In another embodiment of Formula (I), X is a CH$_2$, and A$^1$ and A$^2$, together with the atoms to which they are attached are pyrrole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (VIII); and R$^1$ is R$^2$, R$^3$, R$^4$ or R$^5$; R$^2$ is phenyl; R$^3$ is heteroarene; R$^4$ is cycloalkyl, cycloalkenyl, heterocycloalkyl or heterocycloalkenyl; R$^7$ is phenyl; R$^8$ is heteroarene; R$^9$ is cycloalkyl, cycloalkenyl, heterocycloalkyl or heterocycloalkenyl; R$^{12}$ is phenyl; R$^{13}$ is heteroarene; R$^{14}$ is cycloalkyl, cycloalkenyl, heterocycloalkyl or heterocycloalkenyl; R$^{16}$ is phenyl; R$^{17}$ is heteroaryl; R$^{18}$ is cycloalkyl, cycloalkenyl, heterocycloalkyl or heterocycloalkenyl; R$^{21}$ is phenyl, heteroaryl, cycloalkyl, cycloalkenyl, heterocycloalkyl, or heterocycloalkenyl; R$^{22}$ is phenyl, heteroaryl, cycloalkyl, cycloalkenyl, heterocycloalkyl or heterocycloalkenyl; R$^{24}$ is phenyl; R$^{25}$ is heteroaryl; and R$^{26}$ is cycloalkyl, cycloalkenyl, heterocycloalkyl or heterocycloalkenyl, and wherein R$^5$, R$^6$, R$^{10}$, R$^{11}$, R$^{15}$, R$^{19}$, R$^{20}$, R$^{23}$, R$^{27}$, R$^{28}$, R$^{29}$, and R$^{30}$ are as described in Formula (I).

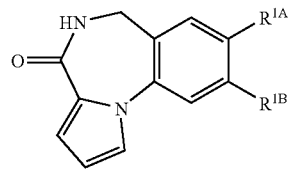

59. In another embodiment of Formula (I), X is a CH$_2$, and A$^1$ and A$^2$, together with the atoms to which they are attached are pyrrole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (VIII); and R$^1$ is R$^2$, R$^3$, R$^4$ or R$^5$; R$^2$ is phenyl; R$^3$ is heteroarene; R$^4$ is cycloalkyl or heterocycloalkyl; R$^7$ is phenyl; R$^8$ is heteroarene; R$^9$ is cycloalkyl, or heterocycloalkyl; R$^{12}$ is phenyl; R$^{14}$ is cycloalkyl, or heterocycloalkyl; R$^{18}$ is heterocycloalkyl; R$^{28}$ is phenyl; and wherein R$^5$, R$^6$, R$^{10}$, R$^{11}$, R$^{15}$, R$^{19}$, R$^{20}$, R$^{23}$, R$^{27}$, R$^{28}$, R$^{29}$, and R$^{30}$ are as described in Formula (I).

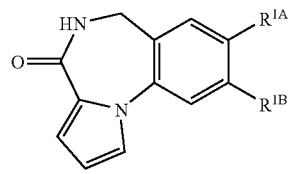

60. In another embodiment of Formula (I), X is a CH$_2$, and A$^1$ and A$^2$, together with the atoms to which they are attached are pyrrole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (VIII); and R$^1$ is R$^2$, R$^3$, R$^4$ or R$^5$; R$^2$ is phenyl; R$^3$ is heteroarene; R$^4$ is cycloalkyl or heterocycloalkyl; R$^5$ is alkyl which is unsubstituted or substituted with one or two of independently selected R$^6$, NHR$^6$, N(R$^6$)$_2$, C(O)R$^6$, NR$^6$C(O)R$^6$, or NR$^6$S(O)$_2$R$^6$; R$^6$ is R$^7$, R$^8$, R$^9$ or R$^{10}$; R$^7$ is phenyl; R$^8$ is heteroarene; R$^9$ is cycloalkyl or heterocycloalkyl; R$^{10}$ is alkyl which is unsubstituted or substituted with one or two of independently selected R$^{11}$, C(O)OH, N(R$^{11}$)$_2$, C(O)R$^{11}$, or C(O)OR$^{11}$; R$^{11}$ is R$^{12}$, R$^{14}$ or R$^{14A}$; R$^{12}$ is phenyl; R$^{14}$ is cycloalkyl or heterocycloalkyl; R$^{14A}$ is alkyl; wherein the moieties represented by R$^2$. R$^4$, and R$^9$ are independently unsubstituted independently substituted with R$^{15}$, SO$_2$R$^{15}$, NH$_2$, N(R$^{15}$)$_2$, or (O); wherein R$^{15}$ is R$^{18}$ or R$^{19}$; R$^{18}$ is heterocycloalkyl; R$^{19}$ is alkyl; wherein the moieties represented by R$^{18}$ are independently unsubstituted or independently substituted with R$^{23}$; wherein R$^{23}$ is R$^{27}$; R$^{27}$ is alkyl each of which is substituted with R$^{28}$; and R$^{28}$ is phenyl.

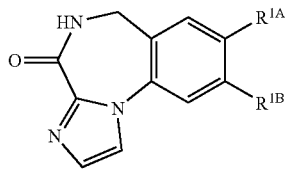

61. In another embodiment of Formula (I), X is a CH$_2$, and A$^1$ and A$^2$, together with the atoms to which they are attached are imidazole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, OR$^1$, SR$^1$, S(O)R$^1$, SO$_2$R$^1$, NH$_2$, NHR$^1$, N(R$^1$)$_2$, C(O)R$^1$, C(O)NH$_2$, C(O)NHR$^1$, C(O)N(R$^1$)$_2$, NHC(O)R$^1$, NR$^1$C(O)R$^1$, NHSO$_2$R$^1$, NR$^1$SO$_2$R$^1$, NHC(O)OR$^1$, NR$^1$C(O)R$^1$, SO$_2$NH$_2$, SO$_2$NHR$^1$, SO$_2$N(R$^1$)$_2$, NHC(O)NH$_2$, NHC(O)NHR$^1$, NHC(O)N(R$^1$)$_2$, OH, C(O)OH, CN, CF$_3$, OCF$_3$, CF$_2$CF$_3$, F, Cl, Br or I as in Formula (IX); wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

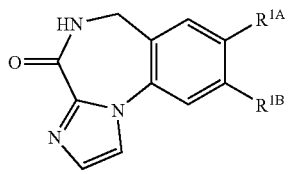

62. In another embodiment of Formula (I), X is a CH$_2$, and A$^1$ and A$^2$, together with the atoms to which they are attached are imidazole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, OR$^1$, SR$^1$, C(O)R$^1$, C(O)NH$_2$, C(O)NHR$^1$, C(O)N(R$^1$)$_2$, NHC(O)R$^1$, or NR$^1$C(O)R$^1$ as in Formula (IX); and wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

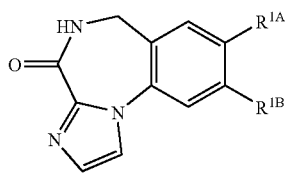

63. In another embodiment of Formula (I), X is a CH$_2$, and A$^1$ and A$^2$, together with the atoms to which they are attached are imidazole; and one of R$^{1A}$ and R$^{1B}$ is H, and the other is R$^1$, C(O)R$^1$, C(O)NHR$^1$, or C(O)N(R$^1$)$_2$ as in Formula (IX); and wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

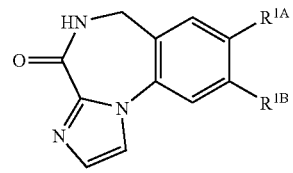

64. In another embodiment of Formula (I), X is a CH$_2$, and A$^1$ and A$^2$, together with the atoms to which they are attached are imidazole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (IX); and R$^1$ is R$^2$, R$^3$, R$^4$ or R$^5$; R$^2$ is phenyl; R$^3$ is heteroarene; R$^4$ is cycloalkyl, cycloalkenyl, heterocycloalkyl or heterocycloalkenyl; R$^7$ is phenyl; R$^8$ is heteroarene; R$^9$ is cycloalkyl, cycloalkenyl, heterocycloalkyl or heterocycloalkenyl; R$^{12}$ is phenyl; R$^{13}$ is heteroarene; R$^{14}$ is cycloalkyl, cycloalkenyl, heterocycloalkyl or heterocycloalkenyl; R$^{16}$ is phenyl; R$^{17}$ is heteroaryl; R$^{18}$ is cycloalkyl, cycloalkenyl, heterocycloalkyl or heterocycloalkenyl; R$^{21}$ is phenyl, heteroaryl, cycloalkyl, cycloalkenyl, heterocycloalkyl, or heterocycloalkenyl; R$^{22}$ is phenyl, heteroaryl, cycloalkyl, cycloalkenyl, heterocycloalkyl or heterocycloalkenyl; R$^{24}$ is phenyl; R$^{25}$ is heteroaryl; and R$^{26}$ is cycloalkyl, cycloalkenyl, heterocycloalkyl or heterocycloalkenyl, and wherein R$^5$, R$^6$, R$^{10}$, R$^{11}$, R$^{15}$, R$^{19}$, R$^{20}$, R$^{23}$, R$^{27}$, R$^{28}$, R$^{29}$, and R$^{30}$ are as described in Formula (I).

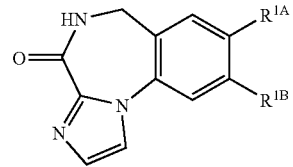

65. In another embodiment of Formula (I), X is a CH$_2$, and A$^1$ and A$^2$, together with the atoms to which they are attached are imidazole; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (IX); and R$^1$ is R$^2$, R$^3$, R$^4$ or R$^5$; R$^2$ is phenyl; R$^3$ is heteroarene; R$^4$ is cycloalkyl or heterocycloalkyl; R$^7$ is phenyl; R$^8$ is heteroarene; R$^9$ is cycloalkyl, or heterocycloalkyl; R$^{12}$ is phenyl; R$^{14}$ is cycloalkyl, or heterocycloalkyl; R$^{18}$ is heterocycloalkyl; R$^{28}$ is phenyl; and wherein R$^5$, R$^6$, R$^{10}$, R$^{11}$, R$^{15}$, R$^{19}$, R$^{20}$, R$^{23}$, R$^{27}$, R$^{28}$, R$^{29}$, and R$^{30}$ are as described in Formula (I).

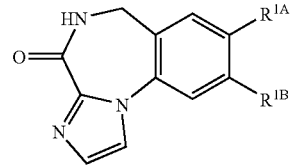

66. In another embodiment of Formula (I), X is a $CH_2$, and $A^1$ and $A^2$, together with the atoms to which they are attached are imidazole; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (IX); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or two of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

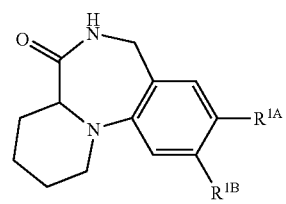

67. In another embodiment of Formula (I), X is a $CH_2$, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $S(O)R^1$, $SO_2R^1$, $NH_2$, $NHR^1$, $N(R^1)_2$, $C(O)R^1$, $C(O)NH_2$, $C(O)NHR^1$, $C(O)N(R^1)_2$, $NHC(O)R^1$, $NR^1C(O)R^1$, $NHSO_2R^1$, $NR^1SO_2R^1$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, OH, $C(O)OH$, CN, $CF_3$, $OCF_3$, $CF_2CF_3$, F, Cl, Br or I as in Formula (X); wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

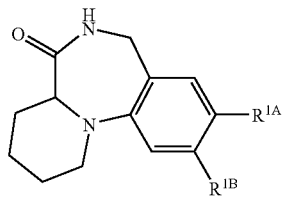

68. In another embodiment of Formula (I), X is a $CH_2$, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $OR^1$, $SR^1$, $C(O)R^1$, $C(O)NH_2$, $C(O)NHR^1$, $C(O)N(R^1)_2$, $NHC(O)R^1$, or $NR^1C(O)R^1$ as in Formula (X); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{21}$, $R^{23}$, $R^{24}$, $R^{25}$, $R^{26}$, $R^{27}$, $R^{28}$, $R^{29}$, and $R^{30}$ are as described in Formula (I).

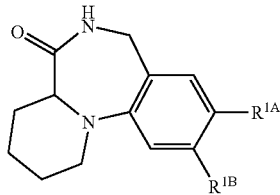

69. In another embodiment of Formula (I), X is a $CH_2$, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (X); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

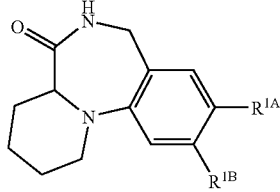

70. In another embodiment of Formula (I), X is a $CH_2$, and $A^1$ and $A^2$, together with the atoms to which they are attached are piperidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (X); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

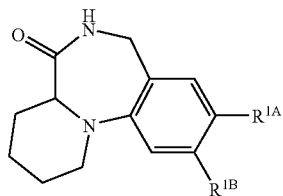

X

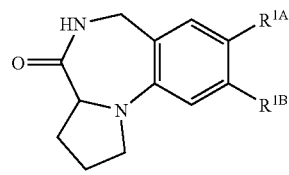

XI

71. In another embodiment of Formula (I), X is a CH$_2$, and A$^1$ and A$^2$, together with the atoms to which they are attached are piperidine; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (X); and R$^1$ is R$^2$, R$^3$, R$^4$ or R$^5$; R$^2$ is phenyl; R$^3$ is heteroarene; R$^4$ is cycloalkyl or heterocycloalkyl; R$^7$ is phenyl; R$^8$ is heteroarene; R$^9$ is cycloalkyl, or heterocycloalkyl; R$^{12}$ is phenyl; R$^{14}$ is cycloalkyl, or heterocycloalkyl; R$^{18}$ is heterocycloalkyl; R$^{28}$ is phenyl; and wherein R$^5$, R$^6$, R$^{10}$, R$^{11}$, R$^{15}$, R$^{19}$, R$^{20}$, R$^{23}$, R$^{27}$, R$^{28}$, R$^{29}$, and R$^{30}$ are as described in Formula (I).

73. In another embodiment of Formula (I), X is a CH$_2$, and A$^1$ and A$^2$, together with the atoms to which they are attached are pyrrolidine; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, OR$^1$, SR$^1$, S(O)R$^1$, SO$_2$R$^1$, NH$_2$, NHR$^1$, N(R$^1$)$_2$, C(O)R$^1$, C(O)NH$_2$, C(O)NHR$^1$, C(O)N(R$^1$)$_2$, NHC(O)R$^1$, NR$^1$C(O)R$^1$, NHSO$_2$R$^1$, NR$^1$SO$_2$R$^1$, NHC(O)OR$^1$, NR$^1$C(O)OR$^1$, SO$_2$NH$_2$, SO$_2$NHR$^1$, SO$_2$N(R$^1$)$_2$, NHC(O)NH$_2$, NHC(O)NHR$^1$, NHC(O)N(R$^1$)$_2$, OH, C(O)OH, CN, CF$_3$, OCF$_3$, CF$_2$CF$_3$, F, Cl, Br or I as in Formula (XI); wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formnula (I).

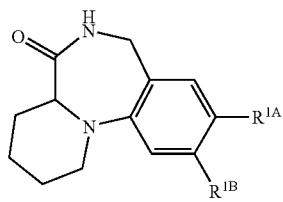

X

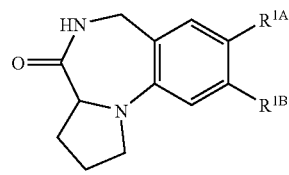

XI

72. In another embodiment of Formula (I), X is a CH$_2$, and A$^1$ and A$^2$, together with the atoms to which they are attached are piperidine; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, C(O)R$^1$, C(O)NHR$^1$, or C(O)N(R$^1$)$_2$ as in Formula (X); and R$^1$ is R$^2$, R$^3$, R$^4$ or R$^5$; R$^2$ is phenyl; R$^3$ is heteroarene; R$^4$ is cycloalkyl or heterocycloalkyl; R$^5$ is alkyl which is unsubstituted or substituted with one or two of independently selected R$^6$, NHR$^6$, N(R$^6$)$_2$, C(O)R$^6$, NR$^6$C(O)R$^6$, or NR$^6$S(O)$_2$R$^6$; R$^6$ is R$^7$, R$^8$, R$^9$ or R$^{10}$; R$^7$ is phenyl; R$^8$ is heteroarene; R$^9$ is cycloalkyl or heterocycloalkyl; R$^{10}$ is alkyl which is unsubstituted or substituted with one or two of independently selected R$^{11}$, C(O)OH, N(R$^{11}$)$_2$, C(O)R$^{11}$, or C(O)OR$^{11}$; R$^{11}$ is R$^{12}$, R$^{14}$ or R$^{14A}$; R$^{12}$ is phenyl; R$^{14}$ is cycloalkyl or heterocycloalkyl; R$^{14A}$ is alkyl; wherein the moieties represented by R$^2$, R$^4$, and R$^9$ are independently unsubstituted independently substituted with R$^{15}$, SO$_2$R$^{15}$, NH$_2$, N(R$^{15}$)$_2$, or (O); wherein R$^{15}$ is R$^{18}$ or R$^{19}$; R$^{18}$ is heterocycloalkyl; R$^{19}$ is alkyl; wherein the moieties represented by R$^{18}$ are independently unsubstituted or independently substituted with R$^{23}$; wherein R$^{23}$ is R$^{27}$; R$^{27}$ is alkyl each of which is substituted with R$^{28}$; and R$^{28}$ is phenyl.

74. In another embodiment of Formula (I), X is a CH$_2$, and A$^1$ and A$^2$, together with the atoms to which they are attached are pyrrolidine; A$^3$ and A$^4$, together with the atoms to which they are attached, are benzene which is substituted with R$^{1A}$ and R$^{1B}$; and one of R$^{1A}$ and R$^{1B}$ is H, and the other is R$^1$, OR$^1$, SR$^1$, C(O)R$^1$, C(O)NH$_2$, C(O)NHR$^1$, C(O)N(R$^1$)$_2$, NHC(O)R$^1$, or NR$^1$C(O)R$^1$ as in Formula (XI); and where in R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, and R$^{30}$ are as described in Formula (I).

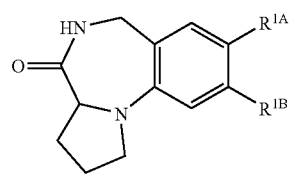

XI

75. In another embodiment of Formula (I), X is a $CH_2$, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (XI); and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are as described in Formula (I).

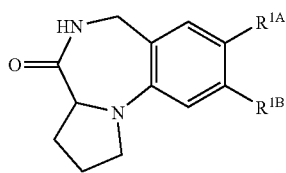

XI

76. In another embodiment of Formula (I), X is a $CH_2$, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (XI); and $R^1$ is $R^2$, $R^3$, $R^4$ or $R^5$; $R^2$ is phenyl; $R^3$ is heteroarene; $R^4$ is cycloalkyl, cycloalkenyl, heterocycloalkyl or heterocycloalkenyl; $R^7$ is phenyl; $R^8$ is heteroarene; $R^9$ is cycloalkyl, cycloalkenyl, heterocycloalkyl or heterocycloalkenyl; $R^{12}$ is phenyl; $R^{13}$ is heteroarene; $R^{14}$ is cycloalkyl, cycloalkenyl, heterocycloalkyl or heterocycloalkenyl; $R^{16}$ is phenyl; $R^{17}$ is heteroaryl; $R^{18}$ is cycloalkyl, cycloalkenyl, heterocycloalkyl or heterocycloalkenyl; $R^{21}$ is phenyl, heteroaryl, cycloalkyl, cycloalkenyl, heterocycloalkyl, or heterocycloalkenyl; $R^{22}$ is phenyl, heteroaryl, cycloalkyl, cycloalkenyl, heterocycloalkyl or heterocycloalkenyl; $R^{24}$ is phenyl; $R^{25}$ is heteroaryl; and $R^{26}$ is cycloalkyl, cycloalkenyl, heterocycloalkyl or heterocycloalkenyl, and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

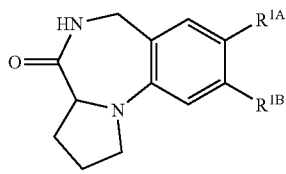

XI

77. In another embodiment of Formula (I), X is a $CH_2$, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (XI); and $R^1$ is $R^2$, $R^3$, $R^4$ or $R^5$; $R^2$ is phenyl; $R^3$ is heteroarene; $R^4$ is cycloalkyl or heterocycloalkyl; $R^7$ is phenyl; $R^8$ is heteroarene; $R^9$ is cycloalkyl, or heterocycloalkyl; $R^{12}$ is phenyl; $R^{14}$ is cycloalkyl, or heterocycloalkyl; $R^{18}$ is heterocycloalkyl; $R^{28}$ is phenyl; and wherein $R^5$, $R^6$, $R^{10}$, $R^{11}$, $R^{15}$, $R^{19}$, $R^{20}$, $R^{23}$, $R^{27}$, $R^{28}$, $R^{29}$, and $R^{30}$ are as described in Formula (I).

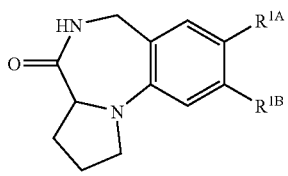

XI

78. In another embodiment of Formula (I), X is a $CH_2$, and $A^1$ and $A^2$, together with the atoms to which they are attached are pyrrolidine; $A^3$ and $A^4$, together with the atoms to which they are attached, are benzene which is substituted with $R^{1A}$ and $R^{1B}$; and one of $R^{1A}$ and $R^{1B}$ is H, and the other is $R^1$, $C(O)R^1$, $C(O)NHR^1$, or $C(O)N(R^1)_2$ as in Formula (XI); and $R^1$ is $R^2$, $R^3$, $R^4$ or $R^5$; $R^2$ is phenyl; $R^3$ is heteroarene; $R^4$ is cycloalkyl or heterocycloalkyl; $R^5$ is alkyl which is unsubstituted or substituted with one or two of independently selected $R^6$, $NHR^6$, $N(R^6)_2$, $C(O)R^6$, $NR^6C(O)R^6$, or $NR^6S(O)_2R^6$; $R^6$ is $R^7$, $R^8$, $R^9$ or $R^{10}$; $R^7$ is phenyl; $R^8$ is heteroarene; $R^9$ is cycloalkyl or heterocycloalkyl; $R^{10}$ is alkyl which is unsubstituted or substituted with one or twvo of independently selected $R^{11}$, $C(O)OH$, $N(R^{11})_2$, $C(O)R^{11}$, or $C(O)OR^{11}$; $R^{11}$ is $R^{12}$, $R^{14}$ or $R^{14A}$; $R^{12}$ is phenyl; $R^{14}$ is cycloalkyl or heterocycloalkyl; $R^{14A}$ is alkyl; wherein the moieties represented by $R^2$, $R^4$, and $R^9$ are independently unsubstituted independently substituted with $R^{15}$, $SO_2R^{15}$, $NH_2$, $N(R^{15})_2$, or (O); wherein $R^{15}$ is $R^{18}$ or $R^{19}$; $R^{18}$ is heterocycloalkyl; $R^{19}$ is alkyl; wherein the moieties represented by $R^{18}$ are independently unsubstituted or independently substituted with $R^{23}$; wherein $R^{23}$ is $R^{27}$; $R^{27}$ is alkyl each of which is substituted with $R^{28}$; and $R^{28}$ is phenyl.

Schemes

The starting materials used herein are commercially available or may be prepared by routine methods well known to those of ordinary skill in the art. The compounds of the present invention may be prepared using the methods illustrated in the general synthetic schemes and experimental procedures detailed below. The general synthetic schemes are presented for purposes of illustration and are not intended to be limiting.

Scheme 1

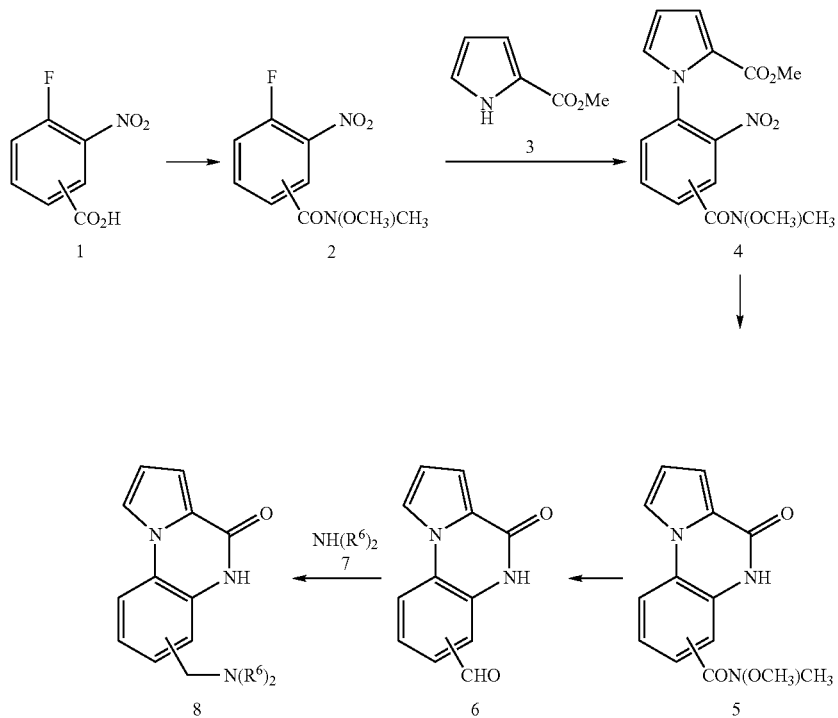

As shown in Scheme 1, a fluoro-nitrobenzoic acid of Formula (1) can be converted to a Weinreb amide of Formula (2) using amide bond formation conditions known to those skilled in the art and widely available in the literature. Reaction of a compound of Formula (2) with methyl 1H-pyrrole-2-carboxylate (3) using a base such as but not limited to cesium carbonate will provide a compound of Formula (4). The reaction is typically performed at room temperature or elevated temperatures in a solvent such as but not limited to DMF, THF, and the like. Compounds of Formula (4) can be converted to compounds of Formula (5) by reducing the nitro group of (4) to the amine under palladium catalyzed hydrogenation conditions, followed by heating. Typical hydrogenation conditions include the use of a catalyst such as but not limited to palladium on carbon, along with hydrogen gas in a solvent such as but not limited to methanol. Reduction of the Weinreb amide of Formula (5) will provide the corresponding aldehyde of Formula (6). The reaction is typically performed below room temperature using a reducing agent such as but not limited to lithium aluminum hydride in a solvent such as but not limited to DMF, THF, and the like. Compounds of Formula (8) can be prepared by reacting compounds of Formula (6) with amines of Formula (7) wherein each $R_6$ is H or is as described in Formnula (1) or wherein $NH(R_6)_2$ is a heterocyclic amine of Formula $R^9$. Typical reaction conditions include the addition of a reducing agent such as but not limited to sodium traicetoxyborohydride, and acetic acid. The reaction can be performed at or above room temperature in a solvent such as dichloromethane, dichloroethane and the like.

Scheme 2

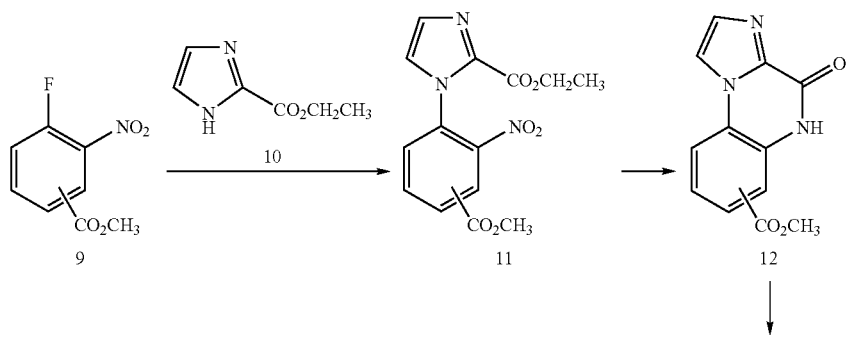

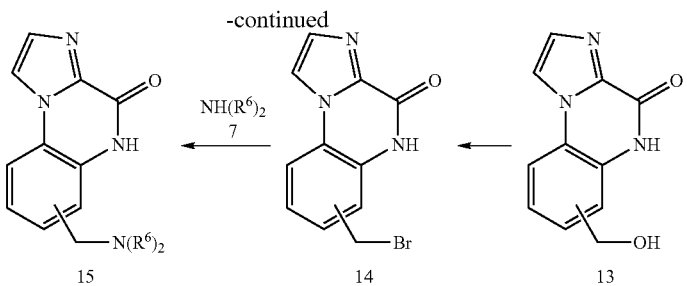

Reaction of a fluoro-nitrobenzoate of Formula (9), which can be prepared as described in Example 21A, with ethyl imidazole-2-carboxylate (10) and a base such as but not limited to cesium carbonate, will provide compounds of Formula (11). The reaction is typically performed at room temperature or elevated temperatures in a solvent such as but not limited to DMF, THF, and the like. Compounds of Formula (11) can be converted to compounds of Formula (12) by reducing the nitro group of (11) to the corresponding amine under palladium catalyzed hydrogenation conditions, followed by heating. Typical hydrogenation conditions include the use of a catalyst such as but not limited to palladium on carbon, along with hydrogen gas in a solvent such as but not limited to methanol. Reduction of the ester of Formula (12) to the corresponding alcohol of Formula (13) can be accomplished using a reducing agent such as but limited to lithium aluminum hydride. The reaction is typically performed below room temperature in a solvent such as but not limited to DMF, THF, and the like. Alcohols of Formula (13) can be converted to bromides of Formula (14) by treatment with phosphorus tribromide at room temperature in a solvent such as but not limited to dioxane. Reaction of (14) with a primary or secondary amine of Formula (7) (wherein each $R_6$ is H or is as described in Formula (I)) at room temperature will provide the benzylic amine of Formula (15). Additionally, a heterocyclic amine ($R_9$) may be used in place of $N(R_6)_2$. The reaction is typically performed in a solvent such as but not limited to acetonitrile.

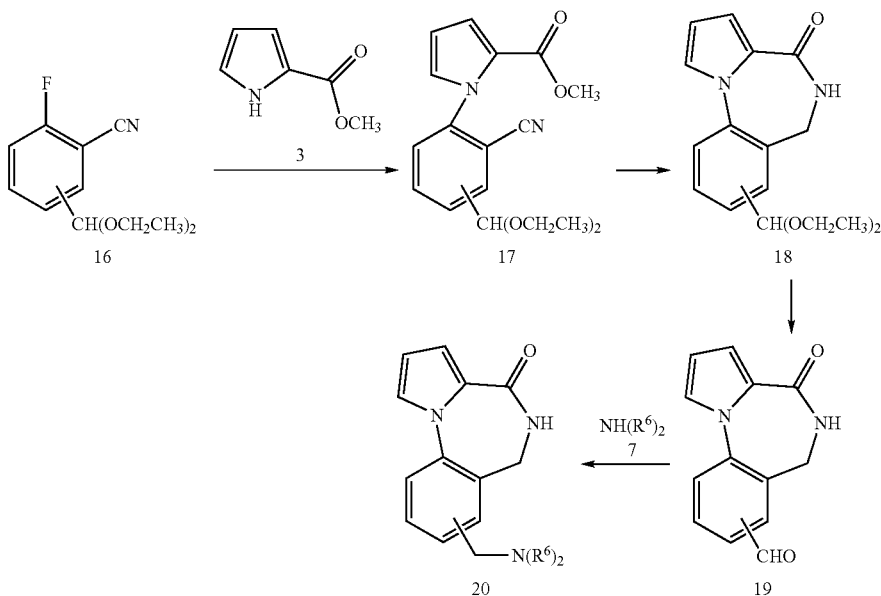

Scheme 3

As shown in Scheme 3, a fluoro-cyanobenzaldehyde acetal of Formula (16), which can be prepared as described in Example 26A, can be reacted with methyl-1H-pyrrole-2-carboxylate (3) to provide the coupled compound of Formula (17). The reaction typically requires a base such as but not limited to cesium carbonate, and is performed at room temperature or elevated temperatures in a solvent such as but not limited to DMF, THF, and the like. Reduction of the cyano group on the compound of Formula (17) to the benzylic amine under standard Raney nickel reduction conditions, will also result in ring closure and provide the lactam of Formula (18). Treatment of a compound of Formula (18) with an acid such as but not limited to hydrochloric acid, will provide an aldehyde of Formula (19). The reaction is typically performed at room temperature in an aqueous solvent such as but not limited to THF, dioxane, and the like. Compounds of Formula (20) can be prepared by reacting compounds of Formula (19) with amines of Formula (7) wherein each $R_6$ is H or is as described in Formula (I) or wherein $N(R_6)_2$ is a heterocyclic amine of Formula $R^9$. Typical reaction condi-

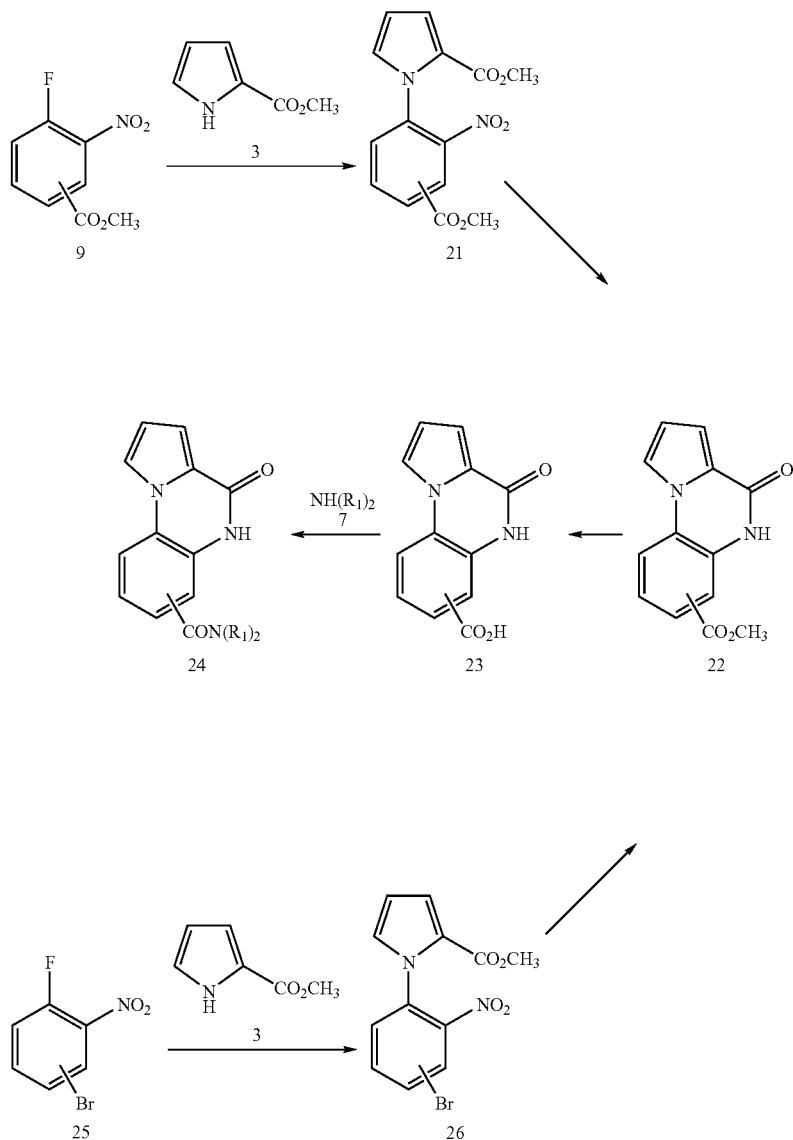

Scheme 4

A fluoro-nitrobenzoate of Formula (9) can be reacted with methyl 1H-pyrrole-2-carboxylate (3) and a base such as but not limited to cesium carbonate to provide the coupled compound of Formula (21). The reaction is typically performed at elevated temperatures in a solvent such as but not limited to THF, DMF and the like. Reduction of the nitro group on the compound of Formula (21) to the benzylic amine under standard Raney nickel reduction conditions, will also result in ring closure and provide the lactam of Formula (22). Saponification of the ester of Formula (22) with aqueous lithium hydroxide will provide the acid of Formula (23). The reaction may be performed in a solvent such as THF, methanol, or combinations thereof. Coupling an acid of Formula (23) with a primary or secondary amine of Formula (7) (wherein $R_1$ is H or is as described in Formula (I) or wherein $N(R_1)_2$ is a heterocyclic amine of Formula $R^4$), under standard peptide bond forming conditions known to those skilled in the art and widely available in the literature, will provide an amide of Formula (24). Alternatively, a fluoro-nitro-bromobenzene of Formula (25) can be reacted with methyl 1H-pyrrole-2-carboxylate (3) and a base such as but not limited to cesium carbonate to provide the coupled compound of Formula (26). Compounds of Formula (26) can be converted to compounds of Formula (22) using palladium-atalyzed carbonylation conditions in the presence of methanol, which will result in both reduction of the nitro group and ring closure to give the lactam of Formula (22). The reaction is typically performed at elevated temperatures. In addition to methanol and carbon monoxide, a base such as but not limited to triethylamine and a catalyst such as but not limited to dichloro[1,1'-ferrocenyl-bis(diphenyl-phosphine)]palladium(II) dichloromethane are typically employed.

Scheme 5

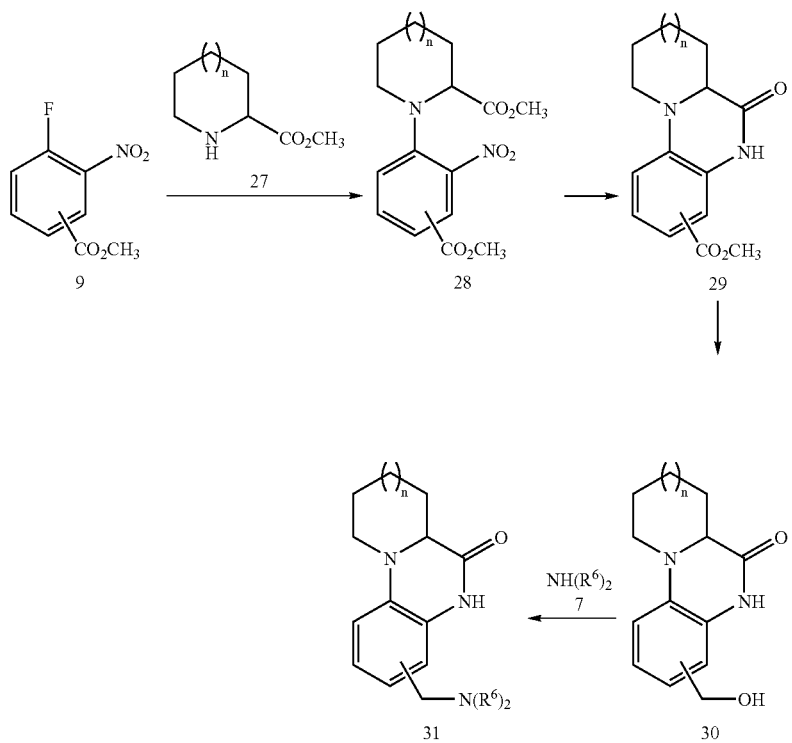

A fluoro-nitrobenzoate of Formula (9) can be reacted with a cyclic amine of Formula (27), wherein n is 0 or 1, and a base such as but not limited to cesium carbonate to provide a coupled compound of Formula (28). The reaction is typically performed at elevated temperatures in a solvent such as but not limited to DMF. Compounds of Formula (28) can be converted to compounds of Formula (29) by reducing the nitro group of (28) to the amine under palladium catalyzed hydrogenation conditions, followed by heating. Typical hydrogenation conditions include the use of a catalyst such as but not limited to palladium on carbon, along with hydrogen gas in a solvent such as but not limited to methanol. Reduction of the ester of Formula (29) to the corresponding alcohol of Formula (30) can be accomplished using a reducing agent such as but not limited to lithium aluminum hydride in a solvent such as but not limited to THF. The reaction is typically conducted below room temperature before quenching with hydrochloric acid. Compounds of Formula (30) can be converted to compounds of Formula (31) using standard Mitsunobu reaction conditions known to those skilled in the art and widely available in the literature, wherein $R_6$ is H or is as described in Formula (I) or wherein $N(R_6)_2$ is a heterocyclic amine of Formula $R^9$.

The following examples are presented to provide what is believed to be the most useful and readily understood description of procedures and conceptual aspects of this invention. These compounds were named using ACD/ChemSketch Version 5.06 (5 Jun. 2001, Advanced Chemistry Development Inc. Toronto, Ontario).

EXAMPLE 1

7-((cyclohexylamino)methyl)pyrrolo[1,2-a]quinoxalin-4(5H)-one

EXAMPLE 1A

To a solution of 4-fluoro-3-nitrobenzoic acid (1.54 g) in 30 mL methylene chloride was added 3 mL oxalyl chloride (34.4 mmol) followed by 0.1 mL DMF. The reaction was stirred overnight at room temperature. After concentrating, the concentrate was dissolved in 50 mL methylene chloride and 5 mL N,N'-diisopropylethylamine was added slowly followed by N,O-dimethylhydroxylamine hydrochloride (1.08 g). After 8 hours at room temperature, the crude reaction was filtered through silica gel (10 g) eluting with 1:1 ethyl acetate:hexane. This example was used in the next step without any further purification. $^1$H NMR (300 MHz, DMSO-$d_6$) δ8.36 (dd, 1H), 8.06 (m, 1H), 7.69 (m, 1H), 3.58 (s, 3H), 3.31 (s, 3H).

EXAMPLE 1B

Methyl 1H-pyrrole-2-carboxylate (3.2 g), EXAMPLE 1A (5.38 g) and cesium carbonate (11.73 g) were stirred in 20 mL DMF at room temperature for 48 hours. The reaction mixture was partitioned between ethyl acetate and $H_2O$. The aqueous phase was extracted with 6×40 mL ethyl acetate. The extract were dried over $MgSO_4$, filtered and concentrated. The crude product was purified on silica gel (120 g) eluting with 1:1 ethyl acetate:hexane. $^1$H NMR (300 MHz, DMSO-$d_6$) δ 8.35 (δ, 1H), 8.03 (δδ, 1H), 7.67 (δ, 1H), 7.35(t, 1H), 7.08 (m, 1H), 6.42 (m, 1H), 3.63 (s, 3H), 3.60 (s, 3H), 3.34 (s, 3H).

EXAMPLE 1C

The product from EXAMPLE 1B (2.81 g) was dissolved in 30 mL methanol. While stirring vigorously, 10% Pd/C (286 mg) was added and the reaction was stirred under a $H_2$ balloon for 24 hours. The catalyst was removed by filtering through Celite. After concentrating the filtrate, the oil was dissolved in 40 mL dioxane and refluxed for 3 hours. The crude product was purified on silica gel (90 g) eluting with 5/95 2M ammonia in methanol/methylene chloride to provide This example. $^1$H NMR (300 MHz, DMSO-$d_6$) δ 11.38 (βρ σ, 1H), 8.23 (μ, 1H), 8.10 (d, 1H), 7.60 (s, 1H), 7.48 (d, 1H), 7.07 (m, 1H), 6.73 (m, 1H), 3.59 (s, 3H), 3.29 (s, 3H).

EXAMPLE 1D

The product from EXAMPLE 1C (1.4 g) was dissolved in 40 mL THF and cooled to 0° under $N_2$. To the cooled solution was added 1M lithium aluminum in THF (10 mL) over 5 minutes. After 0.5 hours, the reaction was quenched 1M HCl. The solid was filtered and purified on silica gel (40 g) eluting with 1:1 ethyl acetate:hexane to provide This example. $^1$H NMR (300 MHz, DMSO-$d_6$) δ11.52(s, 1H), 9.99 (s, 1H), 8.27 (m, 2H), 7.78 (m, 2H), 7.11 (m, 1H) 6.77 (m, 2H),

EXAMPLE 1E 7-((cyclohexylamino)methyl)pyrrolo[1,2-a]quinoxalin-4(5H)-one

EXAMPLE 1D (63 mg), cyclohexylamine (157 mg), sodium triacetoxyborohydride (83 mg) and 6 drops acetic acid were combined in 5 mL dichloroethane. After stirring at room temperature overnight, the mixture was concentrated and the concentrate was purified on silica gel (12 g ) eluting with 1:1 ethyl acetate to provide This example. $^1$H NMR (300 MHz, DMSO-$d_6$) δ 11.26 (br s, 1H), 8.16 (s, 1H), 8.00 (d, 1H), 7.32 (s, 1H), 7.23 (d, 1H), 7.02 (m, 1H), 6.88 (t, 1H), 3.87 (brs, 2H), 1.91 (m, 2H), 1.69 (m, 2H), 1.55 (m, 1H), 1.19 (m, 6H).

EXAMPLE 2

7-(((cyclohexylmethyl)amino)methyl)pyrrolo[1,2-a]quinoxalin-4(5H)-one

This example was prepared as described in EXAMPLE 1E, substituting aminomethylcyclohexane (76 mg) for cyclohexylamine. This example was isolated after purification by RP-HPLC using a gradient elution of 10/90 acetonitrile/0.1% TFA in water to 50/50 at 254 nm over 30 minutes. $^1$H NMR (300 MHz, DMSO-$d_6$) δ 11.49 (s, 1H), 8.21 (m, 1H), 8.12 (d, 1H), 7.38 (m, 2H), 7.05 (m, 1H), 6.72 (m, 1H), 4.17 (br t, 2H), 2.80 (m, 2H), 1.69 (m, 6H), 1.19 (m, 3H), 0.95 (m, 2H).

EXAMPLE 3

7-((cyclobutylamino)methyl)pyrrolo[1,2-a]quinoxalin-4(5H)-one

This example was prepared as described in EXAMPLE 2, substituting cyclobutylamine for aminomethylcyclohexane. $^1$H NMR (300 MHz, DMSO-$d_6$) δ 11.49 (s, 1H), 8.21 (m, 1H), 8.12 (d, 1H), 7.30 (m, 2H), 7.06 (m, 1H), 6.72 (m, 1H), 4.07 (br s, 2H), 3.75 (m, 1H), 2.18 (m, 4H), 1.79 (m, 2H).

EXAMPLE 4

7-((cyclopentylamino)methyl)pyrrolo[1,2-a]quinoxalin-4(5H)-one

This example was prepared as described in EXAMPLE 2, substituting cyclopentylamine for aminomethylcyclohexane. $^1$H NMR (300 MHz, DMSO-$d_6$) δ 11.49 (s, 1H), 8.21 (s, 1H), 8.13 (d, 1H), 7.34 (m, 2H), 7.06 (d, 1H), 6.72 (m, 1H), 4.18 (br s, 2H), 3.52 (br t, 1H), 2.00 (m, 2H), 1.63 (m, 6H).

EXAMPLE 5

7-((cyclopropylamino)methyl)pyrrolo[1,2-a]quinoxalin-4(5H)-one

This example was prepared as described in EXAMPLE 2, substituting cyclopropylamine for aminomethylcyclohexane. $^1$H NMR (300 MHz, DMSO-$d_6$) δ 11.49 (s, 1H), 8.21 (s, 1H), 8.13 (d, 1H), 7.35 (m, 2H), 7.05 (m, 1H), 6.72 (t, 1H), 2.72 (m, 1H), 0.81 (m, 4H).

EXAMPLE 6

7-(piperidin-1-ylmethyl)pyrrolo[1,2-a]quinoxalin-4(5H)-one

This example was prepared as described in EXAMPLE 1E, substituting piperidine for cyclohexylamine. $^1$H NMR (300 MHz, DMSO-$d_6$) δ 11.17 (s, 1H), 8.14 (m, 1H), 7.95 (d, 1H), 7.25 (s, 1H), 7.10 (br d, 1H), 7.00 (dd, 1H), 6.79 (m, 1H), 3.44 (s, 2H), 2.33 (m, 4H), 1.49 (m, 6H).

EXAMPLE 7

7-(pyrrolidin-1-ylmethyl)pyrrolo[1,2-a]quinoxalin-4(5H)-one

This example was prepared as described in EXAMPLE 1E, substituting pyrrolidine for cyclohexylamine. $^1$H NMR (300 MHz, DMSO-$d_6$) δ 11.17 (br s, 1H), 8.14 (m, 1H), 7.95 (d, 1H), 7.26 (br s, 1H), 7.11 (dd, 1H), 7.00 (m, 1H), 6.66 (m, 1H), 3.59 (s, 2H), 2.44 (m, 4H), 1.70 (4H).

EXAMPLE 8

8-((cyclohexylamino)methyl)pyrrolo[1,2-a]quinoxalin-4(5H)-one

EXAMPLE 8A

To a solution of 3-fluoro4-nitrobenzoic acid (1.09 g) in 30 mL methylene chloride was added 2 mL oxalyl chloride (23 mmol) followed by 0.1 mL DMF. The reaction was stirred overnight at room temperature. After concentrating, the concentrate was dissolved in 50 mL methylene chloride and 5 mL N,N'-diisopropylethylamine was added slowly followed by N,O-dimethylhydroxylamine hydrochloride (0.75 g). After 8 hours at room temperature, the crude reaction was filtered through silica gel (10 g) eluting with 1:1 ethyl acetate:hexane. The filtrate was concentrated to provide This example, $^1$H NMR (300 MHz, DMSO-$d_6$) δ8.22 (t, 1H), 7.77 (dd, 1H), 7.62 (dt, 1H), 3.56 (s, 3H), 3.29 (s, 3H).

EXAMPLE 8B

Methyl 1H-pyrrole-2-carboxylate (0.716 g), EXAMPLE 8A (1.18 g) and cesium carbonate (3.28 g) were stirred in 20 mL DMF at room temperature for 48 hours. The reaction mixture was partitioned between ethyl acetate and $H_2O$. The aqueous phase was extracted with ethyl acetate. The extract were dried over $MgSO_4$, filtered and concentrated. The crude product was purified on silica gel (40 g) eluting with 1:1 ethyl acetate:hexane to provide This example. $^1H$ NMR (300 MHz, DMSO-$d_6$) δ 8.21 (d, 1H), 7.90 (dd, 1H), 7.73 (d, 1H), 7.33 (d, 1H), 7.07 (m, 1H), 6.40 (m, 1H), 3.59 (s, 3H), 3.50 (s, 3H), 3.29 (s3H).

EXAMPLE 8C

EXAMPLE 8B (0.434 g) was dissolved in 30 mL methanol. While the mixture stirred vigorously, 10% Pd/C (40 mg) was added and the reaction was stirred under a $H_2$ balloon for 24 hours. The catalyst was removed by filtering through Celite. After concentrating, the resultant oil was dissolved in 40 mL dioxane and refluxed for 3 hours. The crude product was purified on silica gel (40 g) eluting with 5/95 2M ammonia in methanol/methylene chloride to provide This example. $^1H$ NMR (300 MHz, DMSO-$d_6$) δ 11.43 (br s, 1H). 8.27 (m, 2H), 7.51 (dd, 1H), 7.31 (d, 1H), 7.05 (dd, 1H), 6.70 (q, 1H), 3.50 (s, 3H), 3.29 (s, 3H).

EXAMPLE 8D

EXAMPLE 8C (0.348 g) was dissolved in 20 mL THF and cooled to 0° under $N_2$. To the cooled solution was added 1M lithium aluminum in THF (2.5 mL) over 5 minutes. After 0.5 hours, the reaction was quenched 1M HCl. The solid was filtered and purified on silica gel (40 g) eluting with 1:1 ethyl acetate:hexane to provide This example. $^1H$ NMR (300 MHz, DMSO-$d_6$) δ 11.68 (s, 1H), 9.98 (s, 1H), 8.60 (s, 1H), 8.34 (s, 1H), 7.83 (d, 1H), 7.44 (d, 1H), 7.09 (m, 1H), 6.74 (m, 1H),

EXAMPLE 8E 8-((cyclohexylamino)methyl)pyrrolo[1,2-a]quinoxalin-4(5H)-one

EXAMPLE 8D (60 mg), cyclohexylamine (55 mg), sodium triacetoxyborohydride (71 mg) were combined with 6 drops acetic acid in 5 mL dichloroethane. After stirring at room temperature overnight, the reaction was concentrated and purified by RP-HPLC using a gradient elution of 10/90 acetonitrile/0.1% TFA in water to 50/50 at 254 nm over 30 minutes to provide This example. $^1H$ NMR (300 MHz, DMSO-$d_6$) δ 11.40 (s, 1H), 8.17 (s, 1H), 8.03 (s, 1H), 7.40 (d, 1H), 7.32 (s, 1H), 7.07 (d, 1H), 6.75 (m, 1H), 4.20 (s, 2H), 3.04 (m, 1H), 2.11 (br d, 2H), 1.78 (br d, 2H), 1.61 (br d, 1H), 1.30 (m, 4H), 1.11 (m, 1H).

EXAMPLE 9

8-(((cyclohexylmethyl)amino)methyl)pyrrolo[1,2-a]quinoxalin-4(5H)-one

This example was prepared as described in EXAMPLE 8E, substituting aminomethylcyclohexane for cyclohexylamine. $^1H$ NMR (300 MHz, DMSO-$d_6$) δ 11.40 (s, 1H), 8.15 (s, 1H), 8.02 (br s, 1H), 7.40 (d, 1H), 7.32 (d, 1H), 7.07 (m, 1H), 6.75 (t, 1H), 4.19 (s, 2H), 2.79 (br d, 2H), 1.70 (m, 6H), 1.19 (m, 3H), 0.93 (m, 2H).

EXAMPLE 10

7-((isopropylamino)methyl)pyrrolo[1,2-a]quinoxalin-4(5H)-one

This example was prepared as described in EXAMPLE 1E, substituting isopropylamine for cyclohexylamine. $^1H$ NMR (300 MHz, DMSO-$d_6$) δ 11.16 (br s, 1H), 8.14 (m, 1H), 7.94 (d, 1H), 7.29 (br s, 1H), 7.18 (dd, 1H), 7.00 (dd, 1H), 6.66 (d, 1H), 3.71 (s, 2H), 2.72 (m, 1H), 1.02 (d, 6H).

EXAMPLE 11

7-((benzylamino)methyl)pyrrolo[1,2-a]quinoxalin-4(5H)-one

This example was prepared as described in EXAMPLE 1E, substituting benzylamine for cyclohexylamine. $^1H$ NMR (300 MHz, DMSO-$d_6$) δ 11.24 (br s, 1H), 8.15 (m, 1H), 7.99 (d, 1H), 7.28 (m 7H0, 7.02 (m, 1H), 6.67 (m, 1H), 3.77 (br s, 4H).

EXAMPLE 12

8-((cyclopropylamino)methyl)pyrrolo[1,2-a]quinoxalin-4(5H)-one

This example was prepared as described in EXAMPLE 8E, substituting cyclopropylamine for cyclohexylamine. $^1H$ NMR (300 MHz, DMSO-$d_6$) δ 11.38 (s, 1H), 8.17 (s, 1H), 8.03 (m, 1H), 7.40 (dd, 1H), 7.32 (d, 1H), 7.07 (m, 1H), 6.75 (m, 1H), 4.29 (s, 2H), 2.73 (m, 1H), 0.81 (m, 4H).

EXAMPLE 13

8-((isopropylamino)methyl)pyrrolo[1,2-a]quinoxalin-4(5H)-one

This example was prepared as described in EXAMPLE 8E, substituting isopropylamine for cyclohexylamine. This example was isolated after purification on silica gel (12 g) eluting with 1:1 ethyl acetate:hexane. $^1H$ NMR (300 MHz, DMSO-$d_6$) δ 8.10 (m, 1H), 7.95 (s, 1H), 7.23 (m, 2H), 7.01 (m, 1H), 6.67 (t, 1H), 3.75 (s, 2H), 2.74 (m, 1H), 1.01 (d, 6).

EXAMPLE 14

This example was prepared as described in EXAMPLE 8E, substituting phenethylamine for cyclohexylamine. $^1H$ NMR (300 MHz, DMSO-$d_6$) δ 11.39 (s, 1H), 8.17 (s, 1H), 8.03 (m, 1H), 7.30 (m, 7H0, 7.08 (m, 1H), 6.75 (m, 1H), 4.26 (br s, 2H), 2.97 (t, 2H), 2.70 (t, 2H).

EXAMPLE 15

8-(pyrrolidin-1-ylmethyl)pyrrolo[1,2-a]quinoxalin-4(5H)-one

This example was prepared as described in EXAMPLE 8E, substituting pyrrolidine for cyclohexylamine. This example was isolated after purification on silica gel (12 g) eluting with 1:1 ethyl acetate:hexane. $^1H$ NMR (300 MHz, DMSO-$d_6$) δ

11.19 (s, 1H), 8.18 (m, 1H), 7.93 (s, 1H), 7.24 (s, 1H), 7.02 (m, 2H), 6.67 (m, 1H), 3.62 (s, 2H), 2.45 (m, 4H), 1.70 (m, 4H).

EXAMPLE 16

8-((cyclobutylamino)methyl)pyrrolo[1,2-a]quinoxalin-4(5H)-one

This example was prepared as described in EXAMPLE 8E, substituting cyclobutylamine for cyclohexylamine. This example was isolated after purification on silica gel (12 g) eluting with 1:1 ethyl acetate:hexane. $^1$H NMR (300 MHz, DMSO-$d_6$) δ 11.21 (br s, 1H), 8.14 (m, 1H), 7.97 (s, 1H), 7.25 (m, 2H), 7.02 (m, 1H), 6.69 (m, 1H), 3.60 (s, 2H), 3.20 (m, 1H), 2.08 (m, 2H), 1.73 (m, 2H), 1.59 (m, 2H).

EXAMPLE 17

8-(morpholin-4-ylmethyl)pyrrolo[1,2-a]quinoxalin-4(5H)-one

This example was prepared as described in EXAMPLE 8E, substituting morpholine for cyclohexylamine. $^1$H NMR (300 MHz, DMSO-$d_6$) δ 11.48 (s, 1H), 8.20 (s, 1H), 8.03 (m, 1H), 7.40 (q, 2H), 7.08 (m, 1H), 6.76 (m, 1H), 4.30 (s, 2H), 3.97 (m, 2H), 3.64 (m, 2H), 3.22 (m, 4H).

EXAMPLE 18

8-((cyclopentylamino)methyl)pyrrolo[1,2-a]quinoxalin-4(5H)-one

This example was prepared as described in EXAMPLE 8E, substituting cyclopentylamine for cyclohexylamine. This example was isolated after purification on silica gel (12 g) eluting with 1:1 ethyl acetate:hexane. $^1$H NMR (300 MHz, DMSO-$d_6$) δ 11.20 (br s, 1H), 8.14 (m, 1H), 7.98 (m, 1H), 7.25 (m, 2H), 7.02 (m, 1H), 6.68 (m, 1H), 3.72 (s, 2H), 2.99 (m, 1H), 1.66 (m, 4H), 1.39 (m, 4H).

EXAMPLE 19

8-(piperidin-1-ylmethyl)pyrrolo[1,2-a]quinoxalin-4(5H)-one

This example was prepared as described in EXAMPLE 8E, substituting piperidine for cyclohexylamine. This example was isolated after purification on silica gel (12 g) eluting with 1:1 ethyl acetate:hexane. $^1$H NMR (300 MHz, DMSO-$d_6$) δ 11.22 (s, 1H), 8.18 (m, 1H), 7.91 (s, 1H), 7.23 (q, 2H), 7.02 (m, 1H), 6.68 (m, 1H), 3.48 (s, 2H), 2.34 (m, 4H), 1.50 (m, 4H), 1.39 (m, 2H).

EXAMPLE 20

8-((benzylamino)methyl)pyrrolo[1,2-a]quinoxalin-4(5H)-one

This example was prepared as described in EXAMPLE 8E, substituting benzylamine for cyclohexylamine. This example was isolated after purification on silica gel (12 g) eluting with 1:1 ethyl acetate:hexane. $^1$H NMR (300 MHz, DMSO-$d_6$) δ 11.38 (s, 1H), 8.28 (s, 1H), 8.05 (s, 1H), 7.53 (d, 1H), 7.42 (m, 4H), 7.31 (d, 2H), 7.06 (d, 1H), 6.74 (m, 1H), 4.19 (s, 2H), 4.15 (s, 2H).

EXAMPLE 21

7-(pyrrolidin-1-ylmethyl)imidazo[1,2-a]quinoxalin-4(5H)-one

EXAMPLE 21A

To 4-fluoro-3-nitrobenzoic acid (2.02 g) in 50 mL anhydrous methanol was added thionyl chloride (1.6 mL) slowly over 15 minutes, and the mixture was refluxed for 4 hours. Concentration provided This example. $^1$H NMR (300 MHz, DMSO-$d_6$) δ 8.58 (dd, J=7.29, 2.20 Hz, 1H) 8.34 (ddd, J=8.73, 4.32, 2.20 Hz, 1H) 7.75 (dd, J=11.02, 8.65 Hz, 1H) 3.91 (s, 3H).

EXAMPLE 21B

Ethyl imidazole-2-carboxylate (0.58 g, 4.1 mmol), EXAMPLE 21A (0.822 g) and cesium carbonate (1.78 g) were combined in 20 mL of DMF. The mixture was stirred at 55° C. for 24 hours. The reaction was partitioned between ethyl acetate and water, and the aqueous phase was extracted with 4×40 mL of ethyl acetate. The extract were dried over MgSO$_4$, filtered and concentrated to provide This example which was used in the next step without any further purification. $^1$H NMR (300 MHz, DMSO-$d_6$) δ 8.65 (d, J=2.03 Hz, 1H) 8.39 (dd, J=8.31, 1.86 Hz, 1H) 7.86 (d, J=8.14 Hz, 1H) 7.75 (d, J=1.36 Hz, 1H) 7.36 (s, 1H) 4.11 (q, J=7.12 Hz, 2H) 3.96 (s, 3H) 1.10 (t, J=7.12 Hz, 3H).

EXAMPLE 21C

EXAMPLE 21B (1.8 g) was dissolved in 30 mL methanol. While stirring vigorously, 10% Pd/C (130 mg) was added and the reaction was stirred under a H$_2$ balloon for 24 hours. The catalyst was removed by filtering through Celite. After concentrating the filtrate, the resultant oil was dissolved in 40 mL dioxane and refluxed for 5 hours. The crude product was obtained after concentration and was used in the next step without any further purification. $^1$H NMR (300 MHz, DMSO-$d_6$) δ 12.00 (s, 1H) 8.60 (d, J=1.36 Hz, 1H) 8.24 (d, J=8.48 Hz, 1H) 8.01 (d, J=1.70 Hz, 1H) 7.84 (dd, J=8.65, 1.86 Hz, 1H) 7.64 (d, J=1.36 Hz, 1H) 3.90 (s, 3H).

EXAMPLE 21D

EXAMPLE 21C (0.60 g) was dissolved in 30 mL THF and cooled to 0° C. under N$_2$. To the cooled solution was added 1M lithium aluminum in THF (6 mL) over 5 minutes. After 0.5 hours at 0° C., the reaction was warmed to room temperature. After 1 hour at room temperature, the reaction was quenched with 2M HCl. The resultant solid was collected and washed with THF to provide This example. $^1$H NMR (300 MHz, DMSO-$d_6$) δ 12.11 (s, 1H) 8.65 (s, 1H) 8.12 (d, J=8.42 Hz, 1H) 7.78 (s, 1H) 7.43 (s, 1H) 7.26 (d, J=8.42 Hz, 1H) 4.59 (s, 2H).

EXAMPLE 21E

EXAMPLE 21D (0.284 g) was dissolved in 10 mL of dioxane and phosphorous tribromide (0.4 mL) was added. After stirring at room temperature for 24 hours, the resultant precipitate was collected, washed with water, and dried to provide This example. $^1$H NMR (400 MHz. DMSO-$d_6$) δ 11.95 (s, 1H) 8.54 (s, 1H) 8.10 (d, J=8.59 Hz, 1H) 7.61 (s, 1H) 7.44 (s, 1H) 7.38 (d, J=8.59 Hz, 1H) 4.80 (s, 3H).

EXAMPLE 21F 7-(pyrrolidin-1-ylmethyl)imidazo[1,2-a]quinoxalin-4(5H)-one

EXAMPLE 21E (60 mg) and pyrrolidine (110 mg) were stirred in 2 mL of acetonitrile at 60° for 24 hours. The solid was collected by filtration and washed with ethyl acetate to provide This example. $^1$H NMR (500 MHz, DMSO-d$_6$) δ 11.77 (s, 1H) 8.51 (d, J=1.22 Hz, 1H) 8.04 (d, J=8.24 Hz, 1H) 7.59 (d, J=1.22 Hz, 1H) 7.36 (d, J=1.22 Hz, 1H), 7.22 (dd, J=8.39, 1.68 Hz, 1H) 3.63 (s, 2H) 2.45 (s, 4H) 1.71 (m, 4H).

EXAMPLE 22

7-(piperidin-1-ylmethyl)imidazo[1,2-a]quinoxalin-4(5H)-one

This example was prepared as described in EXAMPLE 21F substituting piperidine (194 mg) for pyrrolidine. $^1$H NMR (500 MHz, DMSO-d$_6$) δ 11.79 (s, 1H) 8.51 (s, 1H) 8.05 (d, J=7.93 Hz, 1H) 7.59 (s, 1H) 7.36 (s, 1H) 7.22 (s, 1H) 3.48 (br s, 2H) 2.36 (m, 4H) 1.52 (s, 4H), 1.41 (s, 2H).

EXAMPLE 23

7-((dimethylamino)methyl)imidazo[1,2-a]quinoxalin-4(5H)-one

This example was prepared as described in EXAMPLE 21F substituting 2.0 M dimethylamine in THF (4 mL) for pyrrolidine. $^1$H NMR (400 MHz, DMSO-d$_6$) δ 11.91 (s, 1H) 8.55 (s, 1H) 8.11 (d, J=8.29 Hz, 1H) 7.60 (s, 1H) 7.37 (s, 1H) 7.27 (d, J=7.98 Hz, 1H) 3.70 (br s, 2H) 2.33 (br s, 6H).

EXAMPLE 24

7-(((cyclohexylmethyl)amino)methyl)imidazo[1,2-a]quinoxalin-4(5H)-one

This example was prepared as described in EXAMPLE 21F substituting aminomethycyclohexane (213 mg) for pyrrolidine. $^1$H NMR (500 MHz, DMSO-d$_6$) δ 11.90 (br s, 1H), 8.52 (s, 1H) 8.06 (d, J=8.24 Hz, 1H) 7.59 (s, 1H) 7.39 (s, 1H) 7.29 (d, J=7.93 Hz, 1H) 3.83 (s, 2H) 2.42 (m, 2H) 1.68 (m, 5H) 1.46 (m, 1H) 1.18 (m, 3H), 0.88 (m, 2H).

EXAMPLE 25

7-(morpholin4-ylmethyl)imidazo[1,2-a]quinoxalin-4(5H)-one

This example was prepared as described in EXAMPLE 21F substituting morpholine (244 mg) for pyrrolidine. $^1$H NMR (500 MHz, DMSO-d$_6$) δ 11.82 (s, 1H) 8.52 (s, 1H) 8.06 (d, J=8.24 Hz, 1H) 7.59 (s, 1H) 7.37 (s, 1H) 7.24 (d, J=7.93 Hz, 1H) 3.58 (m, 6H), 2.42 (m, 4H).

EXAMPLE 26

8-((dimethylamino)methyl)-5,6-dihydro-4H-pyrrolo[1,2-a][1,4]benzodiazepin-4-one

EXAMPLE 26A

2-Fluoro-5-formylbenzonitrile (1.62 g), triethyl orthoformate (2 mL) and ammonium nitrate (160 mg) were refluxed in 40 mL of ethanol for 24 hours. The reaction was concentrated and partitioned between ethyl acetate and water. The organic phase was washed with brine, dried over MgSO$_4$. filtered, and concentrated. The concentrate was purified on silica gel (40 g) eluting with 1:4 ethyl acetate:hexane to provide This example. $^1$H NMR (300 MHz, DMSO-d$_6$) δ 7.88 (dd, J=6.27, 2.20 Hz, 1H) 7.76 (m, 1H) 7.54 (t, J=8.99 Hz, 1H) 5.54 (s, 1H) 3.53 (m, 4H) 1.16 (t, J=6.95 Hz, 6H).

EXAMPLE 26B

Methyl 1H-pyrrole-2-carboxylate (263 mg), EXAMPLE 26A (0.470 mg) and cesium carbonate (862 mg) stirred in 8 mL DMF at 55° overnight. The reaction was concentrated and purified on silica gel (40 g) eluting with 1:4 ethyl acetate to provide This example. $^1$H NMR (500 MHz, DMSO-d$_6$) δ 7.90 (d, J=1.83 Hz, 1H) 7.80 (dd, J=8.24, 1.83 Hz, 1H) 7.58 (d, J=8.24 Hz, 1H) 7.34 (m, 1H) 7.11 (dd, J=3.97, 1.83 Hz, 1H) 6.42 (dd, J=3.97, 2.75 Hz, 1H) 5.63 (s, 1H) 3.64 (s, 3H), 3.58 (m, 4H) 1.19, (t, J=7.02 Hz, 6H).

EXAMPLE 26C

EXAMPLE 26B (343 mg) was dissolved in 7M ammonia in methanol (20 mL) and 50% Raney nickel in water (1.88 g) was added. The reaction was stirred vigorously for 5 hours and carefully filtered through Celite. This example was isolated after concentrating the filtrate. $^1$H NMR (300 MHz, DMSO-d$_6$) δ 8.30 (t, J=5.26 Hz, 1H) 7.50 (m, 4H) 6.88 (dd, J=3.73, 1.70 Hz, 1H) 6.41 (m, 1H) 5.54 (s, 1H) 3.54 (m, 4H) 1.17 (t, J=7.12 Hz, 6H).

EXAMPLE 26D

EXAMPLE 26C (371 mg) was stirred in 6 mL 1:2 2M aqueous HCl:THF for 1 hour. After concentrating, the concentrate was washed with diethyl ether to provide This example. $^1$H NMR (300 MHz, DMSO-d$_6$) δ 10.04 (s, 1H) 8.42 (t, J=5.43 Hz, 1H) 8.00 (m, 2H) 7.74 (m, 1H) 7.60 (m, 1H) 6.95 (dd, J=3.56, 1.86 Hz, 1H) 6.49 (m, 1H) 4.20 (d, J=5.43 Hz, 2H).

EXAMPLE 26E 8-((dimethylamino)methyl)-5,6-dihydro-4H-pyrrolo[1,2-a][1,4]benzodiazepin-4-one EXAMPLE 26D (57 mg), 2M dimethylamine in THF (1 mL), sodium triacetoxyborohydride (86 mg) and 6 drops acetic acid were stirred in 5 mL dichloroethane. After stirring at room temperature overnight, the reaction was concentrated and purified on silica gel (12 g) eluting with 10/90 2M ammonia in methanol/methylene chloride to isolate This example. $^1$H NMR (500 MHz, DMSO-d$_6$) δ 8.31 (t, J=5.34 Hz, 1H) 7.48 (m, 2H) 7.36 (m, 2H) 6.87 (dd, J=3.81, 1.68 Hz, 1H) 6.40 (m, 1H) 4.07 (d, J=5.19 Hz, 2H) 3.44 (s, 2H) 2.18 (s, 6H).

EXAMPLE 27

8-(pyrrolidin-1-ylmethyl)-5,6-dihydro-4H-pyrrolo[1,2-a][1,4]benzodiazepin-4-one

This example was prepared as described in EXAMPLE 26E substituting pyrrolidine (206 mg) for dimethylamine. $^1$H NMR (400 MHz, DMSO-d$_6$) δ 8.33 (t, J=5.37 Hz, 1H) 7.46 (m, 4H) 6.87 (dd, J=3.68, 1.84 Hz, 1H) 6.40 (m, 1H) 4.07 (d, J=5.22 Hz, 2H) 3.72 (br s, 2H) 2.57 (m, 4H) 1.74 (m, 4H).

EXAMPLE 28

8-((isopropylamino)methyl)-5,6-dihydro-4H-pyrrolo[1,2-a][1,4]benzodiazepin-4-one This example was prepared as described in EXAMPLE 26E substituting isopropylamine (133 mg) for dimethylamine. $^1$H NMR (400 MHz, DMSO-$d_6$) δ 8.37 (t, J=5.22 Hz, 1H) 7.48 (m, 4H) 6.87 (dd, J=3.68, 1.84 Hz, 1H) 6.40 (m, 1H) 4.06 (d, J=4.60 Hz, 2H) 3.81 (s, 2H) 3.25 (d, J=6.44 Hz, 1H) 2.82 (s, 1H) 1.06 (d, J=6.45 Hz, 6H).

EXAMPLE 29

8-((4-methylpiperazin-1-yl)methyl)-5,6-dihydro-4H-pyrrolo[1,2-a][1,4]benzodiazepin-4-one This example was prepared as described in EXAMPLE 26E substituting N-methylpiperazine (82 mg) for dimethylamine. $^1$H NMR (500 MHz, DMSO-$d_6$) δ 8.30 (t, J=5.49 Hz, 1H) 7.47 (m, 2H) 7.37 (m, 2H) 6.86 (dd, J=3.97, 1.83 Hz, 1H) 6.40 (m, 1H) 4.07 (d, J=5.19 Hz, 2H) 3.48 (s, 2H) 2.43 (m, 8H) 2.17 (s, 3H).

EXAMPLE 30

8-(((2-ethoxyethyl)(methyl)amino)methyl)-5,6-dihydro-4H-pyrrolo[1,2-a][1,4]benzodiazepin-4-one This example was prepared as described in EXAMPLE 26E substituting morpholine (174 mg) for dimethylamine. $^1$H NMR (400 MHz, DMSO-$d_6$) δ 8.32 (t, J=5.37 Hz, 1H) 7.48 (m, 2H) 7.39 (m, 2H) 6.87 (dd, J=3.84, 1.69 Hz, 1H) 6.40 (m, 1H) 4.07 (d, J=5.22 Hz, 2H) 3.58 (br s, 4H) 3.50 (br s, 2H) 2.37 (br s, 4H)

EXAMPLE 31

8-(((cyclohexylmethyl)amino)methyl)-5,6-dihydro-4H-pyrrolo[1,2-a][1,4]benzodiazepin-4-one This example was prepared as described in EXAMPLE 26E substituting aminomethylcyclohexane (96 mg) for dimethylamine. $^1$H NMR (400 MHz, DMSO-$d_6$) δ 8.36 (t, J=5.37 Hz, 1H) 7.49 (m, 4H) 6.87 (dd, J=3.68, 1.84 Hz, 1H) 6.41 (m, 1H) 4.06 (d, J=4.60 Hz, 2H) 3.85 (s, 2H) 2.46 (d, J=6.75 Hz, 2H) 1.76 (d, J=12.89 Hz, 2H) 1.65 (m, 3H) 1.49 (m, 1H) 1.15 (m, 3H) 0.89 (m, 2H).

EXAMPLE 32

8-((benzylamino)methyl)-5,6-dihydro-4H-pyrrolo[1,2-a][1,4]benzodiazepin-4-one

This example was prepared as described in EXAMPLE 26E substituting benzylamine (96 mg) for dimethylamine. $^1$H NMR (400 MHz, DMSO-$d_6$) δ 8.33 (t, J=5.52 Hz, 1H) 7.35 (m, 9H), 6.87 (dd, J=3.68, 1.84 Hz, 1H) 6.40 (m, 1H) 4.07 (d, J=4.91 Hz, 2H) 3.72 (s, 2H) 3.70 (s, 2H).

EXAMPLE 33

8-((cyclopentylamino)methyl)-5,6-dihydro-4H-pyrrolo[1,2-a][1,4]benzodiazepin-4-one This example was prepared as described in EXAMPLE 26E substituting cyclopentylamine (126 mg) for dimethylamine. $^1$H NMR (500 MHz, DMSO-$d_6$) δ 8.37 (t, J=5.34 Hz, 1H) 7.52 (m, 4H) 6.88 (dd, J=3.66, 1.83 Hz, 1H) 6.41 (m, 1H) 4.07 (d, J=4.27 Hz, 2H) 3.95 (s, 2H) 3.25 (m, 1H) 1.87 (m, 2H), 1.69 (m, 2H) 1.52 (m, 4H).

EXAMPLE 34

3-(pyrrolidin-1-ylmethyl)-7,8,9,10-tetrahydro-5H-pyrido[1,2-a]quinoxalin-6(6aH)-one

EXAMPLE 34A

Ethyl pipecolinate (7.6 mL), EXAMPLE 61A (8.8 g), and cesium carbonate (15.8 g) were stirred in 20 mL N, N-dimethylformamide at 55° C. for 24 hours. The reaction mixture was concentrated and purified on silica gel (120 g) eluting with 1:4 ethyl acetate:hexane to provide the title compound. MS (ESI) m/e 337 (M+H)$^+$.

EXAMPLE 34B

EXAMPLE 34A (5.43 g) was dissolved in 50 mL ethyl acetate. While stirring vigorously, 10% Pd/C (411 mg) was added, and the mixture was stirred under a $H_2$ balloon for 12 hours. The catalyst was removed by filtering through Celite. After concentrating, the resultant oil was purified on silica gel (90 g) eluting with 1:1 ethyl acetate:hexane to provide the title compound. MS (ESI) m/e 260 (M+H)$^+$.

EXAMPLE 34C

EXAMPLE 34B was dissolved in 25 mL anhydrous THF and cooled to 0° C. under $N_2$. To the cooled solution was added 1 M lithium aluminum hydride in THF (11 mL) over 5 minutes. After 0.5 hours, the mixture was warmed to room temperature. The mixture was quenched after 1 hour at room temperature with 2 M HCl. The solid was filtered and collected to provide the title compound. MS (ESI) m/e 232 (M+H)$^+$.

EXAMPLE 34D 3-(pyrrolidin-1-ylmethyl)-7,8,9,10-tetrahydro-5H-pyrido[1,2-a]quinoxalin-6(6aH)-one EXAMPLE 34C (94 mg), methanesulfonyl chloride (0.04 mL) and triethylamine (0.08 mL) were stirred in 10 mL methylene chloride for 6 hours. After concentrating, the residue was dissolved in 5 mL methylene chloride and pyrrolidine (0.2 mL) was added. The mixture was stirred for 12 hours and concentrated. The title compound was obtained after purification on silica gel (12 g) eluting with 5/95 2M ammonia in methanol/methylene chloride. $^1$H NMR (500 MHz. DMSO-$d_6$) δ 10.30 (s, 1H), 6.79 (m,3H), 3.70 (br d, 1H), 3.40 (s, 2H), 3.38 (m, 1H), 2.62 (m, 1H), 2.37 (m, 4H), 2.02 (m, 1H), 1.83 (m, 1H), 1.67 (m, 5H), 1.44 (m, 3H).

EXAMPLE 35

3-[(dimethylamino)methyl]-7,8,9,10-tetrahydro-5H-pyrido[1,2-a]quinoxalin-6(6aH)-one To a solution of EXAMPLE 34C (98 mg), 2M dimethylamine in THF (0.3 mL) and triphenylphosphine (165 mg) in 5 mL THF was added di-tert-butyl azodicaboxylate (145 mg). The mixture was stirred for 48 hours and was concentrated. The crude product was purified on silica gel (12 g) eluting with 2/98 2M ammonia in methanol/methylene chloride to provide the title compound. $^1$H NMR (500 MHz, DMSO-$d_6$) δ 10.32 (s, 1H), 6.77 (m, 3H), 3.71 (m, 1H), 3.38 (m, 1H), 3.22 (s, 2H), 2.62 (m, 1H), 2.10 (s, 6H), 2.04 (m, 1H), 1.83 (m, 1H), 1.68 (m, 1H), 1.46 (m, 3H).

EXAMPLE 36

3-[(cyclohexylamino)methyl]-7,8,9,10-tetrahydro-5H-pyrido[1,2-a]quinoxalin-6(6aH)-one The title compound was prepared as described in EXAMPLE 35, substituting cyclohexylamine for dimethylamine. $^1$H NMR (500 MHz, DMSO-$d_6$) δ 10.30 (s, 1H), 6.79 (m, 3H), 3.70 (d, 1H), 3.58 (s, 2H), 3.37 (m, 1H), 2.61 (m, 1H), 2.36 (m, 1H), 2.01 (m, 1H), 1.82 (m, 3H), 1.66 (m, 3H), 1.43 (m, 5H), 1.09 (m, 5H).

EXAMPLE 37

3-(piperidin-1-ylmethyl)-7,8,9,10-tetrahydro-5H-pyrido[1,2-a]quinoxalin-6(6aH)-one The title compound was prepared as described in EXAMPLE 35, substituting piperdine for dimethylamine. $^1$H NMR (500 MHz, DMSO-$d_6$) δ 10.30 (s, 1H), 6.75 (m, 3H), 3.70 (d, 1H), 3.39 (m, 1H), 3.26 (s, 2H), 2.62 (m, 1H), 2.27 (m, 4H), 2.02 (m, 1H), 1.83 (m, 1H), 1.68 (m, 1H), 1.43 (m, 9H).

EXAMPLE 38

3-[(isopropylamino)methyl]-7,8,9,10-tetrahydro-5H-pyrido[1,2-a]quinoxalin-6(6aH)-one The title compound was prepared as described in EXAMPLE 35, substituting isopropylamine for dimethylamine. $^1$H NMR (500 MHz, DMSO-$d_6$) δ 10.30 (s, 1H), 6.75 (m, 3H), 3.74 (d, 1H), 3.54 (s, 2H), 3.37 (m, 1H), 2.69 (m, 1H), 2.61 (m, 1H), 2.02 (m, 1H), 1.82 (m, 1H), 1.67 (m, 1H), 1.44 (m, 4H), 0.98 (d, 6H).

EXAMPLE 39

3-{[ethyl(methyl)amino]methyl}-7,8,9,10-tetrahydro-5H-pyrido[1,2-a]quinoxalin-6(6aH)-one The title compound was prepared as described in EXAMPLE 35, substituting N-ethylmethylamine for dimethylamine. $^1$H NMR (500 MHz, DMSO-$d_6$) δ 10.30 (s, 1H), 6.77 (m, 3H), 3.70 (d, 1H), 3.39 (m, 1H), 3.29 (s, 2H), 2.62 (m, 1H), 2.33 (q, 2H), 2.06 (s, 3H), 2.03 (m, 1H), 1.83 (m, 1H), 1.68 (m, 1H), 1.46 (m, 3H), 0.99 (t, 3H).

EXAMPLE 40

3-{[cyclohexyl(methyl)amino]methyl}-7,8,9,10-tetrahydro-5H-pyrido[1,2-a]quinoxalin-6(6aH)-one The title compound was prepared as described in EXAMPLE 35, substituting N-methylcyclohexylamine for dimethylamine. $^1$H NMR (500 MHz, DMSO-$d_6$) δ 10.28 (s, 1H), 6.78 (m, 3H) 3.70 (d, 1H), 3.39 (s, 2H) 3.36 (m, 1H), 2.61 (m, 1H), 2.36 (m, 1H), 2.06 (s, 3H), 2.01 (m, 1H), 1.75 (m, 6H), 1.48 (m, 4H), 1.16 (m, 5H).

EXAMPLE 41

3-{[isopropyl(methyl)amino]methyl}-7,8,9,10-tetrahydro-5H-pyrido[1,2-a]quinoxalin-6(6aH)-one The title compound was prepared as described in EXAMPLE 35, substituting N-methylisopropylamine for dimethylamine. $^1$H NMR (500 MHz, DMSO-$d_6$) δ 10.29 (s, 1H), 6.79 (m, 2H), 6.73 (d, 1H), 3.70 (d, 1H), 3.38 (m, 1H), 3.30 (s, 2H), 2.81 (m, 1H), 2.61 (m, 1H), 2.02 (m, 4H), 1.83 (m, 1H), 1.67 (m, 1H), 1.44 (m, 3H), 0.98 (d, 6H).

EXAMPLE 42

3-[(4-methylpiperazin-1-yl)methyl]-7,8,9,10-tetrahydro-5H-pyrido[1,2-a]quinoxalin-6(6aH)-one The title compound was prepared as described in EXAMPLE 35, substituting N-methylpiperazine for dimethylamine. $^1$H NMR (400 MHz, DMSO-$d_6$) δ 10.32 (s, 1H), 6.75 (m, 3H), 3.70 (d, 1H), 3.39 (m, 1H), 3.29 (s, 2H) 2.61 (m, 1H), 2.31 (m, 7H), 2.16 (s, 3H), 2.00 (m, 1H), 1.82 (m, 1H), 1.67 (m, 1H), 1.41 (m, 4H).

EXAMPLE 43

7-(pyrrolidin-1-ylmethyl)-1,2,3,3a-tetrahydropyrrolo[1,2-a]quinoxalin-4(5H)-one

EXAMPLE 43A

Methyl pyrrolidine-2-carboxylate hydrochloride (3.13 g), EXAMPLE 61A (3.76 g), and cesium carbonate (12.2 g) were stirred in 15 mL N,N-dimethylformamide at 60° C. for 12 hours. The reaction mixture was filtered through Celite and concentrated. The crude product was purified on silica gel (90 g) eluting with 1:4 ethyl acetate:hexane. MS (ESI) m/e 308 (M+H)$^+$.

EXAMPLE 43B

EXAMPLE 43A (4.66 g) was dissolved in 50 mL methanol. While it was stirred vigorously, 10% Pd/C (460 mg) was added, and the mixture was stirred under a H$_2$ balloon for 12 hours. The catalyst was removed by filtering the mixture through Celite. After concentrating the filtrate, the crude product was used without any further purification. MS (ESI) m/e 246 (M+H)$^+$.

EXAMPLE 43C

EXAMPLE 43B (122 mg) was dissolved in 10 mL anhydrous THF and cooled to 0° C. To the cooled solution was added 1M lithium aluminum hydride (1.2 mL). After stirring for 0.5 hours at 0° C., the mixture was warmed to room temperature and quenched after 1 hour with 2M HCl. The mixture was concentrated and purified on silica gel (4 g) eluting with 10/90 2M ammonia in methanol/methylene chloride. MS (ESI) m/e 219 (M+H)$^+$.

EXAMPLE 43D 7-(pyrrolidin-1-ylmethyl)-1,2,3,3a-tetrahydropyrrolo[1,2-a]quinoxalin-4(5H)-one To a solution of EXAMPLE 43C (82 mg), pyrrolidine (131 mg) and triphenylphosphine (148 mg) in 5 mL THF was added di-tert-butyl azodicaboxylate (137 mg). The mixture was stirred for 48 hours and concentrated. The crude product was purified on silica gel (12 g) eluting with 10/90 2M ammonia in methanol/methylene chloride to provide the title compound. $^1$H NMR (500 MHz, DMSO-d$_6$) δ 10.26 (s, 1H), 6.79 (m, 2H), 6.50 (d, 1H), 3.51 (m, 1H), 3.42 (s, 2H), 3.38 (m, 1H), 3.02 (m, 1H), 2.39 (br s, 4H), 2.10 (m, 1H), 1.94 (m, 3H), 1.67 (br s, 4H).

EXAMPLE 44

7-[(dimethylamino)methyl]-1,2,3,3a-tetrahydropyrrolo[1,2-a]quinoxalin-4(5H)-one

The title compound was prepared as described in EXAMPLE 43, substituting dimethylamine for pyrrolidine. $^1$H NMR (500 MHz, DMSO-d$_6$) δ 10.26 (s, 1H), 6.78 (m, 2H), 6.51 (d, 1H), 3.53 (m, 1H), 3.39 (m, 1H), 3.32 (s, 2H), 3.03 (m, 1H), 2.10 (s, 6H), 2.07 (m, 1H), 1.91 (m, 3H).

EXAMPLE 45

7-(piperidin-1-ylmethyl)-1,2,3,3a-tetrahydropyrrolo[1,2-a]quinoxalin-4(5H)-one

The title compound was prepared as described in EXAMPLE 43, substituting piperidine for pyrrolidine. $^1$H NMR (500 MHz, DMSO-d$_6$) δ 10.25 (s, 1H), 6.77 (m, 2H), 6.51 (d, 1H), 3.52 (m, 1H), 3.39 (m, 1H), 3.26 (s, 2H), 3.03 (m, 1H), 2.27 (br s, 4H), 2.10 (m, 1H), 1.94 (m, 3H), 1.46 (m, 4H), 1.37 (m, 2H).

EXAMPLE 46

7-{[ethyl(methyl)amino]methyl}-1,2,3,3a-tetrahydropyrrolo[1,2-a]quinoxalin-4(5H)-one The title compound was prepared as described in EXAMPLE 43, substituting N-ethylmethylamine for pyrrolidine. $^1$H NMR (500 MHz, DMSO-d$_6$) δ 10.26 (s, 1H), 6.78 (m, 2H), 6.51 (d, 1H), 3.52 (m, 1H), 3.40 (m, 1H), 3.31 (s, 2H), 3.03 (m, 1H), 2.35 (m, 2H), 2.10 (m, 1H), 2.06 (s, 3H), 1.94 (m 3H), 1.00 (t, 3H).

EXAMPLE 47

7-{[cyclohexyl(methyl)amino]methyl}-1,2,3,3a-tetrahydropyrrolo[1,2-a]quinoxalin-4(5H)-one The title compound was prepared as described in EXAMPLE 43, substituting N-methylcyclohexylamine for pyrrolidine. $^1$H NMR (500 MHz, DMSO-d$_6$) δ 10.24 (s, 1H), 6.78 (m, 2H), 6.50 (d, 1H), 3.51 (m, 1H), 3.39 (m, 3H), 3.02 (m, 1H), 2.36 (m, 1H), 2.09 (m, 4H), 1.94 (m, 3H), 1.75 (m, 4H), 1.57 (m, 1H), 1.16 (m, 5H).

EXAMPLE 48

7-[(4-methylpiperazin-1-yl)methyl]-1,2,3,3a-tetrahydropyrrolo[1,2-a]quinoxalin-4(5H)-one The title compound was prepared as described in EXAMPLE 43, substituting N-methylpiperazine for pyrrolidine. $^1$H NMR (500 MHz, DMSO-d$_6$) δ 10.26 (s, 1H), 6.77 (m, 2H), 6.50 (d, 1H), 3.51 (m, 1H), 3.40 (m, 1H), 3.29 (s, 2H), 3.03 (m, 1H), 2.30 (m, 4H), 2.14 (s, 3H), 2.09 (m, 1H), 1.94 (m, 4H), 1.39 (m, 3H).

EXAMPLE 49

7-{[benzyl(methyl)amino]methyl}-1,2,3,3a-tetrahydropyrrolo[1,2-a]quinoxalin-4(5H)-one The title compound was prepared as described in EXAMPLE 43, substituting N-methylbenzylamine for pyrrolidine. $^1$H NMR (500 MHz, DMSO-d$_6$) δ 10.30 (s, 1H), 7.32 (m, 4H), 7.23 (m, 1H), 6.87 (s, 1H), 6.83 (d, 1H), 6.53 (d, 1H), 3.53 (m, 1H), 3.44 (s, 2H), 3.41 (m, 1H), 3.36 (s, 2H), 3.05 (m, 1H), 2.10 (m, 1H), 2.04 (s, 3H), 1.93 (m, 3H).

EXAMPLE 50

7-{[isopropyl(methyl)amino]methyl}-1,2,3,3a-tetrahydropyrrolo[1,2-a]quinoxalin-4(5H)-one The title compound was prepared as described in EXAMPLE 43, substituting N-methyisopropylamine for pyrrolidine. $^1$H NMR (500 MHz, DMSO-d$_6$) δ 10.24 (s, 1H), 6.80 (s, 1H), 6.78 (d, 1H), 6.51 (d, 1H), 3.50 (m, 1H), 3.39 (m, 1H), 3.30 (s, 2H), 3.01 (m, 1H), 2.80 (m, 1H), 2.09 (m, 1H), 2.01 (s, 3H) 1.94 (m, 3H), 0.97 (d, 6H).

EXAMPLE 51

N-cyclopropyl-N-[(4-oxo4,5-dihydropyrrolo[1,2-a]quinoxalin-8-yl)methyl]methanesulfonamide To a solution of EXAMPLE 12 (26 mg) and triethylamine (25 μL) in 1 mL dioxane was added methanesulfonyl chloride (5.53 μL). The mixture was stirred for 24 hours and concentrated. The title compound was purified by RP-HPLC using a gradient elution of 10/90 to 70/30 acetonitrile/0.1% TFA in water at 254 nm over 30 minutes. The free base was isolated after eluting from an ion exchange column (10 g). $^1$H NMR (500 MHz, DMSO-d$_6$) δ 11.28 (s, 1H), 8.14 (m, 1H), 7.95 (s, 1H), 7.29 (s, 2H), 7.03 (m, 1H), 6.70 (m, 1H), 4.41 (s, 2H), 2.96 (s, 3H), 2.46 (m, 1H), 0.68 (d, 4H).

EXAMPLE 52

7-[(2-oxopyrrolidin-1-yl)methyl]pyrrolo[1,2-a]quinoxalin-4(5H)-one

EXAMPLE 1D (45 mg), ethyl 4-aminobutanoate hydrochloride (49 mg), and triethylamine (0.04 mL) were dissolved in 5 mL anhydrous methanol. Sodium borohydride (8 mg) was added, and the mixture was stirred at 45° C. for 12 hours. After concentrating in vacuo, the crude mixture was purified by RP-HPLC using a gradient elution of 10/90 to 50/50 aceotnitrile/0.1% TFA in water at 254 nm over 30 minutes. The title compound was obtained as the free base after eluting from an ion exchange column (5 g). $^1$H NMR (500 MHz, DMSO-d$_6$) δ 11.20 (br s, 1H), 8.16 (m, 1H), 8.01 (d, 1H), 7.15 (s, 1H), 7.07 (d, 1H), 7.02 (m, 1H), 6.68 (t, 1H), 4.40 (s, 2H), 3.26 (t, 2H), 2.31 (t, 2H), 1.95 (t, 2H).

EXAMPLE 53

N-cyclobutyl-N-[(4-oxo-4,5-dihydropyrrolo[1,2-a]quinoxalin-8-yl)methyl]ethanesulfonamide The title compound was prepared as described in EXAMPLE 51, substituting EXAMPLE 16 for EXAMPLE 12 and substituting ethanesulfonyl chloride for methanesulfonyl chloride. $^1$H NMR (500 MHz, DMSO-$d_6$) δ 11.25 (s, 1H), 8.06 (m, 1H), 7.95 (s, 1H), 7.28 (s, 2H), 7.03 (m, 1H), 6.70 (t, 1H), 4.54 (s, 2H), 4.25 (p, 1H), 3.09 (q, 2H), 2.13 (m, 2H), 2.02 (m, 2H), 1.15 (m, 2H), 1.21 (t, 3H).

EXAMPLE 54

N-isopropyl-N-[(4-oxo-4,5-dihydropyrrolo[1,2-a]quinoxalin-8-yl)methyl]benzenesulfonamide The title compound was prepared as described in EXAMPLE 51, substituting EXAMPLE 13 for EXAMPLE 12 and substituting benzene sulfonyl chloride for methanesulfonyl chloride. The title compound was isolated after purification on silica gel (12 g) eluting with 2/98 ethanol/methylene chloride. $^1$H NMR (500 MHz, DMSO-$d_6$) δ 11.26 s, 1H), 8.02 (m, 1H), 7.97 (s, 1H), 7.88 (s, 2H), 7.69 (d, 1H), 7.62 (t, 2H), 7.36 (d, 1H), 7.28 (d, 1H), 7.03 (d, 1H), 6.70 (d, 1H), 4.44 (s, 2H), 4.12 (sept, 1H), 0.89 (d, 6H).

EXAMPLE 55

N-cyclobutyl-N-[(4-oxo-4,5-dihydropyrrolo[1,2-a]quinoxalin-7-yl)methyl]acetamide The title compound was prepared as described in EXAMPLE 51, substituting EXAMPLE 3 for EXAMPLE 12 and substituting acetic anhydride for methanesulfonyl chloride. The title compound was isolated after purification on silica gel (12 g) eluting with 5/95 2M ammonia in methanol/methylene chloride. $^1$H NMR (300 MHz, DMSO-$d_6$) δ 10.86 (br s, 1H), 8.02 (m, 1H), 7.89 (d, 1H), 7.15 (s, 1H), 7.03 (s, 1H), 7.00 (m, 1H), 6.63 (m, 1H), 4.63 (s, 2H), 4.50 (m, 1H), 2.09 (m, 4H), 2.03 (s, 3H), 1.59 (m, 2H).

EXAMPLE 56

N-cyclopropyl-N-[(4-oxo-4,5-dihydropyrrolo[1,2-a]quinoxalin-7-yl)methyl]methanesulfonamide The title compound was prepared as described in EXAMPLE 51, substituting EXAMPLE 5 for EXAMPLE 12. $^1$H NMR (300 MHz, DMSO-$d_6$) δ 11.24 (s, 1H), 8.16 (m, 1H), 8.02 (d, 1H), 7.32 (s, 1H), 7.17 (d, 1H), 7.03 (s, 1H), 6.68 (t, 1H), 4.39 (s, 2H), 2.96 (s, 3H), 2.47 (s, 1H), 0.68 (m, 4H).

EXAMPLE 57

8-(piperidin-1-ylmethyl)-5,6-dihydro-4H-pyrrolo[1,2-a][1,4]benzodiazepin4-one

The title compound was prepared as described in EXAMPLE 26E, substituting piperidine for dimethylamine. The title compound was isolated as the TFA salt after purification by RP- HPLC using a gradient elution of 10/90 to 90/10 acetonitrilie/0.1% TFA in water at 254 nm over 30 minutes. $^1$H NMR (500 MHz, DMSO-$d_6$) δ 8.40 (t, 1H), 7.58 (m, 4H), 6.92 (m, 1H), 6.45 (m, 1H), 4.33 (d, 2H), 4.10 (d, 2H), 3.36 (br d, 2H), 2.90 (m, 2H), 1.83 (br d, 2H), 1.65 (m, 3H), 1.37 (m, 1H).

EXAMPLE 58

8-[(cyclohexylamino)methyl]-5,6-dihydro-4H-pyrrolo[1,2-a][1,4]benzodiazepin4-one The title compound was prepared as described in EXAMPLE 26E, substituting cyclohexylamine for dimethylamine. The title compound was isolated as the TFA salt after purification by RP-HPLC using a gradient elution of 10/90 to 90/10 acetonitrilie/0.1% TFA in water at 254 nm over 30 minutes. $^1$H NMR (500 MHz, DMSO-$d_6$) δ 8.42 (t, 1H), 7.56 (m, 4H), 6.91 (m, 1H), 6.44 (m, 1H), 4.22 (t, 2H), 4.09 (br s, 2H), 3.04 (m, 1H), 2.10 (br d, 2H), 1.79 (br d, 2H), 1.63 (br d, 1H), 1.29 (m, 4H), 1.13 (m, 1H).

EXAMPLE 59

Methyl N-[(4-oxo4,5-dihydropyrrolo[1,2-a]quinoxalin-7-yl)methyl]glycinate

The title compound was prepared as described in EXAMPLE 1E, substituting glycine methyl ester hydrochloride for cyclohexylamine. $^1$H NMR (400 MHz, DMSO-$d_6$) δ 11.46 (s, 1H), 9.51 (br s, 1H), 8.20 (m, 1H), 8.13 (d, 1H), 7.37 (s, 1H), 7.33 (d, 1H), 7.06 (d, 1H), 6.73 (q, 1H), 4.21 (s, 2H), 4.02 (s, 2H), 3.76 (s, 3H).

EXAMPLE 60

N-[(4-oxo-4,5-dihydropyrrolo[1,2-a]quinoxalin-7-yl)methyl]glycine

EXAMPLE 59 (123 mg) was dissolved in 5 mL THF and 1 mL methanol to which 2 mL 1M lithium hydroxide was added. After stirring at room temperature for 12 hours, the solution was neutralized with 1M HCl. The solid was collected and dried to provide the title compound. $^1$H NMR (500 MHz, DMSO-$d_6$) δ 7.99 (s, 1H), 7.93 (d, 1H), 7.40 (s, 1H), 7.30 (d, 1H), 7.06 (m, 1H), 6.64 (m, 1H), 4.20 (s, 2H), 3.81 (s, 2H).

EXAMPLE 61

4-oxo-N-(2-pyrrolidin-1-ylethyl)-4,5-dihydropyrrolo[1,2-a]quinoxaline-7-carboxamide

EXAMPLE 61A

A solution of 4-fluoro-3-nitrobenzoic acid (11.9 g) in 100 mL anhydrous methanol was cooled to 0° C. Thionyl chloride (9.5 mL) was added slowly over 10 minutes and the mixture was refluxed for 4 hours. The mixture was concentrated to provide the title compound. $^1$H NMR (300 MHz, DMSO-$d_6$) δ 8.58 (dd, 1H), 8.35 (m, 1H), 7.75 (m, 1H), 3.01 (s, 3H).

EXAMPLE 61B

The title compound was prepared as described in EXAMPLE 34A, substituting methyl 1H-pyrrole-2-carboxylate for ethyl pipecolinate. MS (ESI) m/e 304(M+H)$^+$.

EXAMPLE 61C

The title compound was prepared as described in EXAMPLE 43B, substituting EXAMPLE 61B for EXAMPLE 43A. The title compound was isolated after purification on silica gel (120 g) eluting with 4:1 ethyl acetate: hexanes. MS (ESI) m/e 242(M+H)+.

EXAMPLE 61D

EXAMPLE 61C (0.638 g) was dissolved in 25 mL 5:1 THF:methanol and 1M lithium hydroxide (13 mL) was added. The mixture was stirred for 12 hours then neutralized with 2 M HCl. The resultant solid was collected and recrystallized from hot methanol. MS (ESI) m/e 229(M+H)+.

EXAMPLE 61E 4-oxo-N-(2-pyrrolidin-1-ylethyl)-4,5-dihydropyrrolo[1,2-a]quinoxaline-7-carboxamide EXAMPLE 61D (70 mg), N,N-diisopropylethylamine (0.1 mL) and 2-(1H-7-azabenzotriazol-1-yl)-1,1,3,3-tetramethyl uronium hexafluorophosphate methanaminium (HATU) (154 mg) were stirred in 1 mL N,N-dimethylformamide for 0.5 hours and 2-(pyrrolidin-1-yl)ethanamine (82 mg) was added. After 24 hours. the mixture was concentrated. The title compound was isolated after purification by RP-HPLC using a gradient elution of 5/95 to 70/30 acetonitrilie/0.1% TFA in water at 254 nm over 30 minutes. $^1$H NMR (500 MHz, DMSO-$d_6$) δ 11.35 (br s, 1H), 8.49 (t, 1H), 8.23 (s, 1H), 8.12 (d, 1H), 7.79 (s, 1H), 7.68 (d, 1H), 7.07 (d, 1H), 6.73 (m, 1H), 3.39 (m, 2H), 2.61 (t, 2H), 2.52 (m, 4H), 1.69 (4H).

EXAMPLE 62

7-{[(2-pyrrolidin-1-ylethyl)amino]methyl}pyrrolo[1,2-a]quinoxalin-4(5H)-one

The title compound was prepared as described in EXAMPLE 1E, substituting 2-(pyrrolidin-1-yl)ethanamine for cyclohexylamine. The title compound was purified by RP-HPLC using a gradient elution of 5/95 to 70/30 acetonitrilie/0.1% TFA in water at 254 nm over 30 minutes. The free base was isolated after eluting from an ion exchange column (10 g). $^1$HNMR (400 MHz, DMSO-$d_6$) δ 11.18 (br s, 1H), 8.14 (m, 1H), 7.97 (d, 1H), 7.27 (s, 1H), 7.16 (d, 1H), 7.01 (m, 1H), 6.66 (m, 1H), 3.74 (s, 2H), 2.61 (m, 2H), 2.53 (m, 2H), 2.43 (m, 4H), 1.66 (m, 4H).

EXAMPLE 63

N-(3-morpholin-4-ylpropyl)-4-oxo-4,5-dihydropyrrolo[1,2-a]quinoxaline-7-carboxamide The title compound was prepared as described as in EXAMPLE 61E, substituting 3-morpholinopropan-1-amine for 2-(pyrrolidin-1-yl)ethanamine. The title compound was isolated after purification on silica gel (12 g) eluting with 10/90 2M ammonia in methanol/methylene chloride. $^1$H NMR (500 MHz, DMSO-$d_6$) δ 11.36 (s, 1H), 8.57 (t, 1H), 8.24 (s, 1H), 8.13 (d, 1H), 7.78 (s, 1H), 7.68 (dd, 1H), 7.07 (m, 1H), 6.73 (m, 1H), 3.58 (m, 4H), 3.30 (m, 2H), 2.37 (m, 6H), 1.70 (t, 2H).

EXAMPLE 64

N-(2-morpholino-2-oxoethyl)-4-oxo-4,5-dihydropyrrolo[1,2-a]quinoxaline-7-carboxamide The title compound was prepared as described as in EXAMPLE 61, substituting 2-amino-1-morpholinoethanone hydrochloride for 2-(pyrrolidin-1-yl)ethanamine. $^1$H NMR (500 MHz, DMSO-$d_6$) δ 11.37 (s, 1H), 8.62 (t, 1H), 8.24 (s, 1H), 8.14 (d, 1H), 7.81 (s, 1H), 7.72 (dd, 1H), 7.07 (m, 1H), 6.73 (t, 1H), 4.16 (d, 2H), 3.61 (m, 4H), 3.48 (m, 4H).

EXAMPLE 65

7-({[2-(dimethylamino)ethyl]amino}methyl)pyrrolo[1,2-a]quinoxalin-4(5H)-one

The title compound was prepared as described in EXAMPLE 1E, substituting $N^1$, $N^1$-dimethylethane-1,2-diamine for cyclohexylamine. $^1$H NMR (500 MHz, DMSO-$d_6$) δ 11.25 (br s, 1H), 8.16 (s, 1H), 7.99 (d, 1H), 7.29 (s, 1H), 7.19 (d, 1H), 7.02 (m, 1H), 6.67 (t, 1H), 3.78 (s,2H), 2.64 (t, 2H), 2.43 (t, 2H) 2.18 (s, 6H).

EXAMPLE 66

N-[3-(4-methylpiperazin-1-yl)propyl]-4-oxo4,5-dihydropyrrolo[1,2-a]quinoxaline-7-carboxamide The title compound was prepared as described as in EXAMPLE 61E, substituting 3-(4-methylpiperazin-1-yl)propan-1-amine for 2-(pyrrolidin-1-yl)ethanamine. $^1$H NMR (500 MHz, DMSO-$d_6$) δ 11.37 (s, 1H), 8.57 (t, 1H), 8.24 (s, 1H), 8.12 (d, 1H), 7.79 (s, 1H), 7.67 (dd, 1H), 7.06 (m, 1H), 6.72 (t, 1H), 3.29 (m, 4H), 2.36 (m, 8H), 2.10 (s, 3H), 1.69 (t, 2H).

EXAMPLE 67

7-{[(3-morpholin-4-ylpropyl)amino]methyl}pyrrolo[1,2-a]quinoxalin-4(5H)-one

The title compound was prepared as described in EXAMPLE 1E, substituting 3-morpholinopropan-1-amine for cyclohexylamine. $^1$H NMR (500 MHz, DMSO-$d_6$) δ 11.22 (br s, 1H), 8.15 (s, 1H), 7.97 (d, 1H), 7.27 (s, 1H), 7.16 (d, 1H), 7.01 (m, 1H), 6.67 (m, 1H), 3.72 (s, 2H), 3.53 (m, 4H), 2.53 (t, 2H), 2.32 (m, 6H), 1.59 (t, 2H).

EXAMPLE 68

N-[2-(dimethylamino)ethyl]-4-oxo-4,5-dihydropyrrolo[1,2-a]quinoxaline-7-carboxamide The title compound was prepared as described as in EXAMPLE 61E, substituting $N^1$, $N^1$-dimethylethane-1,2-diamine for 2-(pyrrolidin-1-yl)ethanamine. $^1$H NMR (400 MHz, DMSO-$d_6$) δ 1135 (br s, 1H), 8.44 (t, 1H), 8.23 (m, 1H), 8.12 (d, 1H), 7.79 (s, 1H), 7.66 (dd, 1H), 7.06 (m, 1H), 6.73 (t, 1H), 3.38 (q, 2H), 2.43 (t, 2H), 2.20 (s, 6H).

EXAMPLE 69

7-{[(3-piperidin-1-ylpropyl)amino]methyl}pyrrolo[1,2-a]quinoxalin-4(5H)-one

The title compound was prepared as described in EXAMPLE 1E, substituting 3-(piperidin-1-yl)propan-1-amine for cyclohexylamine. $^1$H NMR (400 MHz, DMSO-d$_6$) δ 11.22 (s, 1H), 8.17 (m, 1H), 7.99 (d, 1H), 7.34 (s, 1H), 7.20 (dd, 1H), 7.03 (m, 1H), 6.68 (t, 1H), 3.61 (s, 2H), 2.93 (s, 2H), 2.52 (m, 6H), 2.45 (m, 2H). 1.87 (m, 2H), 1.68 (m, 2H), 1.50 (m, 2H).

EXAMPLE 70

4-oxo-N-(3-piperidin-1-ylpropyl)-4,5-dihydropyrrolo[1,2-a]quinoxaline-7-carboxamide The title compound was prepared as described as in EXAMPLE 61E, substituting 3-(piperidin-1-yl)propan-1-amine for 2-(pyrrolidin-1-yl)ethanamine. $^1$H NMR (400 MHz, DMSO-d$_6$) δ 11.37 (br s, 1H), 8.58 (t, 1H), 8.24 (s, 1H), 8.13 (d, 1H), 7.79 (s, 1H), 7.65 (dd, 1H), 7.06 (m, 1H), 6.73 (m, 1H), 3.30 (m, 2H), 2.32 (m, 6H), 1.69 (m, 2H), 1.48 (m, 4H), 1.38 (m, 2H).

EXAMPLE 71

7-{[(2-piperidin-1-ylethyl)amino]methyl}pyrrolo[1,2-a]quinoxalin-4(5H)-one

The title compound was prepared as described in EXAMPLE 1E, substituting 2-(piperidin-1-yl)ethanamine for cyclohexylamine. The title compound was purified by RP-HPLC eluting with 5/95 acetonitrilie/0.1% TFA in water at 254 nm. The free base was isolated after eluting from an ion exchange column (10 g). $^1$H NMR (500 MHz, DMSO-d$_6$) δ 11.21 (br s, 1H), 8.14 (m, 1H), 7.97 (d, 1H), 7.26 (s, 1H), 7.15 (d, 1H), 7.01 (m, 1H), 6.67 (m, 1H), 3.37 (s, 2H), 2.59 (t, 2H), 2.36 (t, 2H), 2.30 (m, 4H), 1.47 (m, 4H), 1.36 (m, 2H).

EXAMPLE 72

7-({[4-(dimethylamino)cyclohexyl]amino}methyl)pyrrolo[1,2-a]quinoxalin-4(5H)-one The title compound was prepared as described in EXAMPLE 1E, substituting $N^1$, $N^1$-dimethylcyclohexane-1,4-diamine for cyclohexylamine. The title compound was purified by RP-HPLC eluting with 2/98 acetonitrilie/0.1% TFA in water at 254 nm. The free base was isolated after eluting from an ion exchange column (10 g). $^1$H NMR (500 MHz, DMSO-d$_6$) δ 11.19 (br s, 1H), 8.14 (m, 1H), 7.96 (d, 1H), 7.29 (d, 1H), 7.18 (t, 1H), 7.01 (m, 1H), 6.67 (m, 1H), 3.73 (d, 2H), 2.16 (d, 6H), 2.10 (m, 2H), 1.95 (m, 1H), 1.77 (m, 1H), 1.68 (m, 2H), 1.43 (m, 2H), 1.08 (m, 2H).

EXAMPLE 73

4-oxo-N-(2-oxo-2-(pyrrolidin-1-yl)ethyl)-4,5-dihydropyrrolo[1,2-a]quinoxaline-7-carboxamide The title compound was prepared as described as in EXAMPLE 61E, substituting 2-amino-1-(pyrrolidin-1-yl)ethanone for 2-(pyrrolidin-1-yl)ethanamine. $^1$H NMR (500 MHz, DMSO-d$_6$) δ 11.39 (s, 1H), 8.65 (t, 1H), 8.24 (m, 1H), 8.15 (d, 1H), 7.82 (s, 1H), 7.73 (d, 1H), 7.07 (m, 1H), 6.73 (m, 1H), 4.04 (d, 2H), 3.49 (t, 2H), 3.31 (t, 2H), 1.92 (p, 2H), 1.79 (p, 2H).

EXAMPLE 74

N-[4-(dimethylamino)cyclohexyl]-4-oxo4,5-dihydropyrrolo[1,2-a]quinoxaline-7-carboxamide The title compound was prepared as described as in EXAMPLE 61E, substituting $N^1$,$N^1$-dimethylcyclohexane-1,4-diamine for 2-(pyrrolidin-1-yl)ethanamine. $^1$H NMR (500 MHz, DMSO-d$_6$) δ 8.33 (br s, 1H), 8.29 (d, 1H), 8.24 (m, 1H), 8.10 (m, 1H), 7.78 (s, 1H), 7.69 (d, 1H), 7.07 (m, 1H), 6.73 (m, 1H), 3.74 (m, 1H), 2.22 (s, 6H), 2.19 (m, 1H), 1.90 (m, 2H), 1.85 (m, 2H), 1.34 (m, 4H).

EXAMPLE 75

4-oxo-N-[3-(piperidin-1-ylsulfonyl)phenyl]4,5-dihydropyrrolo[1,2-a]quinoxaline-7-carboxamide The title compound was prepared as described as in EXAMPLE 61E, substituting 3-(piperidin-1-ylsulfonyl)aniline for 2-(pyrrolidin-1-yl)ethanamine. $^1$H NMR (500 MHz, DMSO-d$_6$) δ 11.46 (s, 1H), 10.67 (s, 1H), 8.30 (m, 1H), 8.24 (m, 2H), 8.13 (d, 1H), 7.87 (m, 2H), 7.64 (t, 1H), 7.45 (d, 1H), 7.10 (m, 1H), 6.76 (m, 1H), 2.93 (m, 4H), 1.56 (m, 4H), 1.39 (m, 2H).

EXAMPLE 76

7-((2-oxo-2-(pyrrolidin-1-yl)ethylamino)methyl)pyrrolo[1,2-a]quinoxalin-4(5H)-one The title compound was prepared as described in EXAMPLE 1E, substituting 2-amino-1-(pyrrolidin-1-yl)ethanone for cyclohexylamine. $^1$H NMR (500 MHz, DMSO-d$_6$) δ 11.23 (s, 1H), 8.16 (s, 1H), 7.99 (d, 1H), 7.31 (s, 1H), 7.21 (d, 1H), 7.02 (m, 1H), 6.68 (m, 1H), 3.70 (s, 2H), 3.34 (s, 2H), 3.21 (m, 6H), 1.72 (m, 2H).

EXAMPLE 77

4-oxo-N-(pyridin-4-ylmethyl)-4,5-dihydropyrrolo[1,2-a]quinoxaline-7-arboxamide

The title compound was prepared as described as in EXAMPLE 61E, substituting pyridin4-ylmethanamine for 2-(pyrrolidin-1-yl)ethanamine. $^1$H NMR (500 MHz, DMSO-d$_6$) δ 11.40 (s, 1H), 9.21 (t, 1H) 8.52 (m, 2H) 8.26 (s, 1H), 8.17 (d, 1H), 7.85 (s, 1H), 7.78 (dd, 1H), 7.34 (d, 2H), 7.07 (m, 1H), 6.74 (m, 1H), 4.52 (d, 2H).

EXAMPLE 78

4-oxo-N-(2-thiomorpholin-4-ylethyl)-4,5-dihydropyrrolo[1,2-a]quinoxaline-7-carboxamide The title compound was prepared as described as in EXAMPLE 61E, substituting 2-thiomorpholinoethanamine for 2-(pyrrolidin-1-yl)ethanamine. $^1$H NMR (500 MHz, DMSO-d$_6$) δ 11.39 s, 1H), 8.46 (t, 1H), 8.24 (s, 1H), 8.13 (d, 1H), 7.78 (s, 1H), 7.65 (dd, 1H), 7.06 (m, 1H), 6.73 (m, 1H), 3.38 (m, 2H), 2.73 (m, 4H), 2.62 (m, 4H), 2.53 (m, 2H).

EXAMPLE 79

N,N-dimethyl-4-oxo-4,5-dihydropyrrolo[1,2-a]quinoxaline-7-carboxamide

The title compound was prepared as described as in EXAMPLE 61E, substituting dimethylamine for 2-(pyrrolidin-1-yl)ethanamine. $^1$H NMR (500 MHz, DMSO-d$_6$) δ 11.32 (br s, 1H), 8.23 (s, 1H) 8.09 (d, 1H), 7.32 (s, 1H), 7.25 (dd, 1H), 7.06 (m, 1H), 6.72 (m, 1H), 2.99 (br s, 3H), 2.96 (br s, 3H).

EXAMPLE 80

N-(1-ethylpiperidin-3-yl)4-oxo-4,5-dihydropyrrolo[1,2-a]quinoxaline-7carboxamide The title compound was prepared as described as in EXAMPLE 61E, substituting 1-ethylpiperidin-3-amine for 2-(pyrrolidin-1-yl)ethanamine. The title compound was isolated after purification on silica gel (15 g) eluting with 10/90 2M ammonia in methanol/methylene chloride. $^1$H NMR (500 MHz, DMSO-d$_6$) δ 11.35 (s, 1H), 8.25 (m, 2H) 8.12 (d, 1H) 7.79 (s, 1H), 7.69 (dd, 1H), 7.06 (m, 1H), 6.73 (m, 1H), 3.94 (m, 1H), 2.93 (m, 1H), 2.77 (m, 1H), 2.38 (m 2H), 1.83 (m, 4H), 1.53 (m, 1H), 1.38 (, 1H), 1.01 (t, 3H).

EXAMPLE 81

4-oxo-N-(4-phenylbutyl)-4,5-dihydropyrrolo[1,2-a]quinoxaline-7-carboxamide

The title compound was prepared as described as in EXAMPLE 61E, substituting 4-phenylbutan-1-amine for 2-(pyrrolidin-1-yl)ethanamine. $^1$H NMR (500 MHz, DMSO-d$_6$) δ 11.36 (s, 1H), 8.54 (t, 1H), 8.24 (s, 1H), 8.11 (d, 1H) 7.78 (s, 1H), 7.66 (dd, 1H), 7.26 (m, 2H), 7.22 (m, 3H), 7.07 (m, 1H), 6.72 (m, 1H), 3.30 (q, 2H) 2.62 (t, 2H) 1.60 (m, 4H).

EXAMPLE 82

7-(pyrrolidin-1-ylcarbonyl)pyrrolo[1,2-a]quinoxalin-4(5H)-one

The title compound was prepared as described as in EXAMPLE 61E, substituting pyrrolidine for 2-(pyrrolidin-1-yl)ethanamine. $^1$H NMR (400 MHz, DMSO-d$_6$) δ 8.22 (m, 1H), 8.08 (d, 1H), 7.45 (s, 1H), 7.37 (dd, 1H) 7.06 (m, 1H), 6.72 (m, 1H), 3.46 (m 4H), 1.86 (m, 4H).

EXAMPLE 83

N-[4-(4-benzylpiperazin-1-yl)phenyl]-4-oxo4,5-dihydropyrrolo[1,2-a]quinoxaline-7-carboxamide The title compound was prepared as described as in EXAMPLE 61E, substituting 4-(4-benzylpiperazin-1-yl) aniline for 2-(pyrrolidin-1-yl)ethanamine. $^1$R NMR (300 MHz, DMSO-d$_6$) δ 11.00 (s, 1H) 9.78 (s, 1H) 8.08 (s, 1H), 7.99 (d, 1H), 7.80 (s, 1H), 7.70 (d, 1H), 7.50 (d, 2H), 7.26 (m, 5H), 7.00 (m, 1H), 6.82 (d, 2H) 6.63 (t, 1H), 3.49 (s, 2H), 3.07 (m, 4H), 2.49 (m, 2H) 2.41 (m, 2H).

EXAMPLE 84

4-oxo-N-1,3-thiazol-2-yl-4,5-dihydropyrrolo[1,2-a]quinoxaline-7-carboxamide

The title compound was prepared as described as in EXAMPLE 61E, substituting thiazol-2-amine for 2-(pyrrolidin-1-yl)ethanamine. $^1$H NMR (300 MHz, DMSO-d$_6$) δ 11.15 (br s, 1H), 8.16 (m, 1H), 8.10 (d, 1H), 7.97 (m, 3H), 7.52 (d, 1H), 7.21 (d, 1H), 7.07 (m, 1H), 6.72 (m, 1H).

EXAMPLE 85

7-(piperidin-1-ylcarbonyl)pyrrolo[1,2-a]quinoxalin-4(5H)-one

The title compound was prepared as described as in EXAMPLE 61E, substituting piperidine for 2-(pyrrolidin-1-yl)ethanamine. $^1$H NMR (400 MHz, DMSO-d$_6$) δ 11.32 (br s, 1H), 8.21 (m, 1H), 8.09 (d, 1H), 7.29 (s, 1H), 7.20 (dd, 1H), 7.06 (m, 1H), 6.71 (m, 1H), 3.40 (m, 4H), 1.64 (m, 2H), 1.53 (m, 4H).

EXAMPLE 86

7-[(4-aminopiperidin-1-yl)methyl]pyrrolo[1,2-a]quinoxalin-4(5H)-one

The title compound was prepared as described in EXAMPLE 1E, substituting tert-butyl piperidin-4-ylcarbamate for cyclohexylamine. The crude mixture was concentrated and dissolved in 2 mL 1:1 TFA:methylene chloride After stirring for 12 hours, the mixture was concentrated and purified by RP-HPLC eluting with 10/90 acetonitirle/0.1% TFA in water at 254 nm. The free base was isolated after eluting from an ion exchange column (10 g). $^1$H NMR (400 MHz, DMSO-d$_6$) δ 8.14 (m, 1H), 7.97 (d, 1H) 7.24 (m, 1H), 7.10 (dd, 1H) 7.01 (m, 1H), 6.67 (m, 1H), 3.45 (s, 2H) 3.31 (br s, 2H), 2.73 (m, 2H), 2.57 (m, 1H), 1.96 (t, 2H), 1.67 (br d, 2H) 1.27 (m, 2H).

EXAMPLE 87

7-[(4-aminopiperidin-1-yl)carbonyl]pyrrolo[1,2-a]quinoxalin-4(5H)-one

The title compound was prepared as described as in EXAMPLE 61E, substituting tert-butyl piperidin-4-ylcarbamate for 2-(pyrrolidin-1-yl)ethanamine. The crude mixture was concentrated and dissolved in 2 mL 1:1 TFA:methylene chloride After stirring for 12 hours, the mixture was concentrated and purified by RP-HPLC eluting with 10/90 acetonitrile/0.1% TFA in water at 254 nm. The title compound was isolated as the free base after eluting from an ion exchange column (10 g). $^1$H NMR (500 MHz, DMSO-d$_6$) δ 8.22 (s, 1H), 8.10 (d, 1H), 7.30 (s, 1H), 7.20 (d, 1H), 7.06 (m, 1H), 6.72 (m, 1H), 4.27 (br s, 2H), 3.05 (m, 4H), 2.86 (m, 1H), 1.76 (m, 2H), 1.20 (m, 2H).

EXAMPLE 88

7-(1,4-diazepan-1-ylcarbonyl)pyrrolo[1,2-a]quinoxalin-4(5H)-one

The title compound was prepared as a TFA salt as described as in EXAMPLE 61, substituting tert-butyl 1,4-diazepane-1-carboxylate for 2-(pyrrolidin-1-yl)ethanamine. The crude mixture was concentrated and dissolved in 2 mL 1:1 TFA:methylene chloride After stirring for 12 hours, the mixture was concentrated and purified by RP-HPLC eluting with 10/90 acetonitirle/0.1% TFA in water at 254 nm. $^1$H NMR (400 MHz, DMSO-$d_6$) δ 11.40 (s, 1H), 8.94 (br s, 1H), 8.23 (s, 1H), 8.12 (d, 1H), 7.34 (s, 1H), 7.29 (d, 1H), 7.07 (m, 1H), 6.73 (m 1H), 3.84 (m, 1H), 3.64 (m, 2H), 3.49 (m, 1H), 3.23 (m, 4H), 1.98 (m, 2H).

EXAMPLE 89

6-(pyrrolidin-1-ylcarbonyl)pyrrolo[1,2-a]quinoxalin-4(5H)-one

EXAMPLE 89A

The title compound was prepared as described in EXAMPLE 34A, substituting methyl 1H-pyrrole-2-carboxylate for ethyl pipecolinate and substituting 1-bromo-3-fluoro-2-nitrobenzene for 4-fluoro-3-nitro-benzoic acid. MS (ESI) m/e 324 (M+H)$^+$.

EXAMPLE 89B

EXAMPLE 89A (577 mg), dichloro[1,1'-ferrocenylbis(diphenyl-phosphine)]palladium (II) dichloromethane (80 mg), and triethylamine (0.5 mL) were dissolved in 50 mL methanol. The mixture was heated at 100° C. under 60 psi of carbon monoxide for 3 hours. The mixture was filtered through Celite to remove the catalyst. The title compound was isolated after purification on silica gel (40 g) eluting with 1:4 ethyl acetate:hexane. MS (ESI) m/e 242 (M+H)$^+$.

EXAMPLE 89C

EXAMPLE 89B (45 mg) was dissolved in 3 mL 5:1 THF:methanol and 1 mL 1M lithium hydroxide was added. After stirring for 12 hours, the mixture was neutralized with 2M HCl. The resultant solid was collected and dried. MS (ESI) m/e 228 (M+H)$^+$.

EXAMPLE 89D

6-(pyrrolidin-1-ylcarbonyl)pyrrolo[1,2-a]quinoxalin-4(5H)-one

The title compound was prepared as described in EXAMPLE 61E, substituting EXAMPLE 89C for EXAMPLE 61D and substituting pyrrolidine for 2-(pyrrolidin-1-yl)ethanamine. $^1$H NMR (400 MHz, DMSO-$d_6$) δ 10.36 (s, 1H), 8.23 (s, 1H), 8.15 (d, 1H) 7.38 (m, 1H), 7.27 (d, 1H), 7.08 (m, 1H), 6.72 (m, 1H), 3.56 (t, 2H), 3.32 (t, 2H), 1.86 (m, 4H).

The foregoing is meant to be illustrative of the invention and not meant to limit it to disclosed embodiments. Variations and changes obvious to one skilled in the art are intended to be within the scope and nature of the invention as defined in the appended claims.

We claim:
1. A compound having formula I

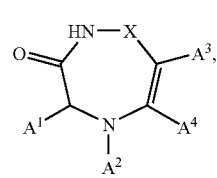

or a pharmarceutically acceptable salt thereof, wherein
X is a bond;
$A^1$ and $A^2$, together with the atoms to which they are attached, are pyrrole;
$A^3$ and $A^4$, together with the atoms to which they are attached, are benzene which is substituted with S(O)R$^1$, SO$_2$R$^1$, C(O)R$^1$, C(O)NH$_2$, C(O)NHR$^1$, C(O)N(R$^1$)$_2$, NHC(O)R$^1$, NR$^{11}$C(O)R$^{11}$, NHSO$_2$R$^{11}$, NR$^{11}$SO$_2$R$^{11}$, NHC(O)OR$^1$, NR$^1$C(O)OR$^1$, SO$_2$NH$_2$, SO$_2$NHR$^1$, SO$_2$N(R$^1$)$_2$, NHC(O)NH$_2$, NHC(O)NHR$^1$, NHC(O)N(R$^1$)$_2$, C(O)OH, or alkyl, wherein the alkyl is substituted with one or two independently selected R$^6$, C(O)OH, NH$_2$, NHR$^6$, N(R$^6$)$_2$, C(O)R$^6$, C(O)NH$_2$, C(O)NHR$^6$, C(O)N(R$^6$)$_2$, NHC(O)R$^6$, or NR$^6$C(O)R$^6$;
R$^1$ is R$^2$, R$^3$, R$^4$ or R$^5$;
R$^2$ is phenyl which is unfused or fused with benzene, heteroarene, cycloalkane, cycloalkene, heterocycloalkane or heterocycloalkene;
R$^3$ is heteroarene which is unfused or fused with benzene, heteroarene, cycloalkane, cycloalkene, heterocycloalkane or heterocycloalkene;
R$^4$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;
R$^5$ is alkyl, alkenyl or alkynyl, each of which is unsubstituted or substituted with one or two of independently selected R$^6$, C(O)OH, NH$_2$, NHR$^6$, N(R$^6$)$_2$, C(O)R$^6$, C(O)NH$_2$, C(O)NHR$^6$, C(O)N(R$^6$)$_2$, NHC(O)R$^6$, or NR$^6$C(O)R$^6$;
R$^6$ is R$^7$, R$^8$, R$^9$ or R$^{10}$;
R$^7$ is phenyl which is unfused or fused with benzene, heteroarene, cycloalkane, cycloalkene, heterocycloalkane or heterocycloalkene;
R$^8$ is heteroarene which is unfused or fused with benzene, heteroarene, cycloalkane, cycloalkene, heterocycloalkane or heterocycloalkene;
R$^9$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;
R$^{10}$ is alkyl, alkenyl or alkynyl, each of which is unsubstituted or substituted with one or two of independently selected R$^{11}$, C(O)OH, NH$_2$, NHR$^{11}$, N(R$^{11}$)$_2$, C(O)R$^{11}$, C(O)NH$_2$, C(O)NHR$^{11}$, C(O)N(R$^{11}$)$_2$, NHC(O)R$^{11}$, NR$^{11}$C(O)R$^{11}$, F, Cl, Br or I;
R$^{11}$ is R$^{12}$, R$^{13}$, or R$^{14}$;
R$^{12}$ is phenyl which is unfused or fused with benzene, heteroarene, cycloalkane, cycloalkene, heterocycloalkane or heterocycloalkene;
R$^{13}$ is heteroarene which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;
wherein the moieties represented by $A^1$ and $A^2$ and $A^2$ and $A^3$ and the moieties represented by $R^2$, $R^3$, $R^4$, $R^7$, $R^8$, $R^9$, $R^{12}$, $R^{13}$ and $R^{14}$ are independently unsubstituted or substituted with $R^{15}$, $OR^{15}$, $SR^{15}$, $S(O)R^{15}$, $SO_2R^{15}$, $NH_2$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NR^{15}SO_2R^{15}$, $NHC(O)OR^{15}$, $NR^{15}C(O)OR^{15}$, $SO_2NH_2$, $SO_2NHR^{15}$, $SO_2N(R^{15})_2$, $NHC(O)NH_2$, $NHC(O)NHR^{15}$, $NHC(O)N(R^{15})_2$, $NR^{15}C(O)N(R^{15})_2$, OH, (O), C(O)OH, CN, $CF_3$, $OCF_3$, $CF_2CF_3$, F, Cl, Br or I;
wherein $R^{15}$ is $R^{16}$, $R^{17}$, $R^{18}$ or $R^{19}$;
$R^{16}$ is phenyl which is unfused or fused with benzene;
$R^{17}$ is heteroaryl which is unfused or fused with benzene;
$R^{18}$ is cycloalkyl, cycloalkenyl, heterocycloalkyl or heterocycloalkenyl, each of which is unfused or fused with benzene;
$R^{19}$ is alkyl, alkenyl or alkynyl, each of which is unsubstituted or substituted with one or two of independently selected $R^{20}$, C(O)OH, $NH_2$, $NHR^{20}$, $N(R^{20})_2$, $C(O)R^{20}$, $C(O)NH_2$, $C(O)NHR^{20}$, $C(O)N(R^{20})_2$, $NHC(O)R^{20}$, $NR^{20}C(O)R^{20}$, F, Cl, Br or I;
$R^{20}$ is $R^{21}$ or $R^{21A}$;
$R^{21}$ is phenyl, heteroaryl, cycloalkyl, cycloalkenyl, heterocycloalkyl, or heterocycloalkenyl;
$R^{21A}$ is alkyl, alkenyl or alkynyl, each of which is unsubstituted or substituted with one or two of independently selected $R^{22}$, C(O)OH, $NH_2$, $NHR^{22}$, $N(R^{22})_2$, $C(O)R^{22}$, $C(O)NH_2$, $C(O)NHR^{22}$, $C(O)N(R^{22})_2$, $NHC(O)R^{22}$, $NR^{22}C(O)R^{22}$, F, Cl, Br or I; and
$R^{22}$ is phenyl, heteroaryl, cycloalkyl, cycloalkenyl, heterocycloalkyl or heterocycloalkenyl.

2. The compound of claim 1 wherein
$A^3$ and $A^4$, together with the atoms to which they are attached, are benzene which is substituted with $C(O)R^1$, $C(O)NHR^1$, $C(O)N(R^1)_2$, or alkyl which is substituted with one or two of independently selected $R^6$, $NHR^6$, $N(R^6)_2$, $C(O)R^6$, or $NR^6C(O)R^6$;
$R^1$ is $R^2$, $R^3$, $R^4$ or $R^5$;
$R^2$ is phenyl;
$R^3$ is heteroarene;
$R^4$ is cycloalkyl or heterocycloalkyl;
$R^5$ is alkyl which is unsubstituted or substituted with one or two of independently selected $R^6$, $NHR^6$, $N(R^6)_2$, $C(O)R^6$, or $NR^6C(O)R^6$;
$R^6$ is $R^7$, $R^8$, $R^9$ or $R^{10}$;
$R^7$ is phenyl;
$R^8$ is heteroarene;
$R^9$ is cycloalkyl or heterocycloalkyl;
$R^{10}$ is alkyl which is unsubstituted or substituted with one or two of independently selected $R^{11}$, C(O)OH, $N(R^{11})_2$, or $C(O)R^{11}$;
$R^{11}$ is $R^{12}$ or $R^{14}$;
$R^{12}$ is phenyl;
$R^{14}$ is cycloalkyl or heterocycloalkyl;
wherein the moieties represented by $R^2$, $R^4$, and $R^9$ are independently unsubstituted or substituted with $R^{15}$, $SO_2R^{15}$, $NH_2$, $N(R^{15})_2$, or (O);
$R^{15}$ is $R^{18}$ or $R^{19}$;
$R^{18}$ is heterocycloalkyl; and
$R^{19}$ is alkyl.

3. The compound of claim 1 wherein
$A^3$ and $A^4$, together with the atoms to which they are attached, are benzene which is substituted with $R^{1A}$ and $R^{1B}$ as described in Formula IV

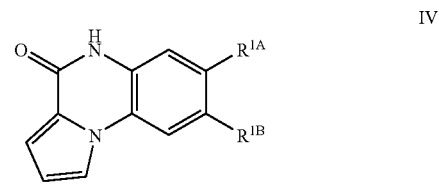

one of $R^{1A}$ and $R^{1B}$ is H, and the other is selected from with $S(O)R^1$, $SO_2R^1$, $C(O)R^1$, $C(O)NH_2$, $C(O)NHR^1$, $C(O)N(R^1)_2$, $NHC(O)R^1$, $NR^{11}C(O)R^{11}$, $NHSO_2R^{11}$, $NR^{11}SO_2R^{11}$, $NHC(O)OR^1$, $NR^1C(O)OR^1$, $SO_2NH_2$, $SO_2NHR^1$, $SO_2N(R^1)_2$, $NHC(O)NH_2$, $NHC(O)NHR^1$, $NHC(O)N(R^1)_2$, C(O)OH, or alkyl, wherein the alkyl is substituted with one or two independently selected $R^6$, C(O)OH, $NH_2$, $NHR^6$, $N(R^6)_2$, $C(O)R^6$, $C(O)NH_2$, $C(O)NHR^6$, $C(O)N(R^6)_2$, $NHC(O)R^6$, or $NR^6C(O)R^6$.

4. The compound of claim 3 wherein one of $R^{1A}$ and $R^{1B}$ is H, and the other is $C(O)R^1$, $NHC(O)R^1$, or $NR^{11}C(O)R^{11}$.

5. The compound of claim 3 wherein one of $R^{1A}$ and $R^{1B}$ is H, and the other is alkyl which is substituted with one or two of independently selected $R^6$, $NHR^6$, $N(R^6)_2$, $C(O)R^6$, or $NR^6C(O)R^6$.

6. The compound of claim 5 wherein
one of $R^{1A}$ and $R^{1B}$ is H, and the other is alkyl which is substituted with $NHR^6$ or $N(R^6)_2$;
$R^6$ is $R^9$ or $R^{10}$;
$R^9$ is cycloalkyl or heterocycloalkyl;
$R^{10}$ is alkyl which is unsubstituted or substituted with one or two of independently selected $R^{11}$, C(O)OH, $N(R^{11})_2$, or $C(O)R^{11}$;
$R^{11}$ is $R^{12}R^{14}$;
$R^{12}$ is phenyl;
$R^{14}$ is cycloalkyl or heterocycloalkyl;
wherein the moiety represented by $R^9$ is independently unsubstituted or substituted with $R^{15}$, $SO_2R^{15}$, $NH_2$, $N(R^{15})_2$, or (O);
$R^{15}$ is $R^{18}$ or $R^{19}$;
$R^{18}$ is heterocycloalkyl; and
$R^{19}$ is alkyl.

7. A pharmaceutical composition comprising a compound of claim 1 and a pharmaceutically acceptable excipient.

8. The compound of claim 1, selected from the group consisting of:
7-[(cyclohexylamino)methyl]pyrrolo[1,2-a]quinoxalin-4 (5H)-one;
7-{[(cyclohexylmethyl)amino]methyl}pyrrolo [1,2-a]quinoxalin-4(5H)-one;
7-[(cyclobutylamino)methyl]pyrrolo[1,2-a]quinoxalin-4 (5H)-one;
7-[(cyclopentylamino)methyl]pyrrolo[1,2-a]quinoxalin-4 (5H)-one;
7-[(cyclopropylamino)methyl]pyrrolo[1,2-a]quinoxalin-4 (5H)-one;
7-(piperidin-1-ylmethyl)pyrrolo[1,2-a]quinoxalin-4(5H)-one;
7-(pyrrolidin-1-ylmethyl)pyrrolo[1,2-a]quinoxalin-4 (5H)-one;
8-[(cyclohexylamino)methyl]pyrrolo[1,2-a]quinoxalin-4 (5H)-one;

8-[(cyclohexylamino)methyl]pyrrolo[1,2-a]quinoxalin-4(5H)-one;
7-[(isopropylamino)methyl]pyrrolo[1,2-a]quinoxalin-4(5H)-one;
7-[(benzylamino)methyl]pyrrolo[1,2-a]quinoxalin-4(5H)-one;
8-[(isopropylamino)methyl]pyrrolo[1,2-a]quinoxalin-4(5H)-one;
8-{[(2-phenylethyl)amino]methyl}pyrrolo[1,2-a]quinoxalin-4(5H)-one;
8-(pyrrolidin-1-ylmethyl)pyrrolo[1,2-a]quinoxalin-4(5H)-one;
8-[(cyclobutylamino)methyl]pyrrolo[1,2-a]quinoxalin-4(5H)-one;
8-(morpholin-4-ylmethyl)pyrrolo[1,2-a]quinoxalin-4(5H)-one;
8-[(cyclopentylamino)methyl]pyrrolo[1,2-a]quinoxalin-4(5H)-one;
8-(piperidin-1-ylmethyl)pyrrolo[1,2-a]quinoxalin-4(5H)-one; and
8-[(benzylamino)methyl]pyrrolo[1,2-a]quinoxalin-4(5H)-one.

* * * * *

UNITED STATES PATENT AND TRADEMARK OFFICE
CERTIFICATE OF CORRECTION

PATENT NO. : 7,790,721 B2  
APPLICATION NO. : 11/964788  
DATED : September 7, 2010  
INVENTOR(S) : Giranda et al.

Page 1 of 1

It is certified that error appears in the above-identified patent and that said Letters Patent is hereby corrected as shown below:

Column 84, line 3, claim 1: "pharmarceutically" to read as --pharmaceutically--

Column 85, line 56, claim 2: "$N(R^{11})_2$," to read as --$N(R^{11})_2$,--

Column 86, line 15, claim 3: "selected from with" to read as --selected from--

Column 86, line 37, claim 6: "$N(R^{11})_2$," to read as --$N(R^{11})_2$,--

Column 86, line 38, claim 6: "$R^{11}$ is $R^{12}$ $R^{14}$" to read as --$R^{11}$ is $R^{12}$ or $R^{14}$--

Signed and Sealed this
Eighth Day of November, 2011

David J. Kappos
*Director of the United States Patent and Trademark Office*